(12) United States Patent
Nakano et al.

(10) Patent No.: US 11,864,594 B2
(45) Date of Patent: Jan. 9, 2024

(54) AEROSOL GENERATION DEVICE, CONTROL METHOD AND STORAGE MEDIUM

(71) Applicant: JAPAN TOBACCO INC., Tokyo (JP)

(72) Inventors: Takuma Nakano, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 751 days.

(21) Appl. No.: 17/031,926

(22) Filed: Sep. 25, 2020

(65) Prior Publication Data

US 2021/0007410 A1  Jan. 14, 2021

Related U.S. Application Data

(63) Continuation of application No. PCT/JP2018/012243, filed on Mar. 26, 2018.

(51) Int. Cl.
*A24F 40/57* (2020.01)
*A24F 40/53* (2020.01)
(Continued)

(52) U.S. Cl.
CPC .............. *A24F 40/53* (2020.01); *A24F 40/57* (2020.01); *A61M 11/042* (2014.02);
(Continued)

(58) Field of Classification Search
CPC .......... A24F 40/20; A24F 40/53; A24F 40/57; A61M 11/042; A61M 15/06;
(Continued)

(56) References Cited

U.S. PATENT DOCUMENTS 10,206,431 B2 * 2/2019 Sur .................. H05B 1/0244
10,688,275 B2 * 6/2020 Moll Neto ........ A61M 15/0001
(Continued)

FOREIGN PATENT DOCUMENTS

CN  107530511 A  1/2018
EP  2967140  1/2016
(Continued)

OTHER PUBLICATIONS

International Search Report and Written Opinion dated Jun. 26, 2018 for PCT/JP2018/012243 filed on Mar. 26, 2018, 10 pages including English Translation of the International Search Report.
(Continued)

*Primary Examiner* — Thanh Tam T Le
(74) *Attorney, Agent, or Firm* — XSENSUS LLP

(57) ABSTRACT

An aerosol generation device includes: a load configured to heat an aerosol generation article including an aerosol-forming substrate configured to hold or carry at least one of an aerosol source and a flavor source; and a controller configured to control power that is supplied from a power source to the load. When a phase where a temperature of the load is equal to or higher than a value at which a predetermined amount or more of aerosols is capable of being generated from the aerosol generation article, the controller is configured to acquire the temperature of the load and a degree of progress of the phase, to execute feedback control so that the temperature of the load converges to a predetermined temperature, and to increase a gain in the feedback control or an upper limit value of the power, as the degree of progress progresses, in the feedback control.

20 Claims, 52 Drawing Sheets

(51) Int. Cl.
*A61M 11/04* (2006.01)
*A61M 15/06* (2006.01)
*A24F 40/20* (2020.01)

(52) U.S. Cl.
CPC ............. *A61M 15/06* (2013.01); *A24F 40/20* (2020.01); *A61M 2205/3368* (2013.01); *A61M 2205/8206* (2013.01); *G05B 2219/25409* (2013.01)

(58) Field of Classification Search
CPC .. A61M 2205/3368; A61M 2205/8206; G05B 2219/25409
See application file for complete search history.

(56) References Cited

U.S. PATENT DOCUMENTS

| | | | | |
|---|---|---|---|---|
| 10,765,146 | B2* | 9/2020 | Sur | H02M 3/04 |
| 11,094,993 | B2* | 8/2021 | Sur | A24F 40/90 |
| 11,291,252 | B2* | 4/2022 | Sur | H04B 5/0081 |
| 11,337,464 | B2* | 5/2022 | Lee | A24F 40/95 |
| 11,456,480 | B2* | 9/2022 | Sur | A24F 40/50 |
| 11,470,689 | B2* | 10/2022 | Sur | A61M 11/042 |
| 11,484,673 | B2* | 11/2022 | Soriano | A61M 15/06 |
| 11,523,469 | B2* | 12/2022 | Courbat | H05B 3/22 |
| 11,589,321 | B2* | 2/2023 | Roth-Mandutz | H04W 52/288 |
| 2014/0270727 | A1 | 9/2014 | Ampolini et al. | |
| 2014/0345606 | A1 | 11/2014 | Talon | |
| 2014/0345633 | A1 | 11/2014 | Talon et al. | |
| 2015/0208727 | A1 | 7/2015 | Kuczaj | |
| 2015/0230521 | A1 | 8/2015 | Talon | |
| 2015/0237916 | A1 | 8/2015 | Farine et al. | |
| 2016/0174610 | A1 | 6/2016 | Kuczaj | |
| 2016/0331038 | A1 | 11/2016 | Farine et al. | |
| 2017/0224019 | A1 | 8/2017 | Kuczaj | |
| 2018/0042308 | A1 | 2/2018 | Takeuchi et al. | |
| 2019/0059448 | A1 | 2/2019 | Talon | |
| 2019/0297951 | A1 | 10/2019 | Kuczaj | |
| 2019/0313698 | A1 | 10/2019 | Kuczaj | |

FOREIGN PATENT DOCUMENTS

| | | |
|---|---|---|
| EP | 3272382 A1 | 1/2018 |
| GB | 2527349 A | 12/2015 |
| JP | 6046231 B2 | 12/2016 |
| JP | 6062457 B2 | 1/2017 |
| JP | 6125008 B2 | 5/2017 |
| WO | 2014/150247 A1 | 9/2014 |
| WO | 2019/068821 A1 | 4/2019 |

OTHER PUBLICATIONS

Chinese Office Action dated Dec. 9, 2022, in corresponding Chinese Patent Application No. 201880091843.3.
Extended European Search Report dated Feb. 19, 2021 in European Application No. 18912023.1.

* cited by examiner

FIG. 29

| | PREPARATION PHASE | USE PHASE |
|---|---|---|
| PHASE END CONDITION | LAPSE OF PREDETERMINED TIME | LAPSE OF PREDETERMINED TIME AND REACHING PREDETERMINED TEMPERATURE |
| EXECUTION TIME | SHORT | LONG |
| POWER CONSUMPTION | LARGE | SMALL |
| CONTROL MODE | F/F | F/B + (F/F) |
| ENVIRONMENT SETTING BEFORE PHASE START | NECESSARY (ENVIRONMENT TEMPERATURE + SOC) | NOT NECESSARY OR NECESSARY (ENVIRONMENT TEMPERATURE = PREPARATION PHASE END TEMPERATURE) |
| CHANGE OF CONTROL VARIABLE DURING PHASE | △ | ○ |
| RECOVERY OF DECREASE IN TEMPERATURE DUE TO INHALATION | × | ○ |
| INPUT PARAMETER OF F/F CONTROL | TIMER VALUE t | MEASURED TEMPERATURE VALUE, TIMER VALUE t, PUFF PROFILE |
| CHANGE IN MEASURED TEMPERATURE VALUE | LINEAR INCREASE | CURVED INCREASE |

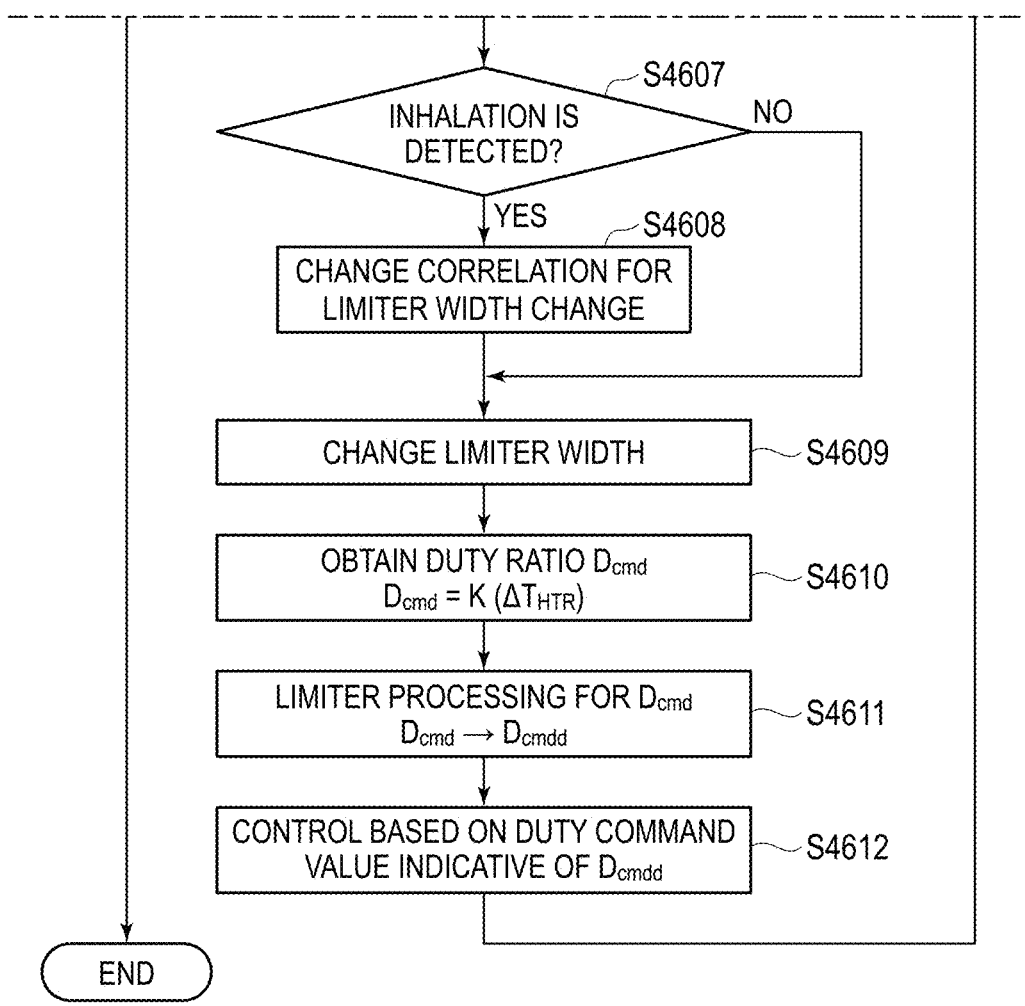
*(FIG.46 Continued)*

*(FIG.52 Continued)*
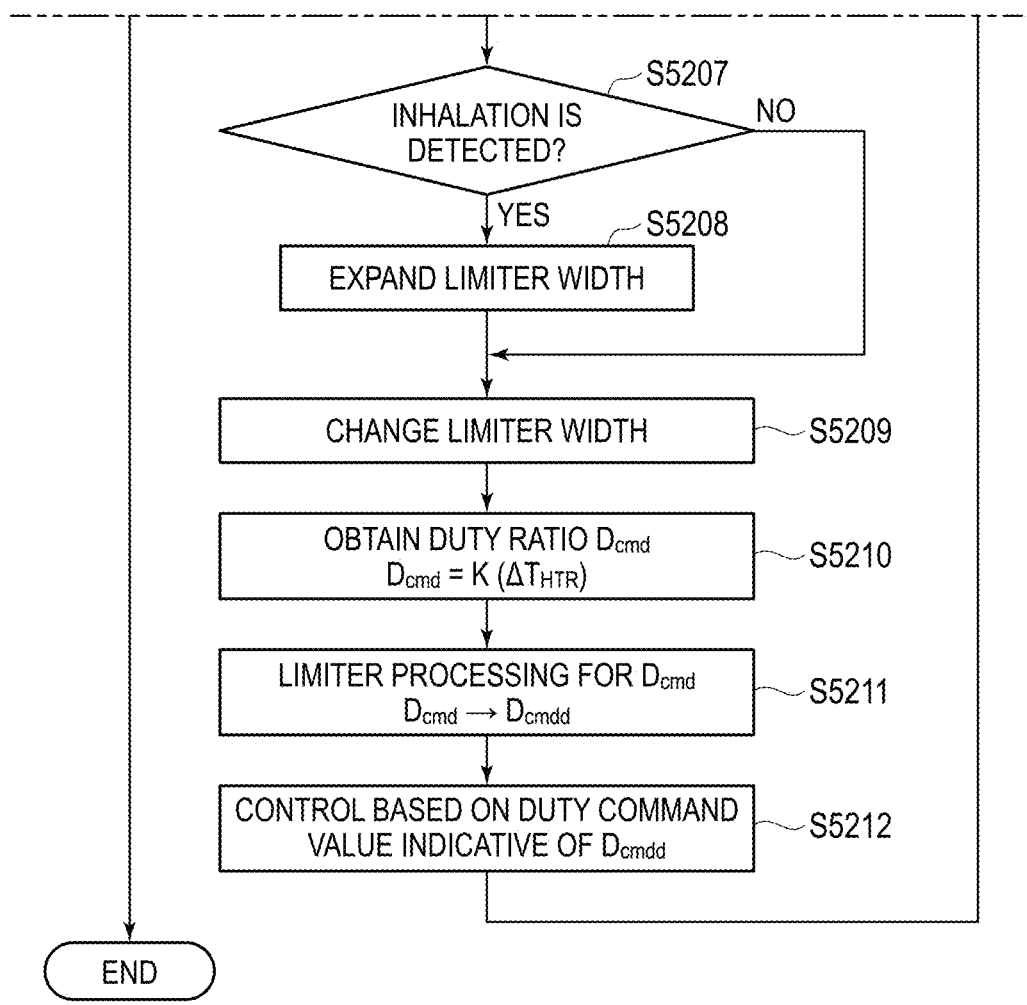

AEROSOL GENERATION DEVICE, CONTROL METHOD AND STORAGE MEDIUM

CROSS-REFERENCE TO RELATED APPLICATION(S)

This application is a continuation of PCT application No. PCT/JP2018/012243, which was filed on Mar. 26, 2018, the contents of which are incorporated herein by reference.

TECHNICAL FIELD

The present invention relates to an aerosol generation device, a control method and a storage medium.

BACKGROUND

For example, an aerosol generation device configured to heat an aerosol generation article by an electric heating element such as an electric heater, and to generate aerosols is used.

The aerosol generation device includes an electric heating element and a control unit configured to control the electric heating element itself or power that is supplied to the electric heating element. The aerosol generation device is mounted with an aerosol generation article such as a stick or pod including cigarette formed into a sheet or particle shape, for example. The aerosol generation article is heated by the electric heating element, so that aerosols are generated.

As a heating method of the aerosol generation article, there are three following heating methods, for example.

In a first heating method, a rod-shaped electric heating element is inserted into the aerosol generation article, and the electric heating element inserted into the aerosol generation article heats the aerosol generation article. Japanese Patent Nos. 6,046,231, 6,125,008 and 6,062,457 and the like disclose control technologies on the heating by the first heating method, for example.

In a second heating method, an annular electric heating element coaxial with the aerosol generation article is arranged on an outer peripheral part of the aerosol generation article, and the electric heating element heats the aerosol generation article from an outer periphery-side of the aerosol generation article.

In a third heating method, a metal piece (also referred to as 'susceptor') that generates heat by eddy current generated therein by a magnetic field penetrating the metal piece is inserted in advance in the aerosol generation article. Then, the aerosol generation article is mounted to an aerosol generation device having a coil, AC current is enabled to flow through the coil to generate a magnetic field, and the metal piece in the aerosol generation article mounted to the aerosol generation device is heated using an induction heating (IH) phenomenon.

For example, it is preferable that a time period from start of heating until a user can inhale aerosols is short in the aerosol generation device, from a standpoint of convenience of the aerosol generation device. Also, from a standpoint of a quality of the aerosol generation device, it is preferable to stabilize an amount of generation of aerosols after the user can inhale aerosols until the heating is over, thereby stabilizing flavor and taste that are given to the user.

The present invention has been made in view of the above situations, and is to provide an aerosol generation device, a control method and a storage medium capable of appropriately heating an aerosol generation article to thereby stabilize an amount of aerosol generation.

SUMMARY

An aerosol generation device relating to a first example includes: a load configured to heat an aerosol generation article by using power that is supplied from a power source, the aerosol generation article including an aerosol-forming substrate configured to hold or carry at least one of an aerosol source and a flavor source; and a control unit configured to control the power that is supplied from the power source to the load. In a case of a use phase where a temperature of the load is equal to or higher than a value at which a predetermined amount or more of aerosols is capable of being generated from the aerosol generation article, the control unit is configured to acquire the temperature of the load and a degree of progress of the use phase, to execute feedback control so that the temperature of the load converges to a predetermined temperature, and to increase a gain in the feedback control or an upper limit value of the power that is supplied from the power source to the load, as the degree of progress progresses, in the feedback control.

A control method relating a second example is a control method of power that is supplied from a power source to a load, in which the load is used to heat an aerosol generation article including an aerosol-forming substrate configured to hold or carry at least one of an aerosol source and a flavor source. The control method includes: starting supply of the power from the power source to the load; in a case of a use phase where a temperature of the load is equal to or higher than a value at which a predetermined amount or more of aerosols is capable of being generated from the aerosol generation article, acquiring the temperature of the load and a degree of progress of the use phase; executing feedback control so that the temperature of the load converges to a predetermined temperature; and increasing a gain in the feedback control or an upper limit value of the power that is supplied from the power source to the load, as the degree of progress progresses, in the feedback control.

An aerosol generation device relating to a third example includes: a load configured to heat an aerosol generation article by using power that is supplied from a power source, the aerosol generation article including an aerosol-forming substrate configured to hold or carry at least one of an aerosol source and a flavor source; and a control unit configured to acquire a temperature of the load, to execute feedback control, based on the temperature of the load, and to control the power that is supplied from the power source to the load. The control unit is configured to increase a gain in the feedback control or an upper limit value of the power that is supplied from the power source to the load so that the temperature of the load gradually approaches from a first temperature, at which a predetermined amount or more of aerosols is capable of being generated from the aerosol source or the aerosol-forming substrate included in the aerosol generation article and located in a position closest to the load, to a second temperature at which the predetermined amount or more of aerosols is capable of being generated from the aerosol source or the aerosol-forming substrate included in the aerosol generation article and located in a position most distant from the load.

A control method relating to a fourth example is a control method of power that is supplied from a power source to a load, in which the load is used to heat an aerosol generation article including an aerosol-forming substrate configured to hold or carry at least one of an aerosol source and a flavor source. The control method includes: starting supply of the power from the power source to the load; acquiring a temperature of the load; executing feedback control, based on the temperature of the load to control the power that is supplied from the power source to the load; and increasing a gain in the feedback control or an upper limit value of the power that is supplied from the power source to the load so that the temperature of the load gradually approaches from a first temperature, at which a predetermined amount or more of aerosols is capable of being generated from the aerosol source or the aerosol-forming substrate included in the aerosol generation article and located in a position closest to the load, to a second temperature at which the predetermined amount or more of aerosols is capable of being generated from the aerosol source or the aerosol-forming substrate included in the aerosol generation article and located in a position most distant from the load.

An aerosol generation device relating to a fifth example includes: a load configured to heat an aerosol generation article by using power that is supplied from a power source, the aerosol generation article including an aerosol-forming substrate configured to hold or carry at least one of an aerosol source and a flavor source; and a control unit configured to control the power that is supplied from the power source to the load. In a case of a use phase where a temperature of the load is equal to or higher than a value at which a predetermined amount or more of aerosols is capable of being generated from the aerosol generation article, the control unit is configured to acquire the temperature of the load and a degree of progress of the use phase, to determine the power that is supplied from the power source to the load, based on a difference between the temperature of the load and a predetermined temperature, and to execute feedback control so that a change rate of a supply amount of the power along with progressing of the use phase is greater than a change rate of the predetermined temperature with the progressing of the use phase.

A control method relating to a sixth example is a control method of power that is supplied from a power source to a load, in which the load is used to heat an aerosol generation article including an aerosol-forming substrate configured to hold or carry at least one of an aerosol source and a flavor source. The control method includes: starting supply of the power from the power source to the load; in a case of a use phase where a temperature of the load is equal to or higher than a value at which a predetermined amount or more of aerosols is capable of being generated from the aerosol generation article, acquiring the temperature of the load and a degree of progress of the use phase; and determining the power that is supplied from the power source to the load, based on a difference between the temperature of the load and a predetermined temperature, and executing feedback control so that a change rate of a supply amount of the power with progressing of the use phase is greater than a change rate of the predetermined temperature with the progressing of the use phase.

An aerosol generation device relating to a second example includes: a load configured to heat an aerosol generation article by using power that is supplied from a power source, the aerosol generation article including an aerosol-forming substrate configured to hold or carry at least one of an aerosol source and a flavor source; and a control unit configured to control the power that is supplied from the power source to the load. In a case of a use phase where a temperature of the load is equal to or higher than a value at which a predetermined amount or more of aerosols is capable of being generated from the aerosol generation article, the control unit is configured to acquire the temperature of the load and a degree of progress of the use phase, to determine the power that is supplied from the power source to the load, based on a difference between the temperature of the load and a predetermined temperature, and to execute feedback control so that a value obtained by subtracting the temperature of the load from the predetermined temperature decreases along with progressing of the use phase and a supply amount of the power that is supplied from the power source to the load increases with the progressing of the use phase.

A control method relating to an eighth example is a control method of power that is supplied from a power source to a load, in which the load is used to heat an aerosol generation article including an aerosol-forming substrate configured to hold or carry at least one of an aerosol source and a flavor source. The control method includes: starting supply of the power from the power source to the load; in a case of a use phase where a temperature of the load is equal to or higher than a value at which a predetermined amount or more of aerosols is capable of being generated from the aerosol generation article, acquiring the temperature of the load and a degree of progress of the use phase; and determining the power that is supplied from the power source to the load, based on a difference between the temperature of the load and a predetermined temperature, and executing feedback control so that a value obtained by subtracting the temperature of the load from the predetermined temperature decreases with progressing of the use phase and a supply amount of the power that is supplied from the power source to the load increases with the progressing of the use phase.

BRIEF DESCRIPTION OF DRAWINGS

FIG. 29 is a table showing comparison of the preparation phase and the use phase that are executed by the control unit in accordance with a third embodiment;

DESCRIPTION OF EMBODIMENTS

Hereinbelow, the present embodiment will be described with reference to the drawings.

In descriptions below, the functions and constitutional elements that are omitted or substantially the same are denoted with the same reference signs, and are described only when necessary.

An aerosol generation device of the present embodiment is described by taking, as an example, an aerosol generation device for an aerosol generation article (solid heating), for example. However, the aerosol generation device of the present embodiment may also be an aerosol generation device of another type or usage, such as a medical nebulizer (spraying device), for example.

The aerosol generation device of the present embodiment is described by taking, as an example, a case where aerosols are generated using the first heating method of heating the aerosol generation article from an inside thereof by using an electric heating element inserted into the aerosol generation article. However, the aerosol generation device of the present embodiment may also use another heating method such as the second heating method of heating the aerosol generation article from an outside thereof by using an annular electric healing element arranged on an outer peripheral part of the aerosol generation article or the third heating method of heating the aerosol generation article from an inside thereof by using an induction heating phenomenon.

Figure 1:
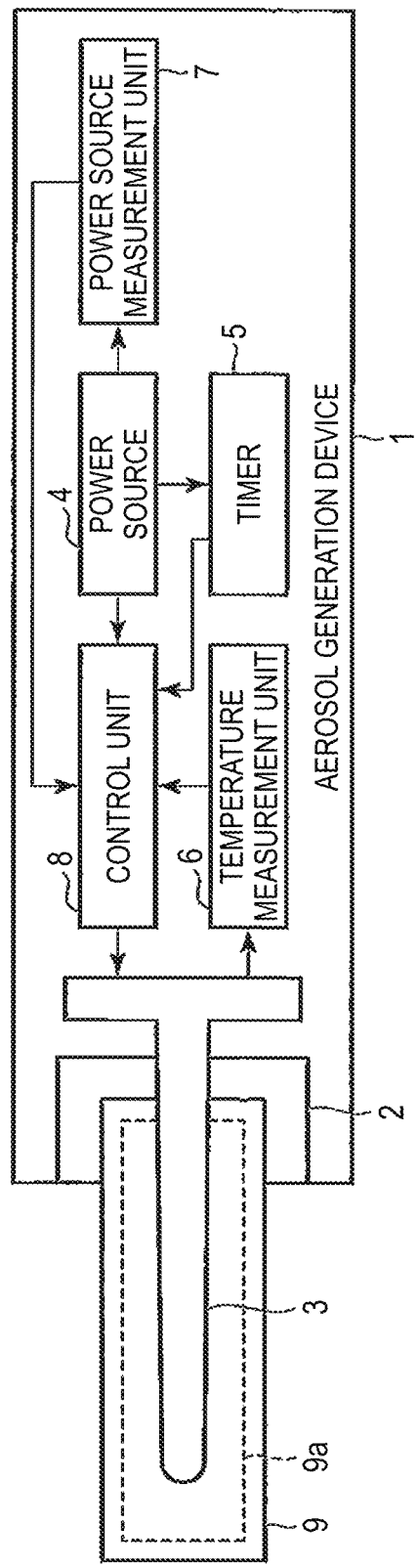
FIG. 1 is a block diagram depicting an example of a basic configuration of an aerosol generation device in accordance with an embodiment.

FIG. 1 is a block diagram depicting an example of a basic configuration of an aerosol generation device 1 in accordance with the embodiment.

The aerosol generation device 1 includes a mounting unit 2, a load 3, a power source 4, a timer 5, a temperature measurement unit 6, a power source measurement unit 7, and a control unit 8.

The mounting unit 2 is configured to detachably support an aerosol generation article 9.

The aerosol generation article 9 includes an aerosol-forming substrate 9a configured to hold or carry at least one of an aerosol source and a flavor source, for example. The aerosol generation article 9 may be a smoking article, for example, and may be formed into a shape such as a stick shape that is easy to use, for example.

The aerosol source may be liquid or solid including polyhydric alcohol such as glycerin or propylene glycol, for example. Also, the aerosol source may further contain a nicotine component, for example, in addition to polyhydric alcohol.

The aerosol-forming substrate 9a is a solid material in which the aerosol source is added or carried, for example, and may be a cigarette sheet, for example.

The aerosol-forming substrate 9a may be a substrate that can emit a volatile compound capable of generating aerosols so that the substrate functions as the aerosol source or the flavor source, for example. The volatile compound is emitted by heating the aerosol-forming substrate 9a. In the present embodiment, the aerosol-forming substrate 9a is a part of the aerosol generation article 9.

The load 3 is, for example, an electric heating element, and is configured to generate heat as power is supplied from the power source 4, thereby heating the aerosol generation article 9 mounted to the mounting unit 2.

The power source 4 is a battery or a battery pack in which a battery, a field emission transistor (FET), an FET for discharge, a protection IC (Integrated Circuit), a monitoring device and the like are combined, and is configured to supply power to the load 3. The power source 4 is a chargeable secondary battery, and may be a lithium-ion secondary battery, for example. The power source 4 may be included in the aerosol generation device 1 or may be configured separately from the aerosol generation device 1.

The timer 5 is configured to output, to the control unit 8, a timer value t indicating a time since the power is supplied to the load 3 in a non-operation state.

Herein, the non-operation state may be a state in which the power source 4 is off or a state in which the power source 4 is on but is not waiting for the supply of power to the load 3. The non-operation state may also be a standby state.

In the meantime, the timer value may also indicate a time counted from start of aerosol generation, a time from start of heating of the load 3, or a time from start of control by the control unit 8 of the aerosol generation device 1.

The temperature measurement unit 6 is configured to measure a temperature of the load 3 (heater temperature), for example, and to output the measured temperature value to the control unit 8. In the meantime, a heater having a positive temperature coefficient (PTC) characteristic that a resistance value changes in accordance with a temperature may be used for the load 3. In this case, the temperature measurement unit 6 may be configured to measure an electric resistance value of the load 3, and to derive a temperature of the load 3 (heater temperature) from the measured electric resistance value.

The power source measurement unit 7 is configured to measure a power source state value indicative of a state of the power source 4 such as a value relating to a remaining amount of the power source 4, a voltage value that is output by the power source 4 or a current that is discharged from the power source 4 or a current that is charged in the power source 4, and to output the power source state value to the control unit 8.

Herein, as the value relating to the remaining amount of the power source 4, for example, an output voltage of the power source 4 may be used. Alternatively, a state of charge (SOC) of the power source 4 may be used. The SOC may be estimated from a voltage or current measured by a sensor by using an open circuit voltage (SOC-OCV) method or a current integration method (Coulomb counting method) of integrating charging and discharging currents of the power source 4.

The control unit 8 is configured to control power that is supplied from the power source 4 to the load 3, based on the timer value input from the timer 5 and the measured temperature value input from the temperature measurement unit 6, for example. Also, the control unit 8 may be configured to execute the control by using the power source state value input from the power source measurement unit 7, for example. The control unit 8 includes a computer, a controller or a processor and a memory, and the computer, controller or processor may be configured to execute a program stored in the memory to execute the control, for example.

Figure 2:
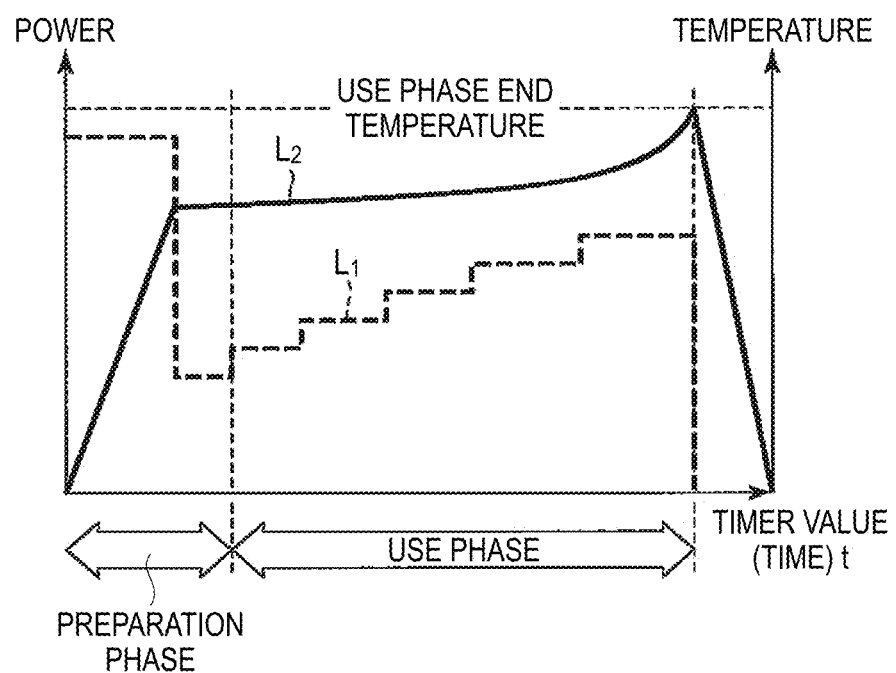
FIG. 2 is a graph depicting an example of changes in power that is supplied to a load by control in accordance with the embodiment and in temperature of the load.

FIG. 2 is a graph depicting an example of changes in power that is supplied to the load 3 by control in accordance with the present embodiment and in temperature of the load 3, In FIG. 2, the horizontal axis indicates the tinier value t, i.e., time, and the vertical axis indicates the power that is supplied to the load 3 and the temperature of the load 3.

The control unit 8 is configured to mainly switch the control between a preparation phase and a use phase.

For example, in the preparation phase, a state in which the load 3 cannot generate a predetermined amount or more of aerosols from the aerosol generation article 9 is referred to as a preparation state. The preparation state may also be a state after heating of the load 3 starts in response to receiving a user's input until the user is allowed to inhale (puff) aerosols with the aerosol generation device 1, for example. In other words, in the preparation state, it is assumed that the user is not allowed to inhale aerosols with the aerosol generation device 1.

The predetermined amount corresponds to an amount of aerosol generation at which the user is allowed to inhale aerosols, for example.

More specifically, the predetermined amount may be an amount at which an effective amount of aerosols can be delivered into a user's mouth, for example. As used herein, the effective amount may be an amount at which the user can be given with flavor and taste originating from the aerosol source or the flavor source included in the aerosol generation article. The predetermined amount may also be an amount of aerosols that are generated by the load 3 and can be delivered into the user's mouth, for example. The predetermined amount may also be an amount of aerosols that are generated when the temperature of the load 3 is equal to or higher than a boiling point of the aerosol source, for example. The predetermined amount may also be an amount of aerosols that are generated from the aerosol generation article 9 when the power supplied to the load 3 is equal to or higher than power that should be supplied to the load 3 so as to generate aerosols from the aerosol generation article 9, for example. In the preparation state, the load 3 may not generate aerosols from the aerosol generation article 9, i.e., the predetermined amount may be zero.

When starting the supply of power to the load 3 in the non-operation state or when the load 3 is in the preparation state, the control unit 8 may control the power that is supplied from the power source 4 to the load 3 by feed-forward control (ET control).

When the load 3 shifts from the preparation state to a use state, the control unit 8 may execute feedback control (F/B control) or both the feedback control and the feed-forward control.

For example, in the use phase, a state in which the load 3 can generate the predetermined amount or more of aerosols from the aerosol generation article 9 is referred to as a use state. The use state may also be a state after the user is allowed to inhale aerosols until the aerosol generation is over, for example.

The control that is executed by the control unit 8 will be specifically described in first to fifth embodiments to be described later.

A dotted line $L_1$ indicates a state in which the power supplied to the load 3 changes in accordance with the timer value t. For example, the control unit 8 may control the power that is supplied from the power source 4 to the load 3 by pulse width modulation (PWM) control or pulse frequency modulation (PFM) control on a switch not shown in FIG. 1. Alternatively, the control unit 8 may control the power that is supplied from the power source 4 to the load 3 by stepping up or stepping down the output voltage of the power source 4 by a DC/DC converter not shown in FIG. 1. In the preparation phase in which the load 3 is in the preparation state, high power is supplied from the power source 4 to the load 3, and then the power that is supplied from the power source 4 to the load 3 is lowered. When the load 3 shifts from the preparation phase to the use phase in which the load is in the use state, the power that is supplied from the power source 4 to the load 3 stepwise increases as the timer value t increases. Then, when an end condition of the use state of the load 3 is satisfied, for example, when the temperature of the load 3 reaches a use phase end temperature or when the timer value t is a threshold value or larger indicative of an end of the use phase, the supply of power to the load 3 is stopped.

A solid line $L_2$ indicates a state in which the temperature of the load 3 changes in accordance with the timer value t. In the preparation phase, the temperature of the load 3 rapidly increases while the high power is supplied from the power source 4 to the load 3. After the power that is supplied from the power source 4 to the load 3 in the preparation phase is lowered, the temperature of the load 3 is kept or slightly increases. When the shift to the use phase is made, the power that is supplied from the power source 4 to the load 3 stepwise increases over time, and the temperature of the load 3 also gradually increases. The control unit 8 executes the feedback control on the basis of the measured temperature value input from the temperature measurement unit 6 so that the temperature of the load 3 is to be the use phase end temperature at the end of the use phase.

The use phase end temperature is a temperature of the load 3 that is set so as to finally converge or reach in the feedback control. The feedback control of the present embodiment controls the supply of power to the load 3 so that there is no difference between the use phase end temperature and the measured temperature value at the end of the use phase.

Figure 3:
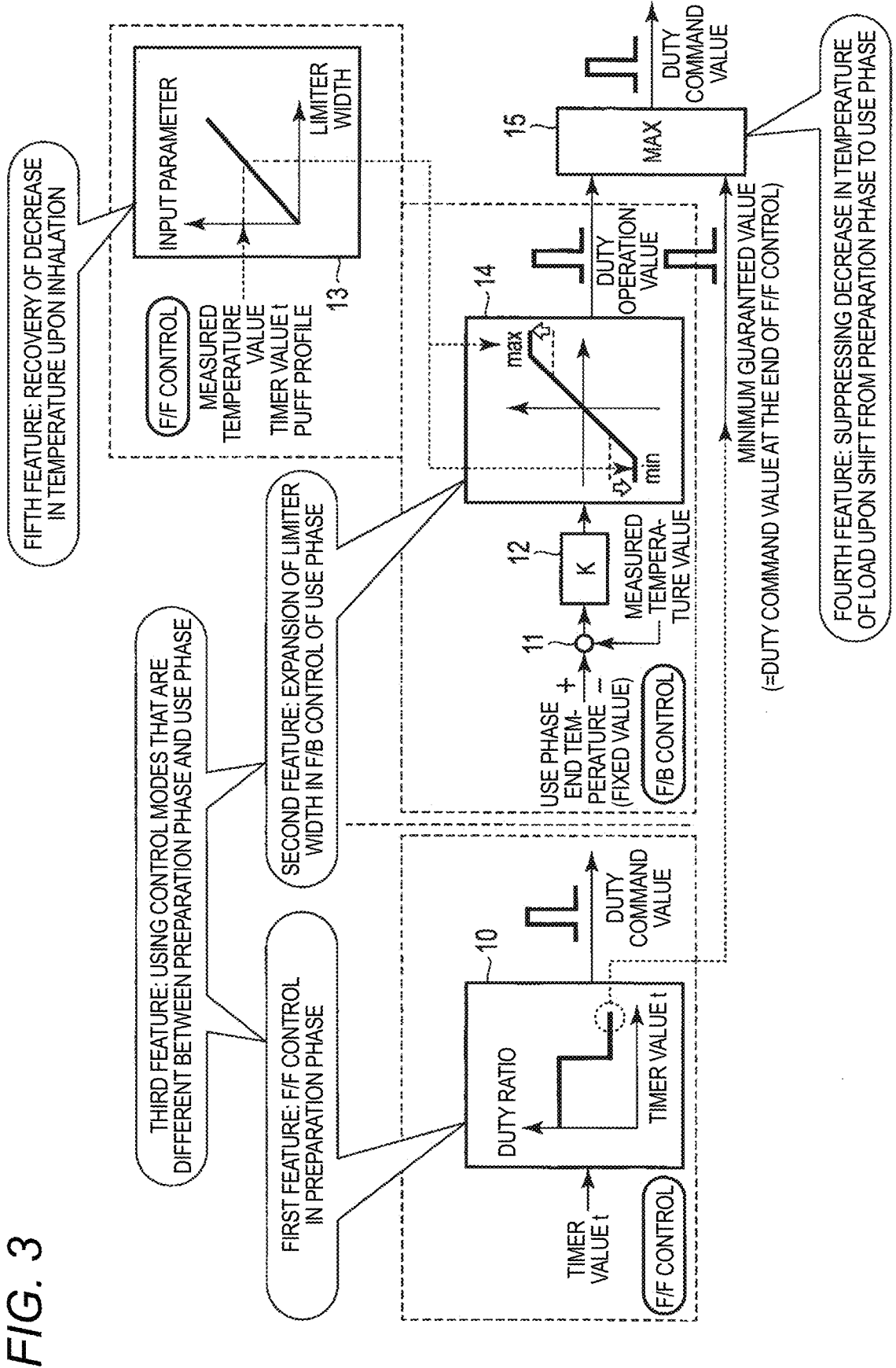
FIG. 3 is a control block diagram depicting an example of control that is executed by a control unit of the aerosol generation device in accordance with the embodiment.

FIG. 3 is a control block diagram depicting an example of control that is executed by the control unit 8 of the aerosol generation device 1 of the present embodiment.

The control unit 8 includes a preparation unit 10, a differential unit 11, a gain unit 12, a limiter change (adjusting) unit 13, a limiter unit 14, and a comparison unit 15. The constitutional elements of the control unit 8 will be specifically described later, respectively.

The control that is executed by the control unit 8 has mainly first to fifth features. The power that is supplied from the power source 4 to the load 3 is controlled by the control unit 8, so that it is possible to shorten a time of the preparation phase and to stabilize the amount of aerosol generation in the use phase.

The control unit 8 has a first feature of executing the feed-forward control in the preparation phase.

The control unit 8 has a second feature of expanding a limiter width of the limiter unit 14 in the feedback control in the use phase.

The control unit 8 has a third feature of using different control modes between the preparation phase and the use phase.

The control unit 8 has a fourth feature of suppressing decrease in temperature of the load 3 upon shift from the preparation phase to the use phase.

The control unit 8 has a fifth feature of recovering decrease in temperature when the user inhales aerosols in the use phase.

The aerosol generation device 1 of the present embodiment is configured to heat the aerosol generation article 9 by the load 3, for example, thereby generating aerosols from the aerosol generation article 9. The control unit 8 is configured to control the supply of power to the load 3 so that aerosols generated during the heating of the load 3 do not largely vary.

In order to implement the stable aerosol generation in one control mode or one control phase, it is necessary to change control parameters such as a target temperature over time, so that it may be difficult to perform the stable control.

In contrast, the control unit 8 of the present embodiment divides and uses the plurality of different control modes, specifically, the feed-forward control and the feedback control for heating of the load 3, thereby enabling the stable aerosol generation.

In the first to fifth embodiments to be described later, the first feature to the fifth feature will be specifically described.

In the present embodiment and the first to fifth embodiments, as an example, the feed-forward control and the feedback control may be configured as different control modes. The feed-forward control may be a control in which an operating amount of an operation target is not determined based on a control amount of a control target. In other words, the feed-forward control may be a control in which a control amount of a control target is not used as a feedback component, for example. As another example, the feed-forward control may also be a control in which a control amount of a control target is determined based on only a predetermined algorithm or variable or based on a combination of the predetermined algorithm or variable and any physical quantity acquired before outputting a control command relating to the operating amount to an operation target. The feedback control may be a control in which an operating amount of an operation target is determined based on a control amount of a control target, for example. In other words, the feedback control may be a control in which a control amount of a control target is used as a feedback component, for example. As another example, the feedback control may also be a control in which an operating amount of an operation target is determined based on a combination of any physical quantity acquired during execution of the control, in addition to a predetermined algorithm or variable.

In the first to third embodiments, the term "overheat" means a state in which a temperature of a control target is slightly higher than a temperature to be controlled (for example, the use phase end temperature or the target temperature). That is, it should be noted that it does not necessarily mean that the control target is in an excessively high-temperature state.

First Embodiment

In the first embodiment, the feed-forward control in the preparation phase is described.

The control unit 8 of the first embodiment controls the power that is supplied from the power source 4 to the load 3 by the feed-forward control when starting the supply of power to the load 3 in the non-operation state or when the load 3 is in the preparation state in which the load 3 cannot generate a predetermined amount or more of aerosols from an aerosol generation article. In this way, the temperature of the load 3 in the preparation state is increased by the feed-forward control, so that it is possible to speed up the increase in temperature of the load 3 until the load is in the use state.

The control unit 8 is configured to execute the feed-forward control so as to supply the load 3 with an amount of power necessary for the load 3 to shift from the non-operation state or the preparation state to the use state. In this way, the temperature of the load 3 is increased to the use state by the feed-forward control, so that it is possible to shorten a time necessary for the load 3 to be in the use state.

Herein, it is specifically described that the control unit 8 executes the feed-forward control so as to shorten a time until the load 3 is in the use state. For example, when the control unit 8 executes the feedback control to shift the load 3 in the non-operation state or in the preparation state to the use state, a control amount affects determination of an operating amount. Therefore, a time necessary for the load 3 to be in the use state is likely to lengthen. Particularly, in an aspect where the load 3 is subjected to the use state from a relatively early stage of the preparation phase by the feedback control, when a gain (transfer function) is small, a rate of temperature increase of the load 3 is slowed down, and when the gain is large, the load 3 is difficult to converge to the use state. Also, in an aspect where a target temperature of the load 3 is gradually increased over time by the feedback control in the preparation phase, when the measured temperature value of the load 3 reverses the target temperature, stagnation in temperature increase may occur. In contrast, when the control unit 8 executes the feed-forward control in the preparation phase, the concern, which occurs when the feedback control is used in the preparation phase as described above, does not occur. Therefore, it is possible to shorten the time until the load 3 is in the use state. For this reason, regarding the control that is executed by the control unit 8 so as to shift the load 3 in the non-operation state or in the preparation state to the use state, it can be said that the feed-forward control is more preferable than the feedback control.

The control unit 8 may be configured to execute the feed-forward control so as to suppress the power that is supplied from the power source 4 to the load 3, after supplying the necessary amount of power to the load 3. In this case, in order to suppress the power, for example, the power that is supplied to the load 3 so as to keep the temperature of the load 3 may be suppressed. In this way, after supplying the necessary amount of power to the load 3, the power that is supplied from the power source 4 to the load 3 is suppressed, so that the aerosol generation device 1 and the aerosol generation article 9 can be prevented from being overheated. In the meantime, if the aerosol generation device 1 is put in an overheated state, the lifetimes of the power source 4, the control unit 8, the load 3, a circuit for electrically connecting the power source 4 and the load 3, and the like of the aerosol generation device 1 may be reduced. Also, if the aerosol generation article 9 is put in the overheated state, the flavor and taste of aerosols generated by the aerosol generation article 9 may be impaired.

The control unit 8 may be configured to control the power that is supplied from the power source 4 to the load 3 by the feedback control, after supplying the necessary amount of power to the load 3. In this way, the feedback control is executed after the necessary amount of power is supplied to the load 3, so that it is possible to improve control accuracy after the necessary amount of power is supplied to the load 3 by the feedback control of which control stability is excellent, thereby stabilizing the aerosol generation.

The feed-forward control that is executed by the control unit 8 is divided into a first sub-phase and a second sub-phase, and values of variables that are used in the feed-forward control in the first sub-phase and the second sub-phase may be set different. In this case, the different values of variables may include different control variables, different constants and different threshold values. In this way, the feed-forward control is divided into the first sub-phase and the second sub-phase and the different values of variables are used, so that it is possible to improve the control accuracy, as compared to a case where one control phase is used. In the meantime, functions or algorithms that are used in the feed-forward control in the first sub-phase and the second sub-phase may be set different. The first sub-phase and the second sub-phase will be described in detail later with reference to FIGS. 4 to 8.

It is assumed that the first sub-phase is executed earlier than the second sub-phase, for example.

The power (W) or the amount of power (W·h) that is supplied to the load 3 in the first sub-phase may be set greater than the power (W) or the amount of power (W·h) that is supplied to the load 3 in the second sub-phase. Thereby, since a rate of temperature increase of the load 3 is gentle or the increase in temperature of the load 3 stops in the second sub-phase, it is possible to stabilize the temperature of the load 3 after the feed-forward control is over.

A time period of the first sub-phase may be set longer than a time period of the second sub-phase. In this way, the time of the first sub-phase in which the state (temperature) of the load 3 is dominantly changed is set longer than the second sub-phase, so that it is possible to resultantly shorten a total time period of the feed-forward control. In other words, the aerosol generation device 1 can more rapidly generate aerosols having desired flavor and taste from the aerosol generation article 9.

The control unit 8 may be configured to execute the feed-forward control so that the load 3 is in the use state at the end of the second sub-phase. Thereby, it is possible to stably make the temperature of the load 3 reach a temperature, which is necessary in the use state, by using the feed-forward control until the second sub-phase is over. Also, since an amount of power that is discharged by the power source 4 is reduced, as compared to a case where the load 3 is in the use state before the second sub-phase is over, it is possible to suppress deterioration in the power source 4, in addition to improving specific power consumption of the power source 4.

The control unit 8 may be configured to execute the feed-forward control so as to supply the power or the amount of power that is necessary so as to put the load 3 in the use state in which aerosols can be generated and to keep the use state of the load 3, in the second sub-phase. In this way, the power or the amount of power that is necessary so as to keep the use state in the second sub-phase is supplied to the load 3, so that it is possible to avoid the supply of extremely low power or extremely small amount of power in the second sub-phase. Therefore, it is possible to suppress situations where the load 3 is not in the use state, the aerosol generation device 1 cannot generate aerosols having desired flavor and taste from the aerosol generation article 9 in the use phase, and the specific power consumption of the power source 4 are lowered.

The control unit 8 may be configured to execute the feed-forward control so that be load 3 is in the use state, before the first sub-phase is changed to the second sub-phase. Thereby, it is possible to put the load 3 in the use state at the early stage at the time of the first sub-phase and to keep the use state by adjusting the temperature of the load 3 in the second sub-phase, which increase the control stability.

The control unit 8 may be configured to execute the feed-forward control so as to supply the power or the amount of power, which is necessary so as to keep the use state, to the load 3 that is in the use state, in the second sub-phase. Thereby, it is possible to suppress a situation where the extremely low power or extremely small amount of power is supplied in the second sub-phase and the load 3 is not thus put in the use state. As a result, it is possible to stabilize the load 3 in the use state. Also, it is possible to suppress variation in the temperature of the load 3 at the end of the second sub-phase.

The second sub-phase may be set shorter than the first sub-phase and equal to or longer than a unit time of control that is implemented (can be implemented) by the control unit 8, for example. Thereby, the second sub-phase is executed for an appropriate time period, so that it is possible to stabilize the temperature of the load 3.

The control unit 8 may be configured to change the values of variables that are used in the feed-forward control, based on an initial state that is a state during or before the execution of the feed-forward control of the load 3. In this case, the initial state includes an initial temperature and the like, for example. The change of the values of variables includes change of a control variable, change of a constant, and change of a threshold value. In this way, the values of variables that are used in the feedback control are changed based on the initial state, so that it is possible to suppress the variation in the temperature of the load 3 during execution and/or at the end of the teed-forward control, which may be caused due to external factors such as a product error, an initial condition, an atmospheric temperature and the like.

The control unit 8 may be configured to change the values of variables so as to supply the power or the amount of power, which is necessary for the load 3 in the initial state to shift to the use state, to the load 3. Thereby, it is possible to suppress the variation in the temperature of the load 3 in the use state at the end of the feedback control, which may be caused due to external factors such as a product error, an initial condition, an atmospheric temperature and the like.

The control unit 8 may be configured to acquire a value relating to a remaining amount of the power source 4, and to change the values of variables that are used in the feed-forward control, based on the value relating to the remaining amount during or before the execution of the feed-forward control. Thereby, it is possible to suppress the variation in the temperature of the load 3, which may be caused due to a difference in the remaining amount of the power source 4.

The control unit 8 may be configured to increase at least one of a duty ratio, a voltage, and an on-time of the power that is supplied from the power source 4 to the load 3 as the value relating to the remaining amount is smaller. For example, in a case where a DC/DC converter is used, a pulse wave may not be applied to the load 3 due to a smoothing action of a smoothing capacitor provided on an output-side of the DC/DC converter. Therefore, the control unit 8 may control a time (on-time) during which the power is supplied to the load 3, based on the value relating to the remaining amount. Thereby, it is possible to suppress the variation in the temperature of the load 3, which is caused due to a difference in the remaining amount of the power source 4.

The control unit 8 may be configured to change the values of variables so that a first amount of power, which is supplied from the power source 4 to the load 3 based on a value relating to a first remaining amount acquired from the power source 4, is substantially the same as a second amount of power, which is supplied from the power source 4 to the load 3 based on a value relating to a second remaining amount acquired from the power source 4 and different from the value relating to the first remaining amount. Thereby, for example, the PWM control can be executed so that the constant power is supplied to the load 3, irrespective of the remaining amount of the power source 4. As a result, it is possible to suppress the variation in the temperature of the load 3, which is caused due to a difference in the remaining amount of the power source 4.

The control unit 8 may be configured to acquire a value relating to a remaining amount of the power source 4, and to change the values of variables that are used in the feed-forward control, based on a state of the load 3 during or before the execution of the feed-forward control and the value relating to the remaining amount. Thereby, it is possible to suppress the variation in the temperature of the load 3 during the execution and/or at the end of the feed-forward control, which may be caused due to external factors such as a product error, an initial condition, an atmospheric temperature and the like, in addition to a difference in remaining amount of the power source 4.

The control unit 8 may be configured to decrease at least one of a duty ratio, a voltage, and an on-time of the power that is supplied from the power source 4 to the load 3 as the load 3 is closer to the use state in which the load can generate aerosols, and to decrease at least one of a duty ratio, a voltage, and an on-time of the power as the value relating to the remaining amount is larger, based on the state of the load 3. In this case, for example, at least one of a duty ratio, a voltage, and an on-time of the power obtained from the state of the load 3 such as an initial temperature can be corrected with the remaining amount of the power source 4, so that it is possible to suppress the variation in the temperature of the load 3 during the execution and/or at the end of the feed-forward control, which may be caused the remaining amount of the power source 4, in addition to the external factors such as a product error, an initial condition, an atmospheric temperature and the like.

The control unit 8 may be configured to change the duty ratio, the voltage and the on-time so that a first amount of power, which is supplied from the power source 4 to the load 3 based on a value relating to a first remaining amount acquired from the power source 4, is substantially the same as a second amount of power, which is supplied from the power source 4 to the load 3 based on a value relating to a second remaining amount acquired from the power source 4 and different from the value relating to the first remaining amount. In this case, the first amount of power and the second amount of power may be set different depending on the state of the load 3. Thereby, for example, the PWM control can be executed so that the same power in terms of the first remaining amount and the second remaining amount is supplied to the load 3. As a result, it is possible to suppress the variation in the temperature of the load 3 during execution and/or at the end of the feed-forward control, which may be caused due to the remaining amount of the power source 4, in addition to the external factors such as a product error, an initial condition, an atmospheric temperature and the like.

The control unit 8 may be configured to change the values of variables that are used in the feed-forward control, based on a resistance value of the load 3 or a deterioration state in the load 3 during or before the execution of the feed-forward control. In this case, the control unit 8 may be configured to obtain the deterioration state, based on the number of uses or a cumulative value of use times of the load 3, for example. Thereby, even when the load 3 is deteriorated and thus the electric resistance value at room temperatures and the like changes as the number of uses of the aerosol generation device 1 increases, the temperature of the load 3 can be stabilized. Also, even when the load 3 having a positive temperature coefficient characteristic (PTC characteristic) is used and the load 3 is deteriorated and the characteristic thereof changes, the temperature of the load 3 can be stabilized.

The diverse controls by the control unit 8 may also be implemented as the control unit 8 executes a program.

Regarding the first embodiment, specific control examples are further described in following embodiments 1A to 1E.

Example 1A

Figure 4:
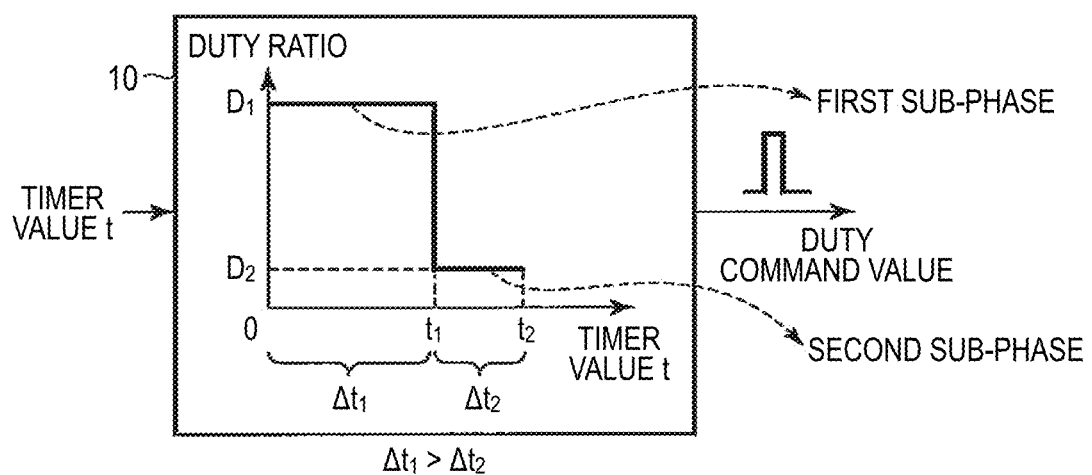
FIG. 4 is a control block diagram depicting an example of control that is executed by the control unit in accordance with Example 1A.

FIG. 4 is a control block diagram depicting an example of control that is executed by the control unit 8 in accordance with Example 1A.

Figure 9:
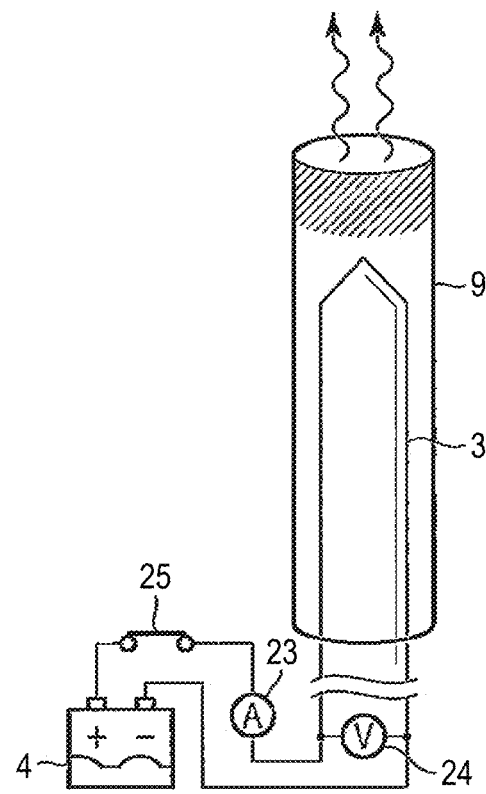
FIG. 9 depicts an example of a relation between current that flows from a power source to a load and a voltage that is applied to the load by the power source.

The preparation unit 10 of the control unit 8 acquires the timer value t that is output by the timer 5 and obtains a duty command value corresponding to the timer value t, in the preparation phase. The control unit 8 switches a switch 25 provided in a circuit for electrically connecting the load 3 and the power source 4, as shown in FIG. 9, according to the obtained duty command value, thereby controlling the power that is supplied to the load 3, based on the duty command value.

In Example 1A, a heating state for the load 3 is switched based on the duty command value, more specifically, the duty ratio indicated by the duty command value. However, when controlling a DC/DC converter provided in the circuit for electrically connecting the load 3 and the power source 4, instead of the switch 25, the heating state for the load 3 may be switched based on the current that is supplied to the load 3, the voltage that is applied to the load 3 or command values thereof, for example, and a value for instructing the heating state for the load 3 may be changed as appropriate.

The preparation phase further includes the first sub-phase and the second sub-phase. The first sub-phase and the second sub-phase may also be distinguished by the duty command value, more specifically, the duty ratio indicated by the duty command value. Also, the first sub-phase and the second sub-phase may be distinguished by the current that is supplied to the load 3, the voltage that is applied to the load 3 or command values thereof.

A time period $\Delta t_1$ of the first sub-phase is a time period from start of the supply of power to the load 3 in the non-operation state to time $t_1$.

A time period $\Delta t_2$ of the second sub-phase is a time period from time $t_1$ to end time $t_2$ of the preparation phase.

The time period $\Delta t_1$ of the first sub-phase is longer than the time period $\Delta t_2$ of the second sub-phase.

A duty ratio $D_1$ in the first sub-phase is greater than a duty ratio $D_2$ in the second sub-phase. In Example 1A, the power that is supplied from the power source 4 to the load 3 is set greater as the duty ratio increases. Therefore, the power that is supplied from the power source 4 to the load 3 in the first sub-phase is greater than the power that is supplied from the power source 4 to the load 3 in the second sub-phase.

In the first sub-phase, the control unit 8 controls the power that is supplied to the load 3, based on the duty command value indicative of a large duty ratio, until the temperature of the load 3 (aerosol generation article 9) reaches an aerosol generation temperature. Thereby, it is possible to generate aerosols from the aerosol generation article 9 at the early stage from start of the supply of power (power feeding) from the power source 4 to the load 3.

In the second sub-phase, the control unit 8 controls the power that is supplied to the load 3, based on a duty command value indicative of the duty ratio smaller than the duty ratio of the first sub-phase, so as to suppress variation in the temperature of the load 3 until the load shifts to the use phase, and to keep the temperature of the load 3 (aerosol generation article 9) to the aerosol generation temperature or higher. Even when a temperature at the end of the first sub-phase slightly varies, the control unit 8 suppresses and absorbs the variation by the control in the second sub-phase. Thereby, the flavor and taste of aerosols that are generated from the aerosol generation article 9 in the use phase become stable.

In this way, in the preparation phase, the high power is supplied to the load 3 to quickly increase the temperature of the load 3 by the first sub-phase and the low power for heat retention is supplied to the load 3 by the second sub-phase, so that it is possible to stabilize the amount of aerosol generation and the flavor and taste thereof in the use phase after the preparation phase.

Figure 5:
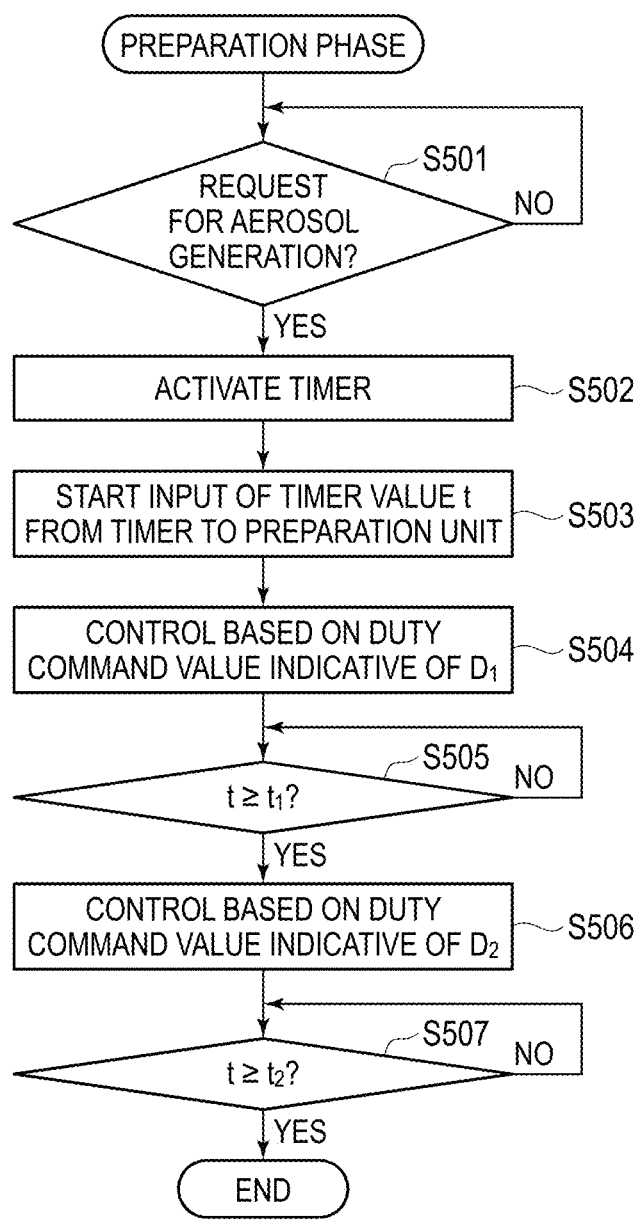
FIG. 5 is a flowchart depicting an example of processing in a preparation phase by the control unit in accordance with Example 1A.

FIG. 5 is a flowchart depicting an example of processing in the preparation phase by the control unit 8 in accordance with Example 1A.

In step S501, the preparation unit 10 determines whether there is a request for aerosol generation. When it is determined that there is no request for aerosol generation ("No" in step S501), the preparation unit 10 repeats step S501. As a first example, the preparation unit 10 may determine in step S501 whether there is a request for aerosol generation, based on whether an input for starting heating of the load 3 is made from a user. More specifically, when an input for starting heating of the load 3 is made from a user, the preparation unit 10 may determine that there is a request for aerosol generation. On the other hand, when an input for starting heating of the load 3 is not made from a user, the preparation unit 10 may determine that there is no request for aerosol generation. As a second example, the aerosol generation device 1 has a sensor for detecting user's inhalation, which is not shown in FIG. 1, and may use user's inhalation detected by the sensor, as an input for starting heating of the load 3. As a third example, the aerosol generation device 1 has at least one of a button, a switch, a touch panel and a user interface, which are not shown in FIG. 1, and may use an operation thereon, as an input for starting heating of the load 3.

When it is determined that there is a request for aerosol generation, the preparation unit 10 activates the timer 5, in step S502.

In step S503, an input of the timer value t from the timer 5 to the preparation unit 10 starts.

In step S504, the preparation unit 10 switches the switch 25 provided in the circuit for electrically connecting the load 3 and the power source 4, which is shown in FIG. 9, based on the duty command value indicative of the duty ratio $D_1$ in the first sub-phase, thereby controlling the power that is supplied to the load 3.

In step S505, the preparation unit 10 determines whether the timer value t is the end time $t_1$ or longer of the first sub-phase. When it is determined that the timer value t is not the end time $t_1$ or longer of the first sub-phase (a determination result in step S505 is "No"), the preparation unit 10 repeats step S505.

When it is determined that the timer value t is the end time $t_1$ or longer of the first sub-phase (a determination result in step S505 is "Yes"), the preparation unit 10 controls the power that is supplied to the load 3, based on the duty command value indicative of the duty ratio $D_2$ in the second sub-phase, in step S506.

In step S507, the preparation unit 10 determines whether the timer value t is the end time $t_2$ or longer of the second sub-phase. When it is determined that the timer value t is not the end time $t_2$ or longer of the second sub-phase (a determination result in step S507 is "No"), the preparation unit 10 repeats step S507. When it is determined that the timer value t is the end time $t_2$ or longer of the second sub-phase (a determination result in step S507 is "Yes"), the preparation unit 10 ends the preparation phase and shifts to the use phase.

In Example 1A as described above, the control unit 8 controls the heating of the load 3 by using the feed-forward control in the preparation phase. Therefore, after there is a request for aerosol generation and the supply of power from the power source 4 to the load 3 starts, it is possible to increase the rate of temperature increase of the load 3.

In Example 1A, in the preparation phase, the feed-forward control increases the temperature of the load 3 to a temperature at which aerosols can be inhaled. Therefore, it is possible to shorten a time after the aerosol generation is requested until the user can inhale aerosols.

In Example 1A, since the power that is supplied to the load 3 in the first sub-phase of the preparation phase is once increased and then the power that is supplied to the load 3 in the second sub-phase of the preparation phase is lowered, it is possible to suppress the load 3 from being overheated.

The control unit 8 controls the heating of the load 3 by using the feed-forward control in the preparation phase, so that it is possible to increase the rate of temperature increase of the load 3 after there is a request for aerosol generation and the supply of power from the power source 4 to the load 3 starts, it is possible to shorten a time after the aerosol generation is requested until the user can inhale aerosols and it is possible to suppress the load 3 from being overheated. Herein, the reasons are described in detail. For example, if the control unit 8 controls the heating of the load 3 by using the feedback control in the preparation phase, a control amount affects a decision of the operating amount, so that the rate of temperature increase of the load 3 is likely to be slow. Also, due to the similar reason, the time after the aerosol generation is requested until the user can inhale aerosols is likely to lengthen. In particular, in an aspect where the load 3 is heated to the temperature at which aerosols can be generated from a relatively early stage of the preparation phase, when a gain is small, the rate of temperature increase of the load 3 is slow, and when the gain is large, the temperature of the load 3 is difficult to converge to the temperature at which aerosols can be generated, so that the load 3 is likely to be overheated. Also, in an aspect where the target temperature of the load 3 is gradually increased over time, stagnation in temperature increase may occur when the measured temperature value of the load 3 reverses the target temperature. However, when the control unit 8 controls the heating of the load 3 by using the teed-forward control in the preparation phase, the concerns do not occur. Therefore, it is possible to increase the rate of temperature increase of the load 3 after there is a request for aerosol generation and the supply of power from the power source 4 to the load 3 starts. Also, it is possible to shorten a time after the aerosol generation is requested until the user can inhale aerosols. In addition to this, it is possible to suppress the load 3 from being overheated, and to shorten a time until the load 3 is in the use state. Therefore, it can be said that the feed-forward control is more preferable than the feedback control, as the control that is used for the heating of the load 3 in the preparation phase.

Example 1B

In Example 1B, control of changing the power that is supplied to the load 3 in the first sub-phase on the basis of the measured temperature value indicative of the temperature of the load 3 is described.

Figure 6:
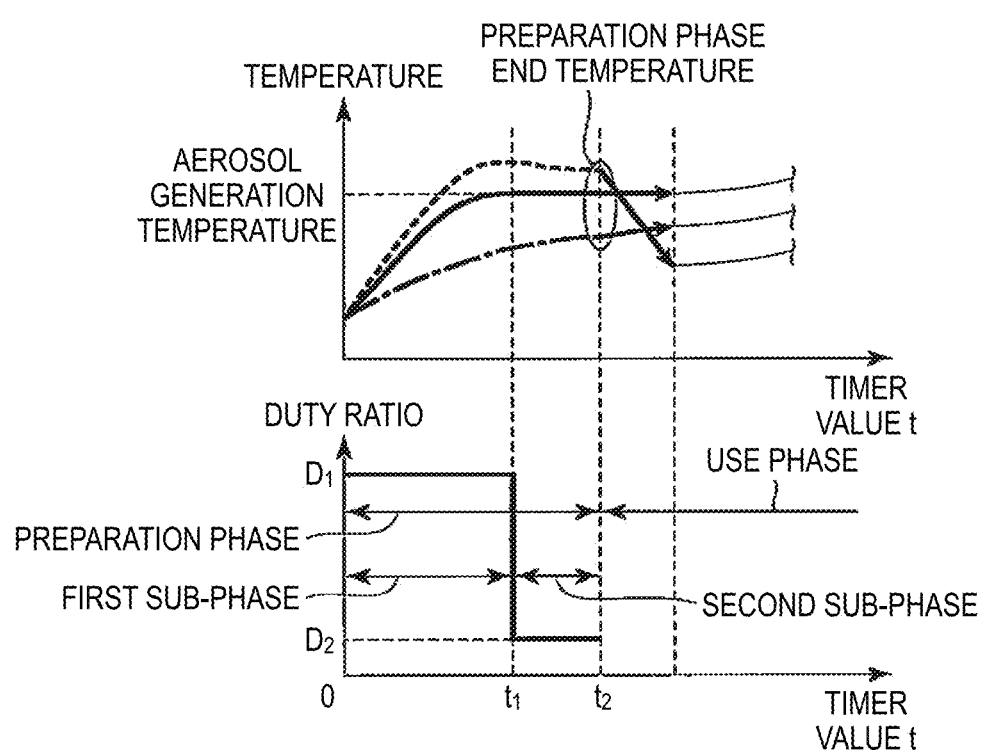
FIG. 6 is a graph depicting an example of a state in which a temperature of the load is uneven between the preparation phase and a use phase.
Figure 7:
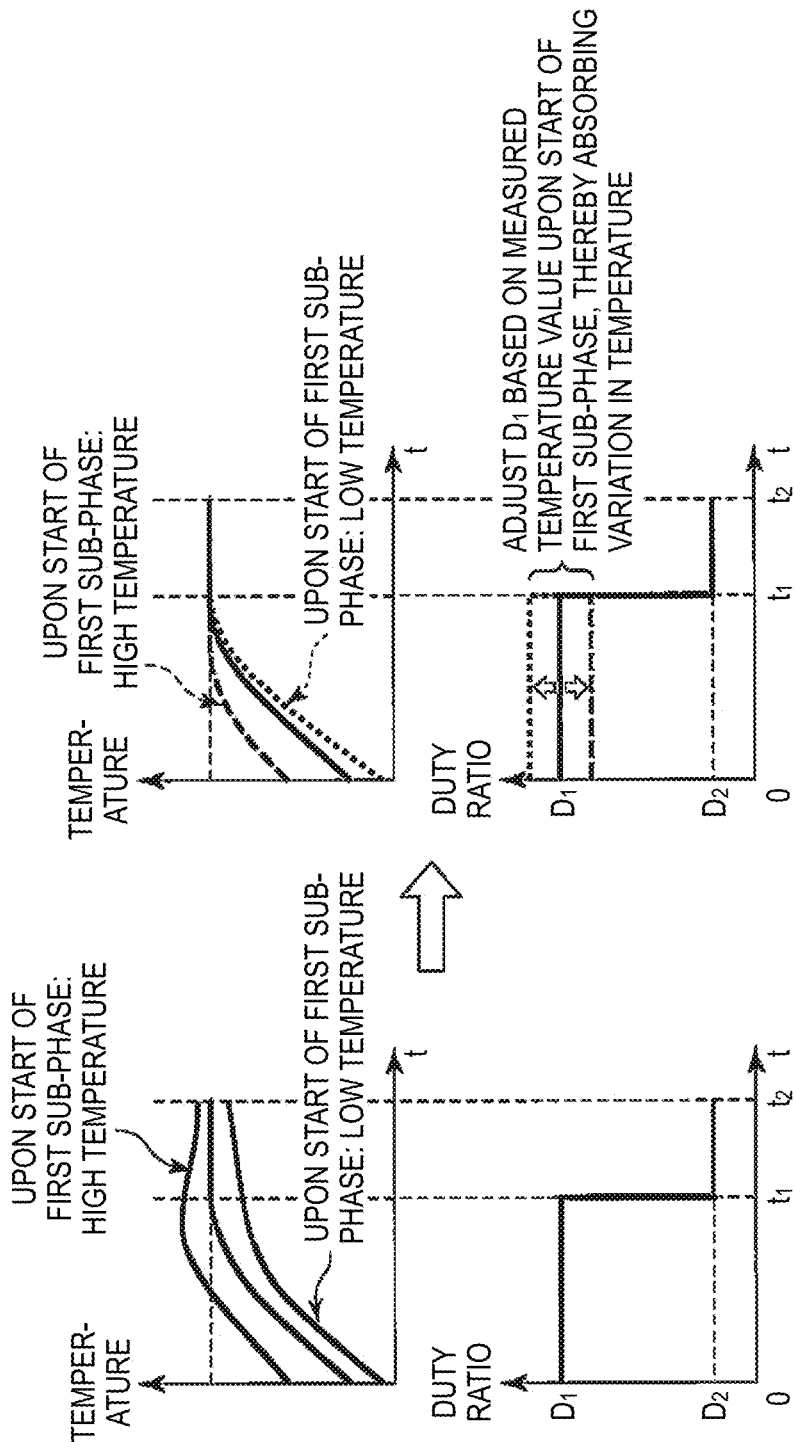
FIG. 7 is a graph depicting an example of control on a duty ratio in a first sub-phase.
Figure 8:
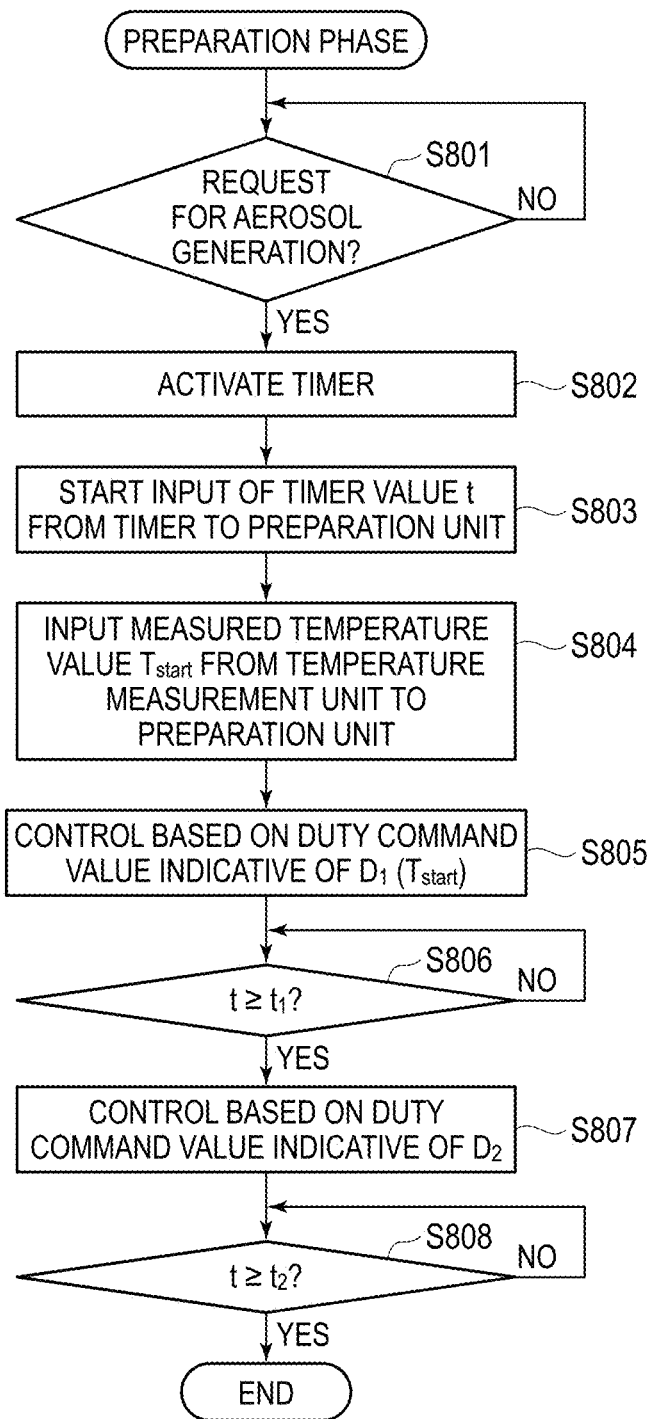
FIG. 8 is a flowchart depicting an example of processing in the preparation phase by the control unit in accordance with Example 1B.

FIG. 6 is a graph depicting an example of a state in which a temperature of the load is uneven between the preparation phase and the use phase. FIG. 6 is a graph depicting an example of a relation between the timer value t and the temperature of the load 3 and a relation between the timer value t and the power that is supplied from the power source 4 to the load 3. The horizontal axis indicates the timer value t. The vertical axis indicates the temperature of the load 3 or the duty ratio of the power that is supplied to the load 3.

Even though the preparation phase is over, the temperature of the load 3 may rapidly vary from the preparation phase end temperature when the load shifts from the preparation phase to the use phase or immediately after the shift to the use phase.

When the preparation phase end temperature is not stable at or near the aerosol generation temperature, the temperature of the load 3 shows the sharp variation, so that the temperature of the load 3 may not reach the aerosol generation temperature at least at the early stage of the use phase.

As factors that cause the temperature of the load 3 to vary when the preparation phase is over, three following factors may be assumed, for example.

A first factor is a shift in the initial state of the load 3, for example, a shift in the temperature of the load 3 at the time when the temperature increase of the load 3 starts.

A second factor is a shift in the output voltage of the power source 4, which can be caused due to reduction in the remaining amount or deterioration of the power source 4.

A third factor is a product error of the aerosol generation article 9 or the aerosol generation device 1.

The first and second factors can be at least relaxed by performing following control the first sub-phase.

The third factor can be at least relaxed by heat-retention control in the second sub-phase.

FIG. 7 is a graph depicting an example of control on the duty ratio $D_1$ in the first sub-phase. FIG. 7 depicts a relation between the timer value t and the temperature of the load 3, and a relation between the timer value t and the duty ratio. The horizontal axis indicates the tinier value t. The vertical axis indicates the temperature of the load 3 or the duty ratio of the power that is supplied to the load 3.

If the duty ratio $D_1$ in the first sub-phase is set constant and the duty ratio $D_2$ in the second sub-phase is set constant, when the temperature of the load 3 is low or high at the start of the first sub-phase, the temperature of the load 3 is also low or high at the end of the second sub-phase and the temperature of the load 3 varies at the end of the preparation phase.

In contrast, the control unit 8 in accordance with Example 1B changes the duty ratio $D_1$ in the first sub-phase, based on the measured temperature value at the start of the first sub-phase, thereby suppressing the variation in the temperature of the load 3 at the end of the preparation phase, based on the shift in the temperature of the load 3 at the start of the first sub-phase.

More specifically, when the measured temperature value at the start of the first sub-phase is small, the control unit 8 increases the duty ratio $D_1$ in the first sub-phase. In contrast, when the measured temperature value at the start of the first sub-phase is large, the control unit 8 decreases the duty ratio $D_1$ in the first sub-phase.

FIG. 8 is a flowchart depicting an example of processing in the preparation phase by the control unit 8 in accordance with Example 1B.

The processing from step S801 to step S803 is the same as the processing from step S501 to step S503 in FIG. 5.

In step S804, a measured temperature value $T_{start}$ at the start of the first sub-phase is input, as the initial state, from the temperature measurement unit 6 to the preparation unit 10.

In step S805, the preparation unit 10 obtains the duty ratio $D_1$ ($T_{start}$) in the first sub-phase, based on the measured temperature value $T_{start}$, and switches the switch 25 provided in the circuit for electrically connecting the load 3 and the power source 4, as shown in FIG. 9, based on the duty command value indicative of the duty ratio $D_1$ ($T_{start}$) in the first sub-phase, thereby controlling the power that is supplied to the load 3.

The processing from step S806 to step S808 is the same as the processing from step S505 to step S507 in FIG. 5.

In Example 1B as described above, it is possible to suppress the variation in temperature of the load 3 at the end of the preparation phase, based on the shift in temperature of the load 3 at the start of the first sub-phase, so that it is possible to stabilize the amount of aerosol generation and the favor and taste thereof in the use phase after the preparation phase.

In Example 1B, the control unit 8 changes the duty command value in the first sub-phase, based on the measured temperature value $T_{start}$ at the start of the first sub-phase. However, the control unit 8 may change the duty command value in the second sub-phase based on the measured temperature value $T_{start}$, or may change both the duty command value in the first sub-phase and the duty command value in the second sub-phase, based on the measured temperature value $T_{start}$.

Example 1C

In Example 1C, control of changing the power in the first sub-phase based on the SOC of the power source 4 as an example of the value relating to the remaining amount of the power source 4 or PWM control of making the voltage applied to the load 3 constant even when the SOC of the power source 4 changes is described.

FIG. 9 depicts an example of a relation between current that flows from the power source 4 to the load 3 and a voltage that is applied to the load 3 by the power source 4. An ammeter 23 outputs current A that flows from the power source 4 to the load 3, and a voltmeter 24 outputs a voltage V that is applied from the power source 4 to the load 3. Also, the control unit 8 (not shown in FIG. 9) acquires a value output from the ammeter 23 and a value output from the voltmeter 24. In the meantime, as the ammeter 23 and the voltmeter 24, an ammeter and a voltmeter each having a shunt resistor having a known resistance value embedded therein may be used or a Hall element may be used. In the meantime, it is advantageous to use those in which a shunt resistor is embedded, from a standpoint of a weight or volume, and to use the Hall element, from a standpoint of measurement accuracy or less affecting a measurement target. Also, the ammeter 23 or the voltmeter 24 may output a measured value as a digital value or an analog value. When the ammeter 23 or the voltmeter 24 outputs an analog value, the control unit 8 may convert the analog value into a digital value by an A/D converter.

Also, the power source 4 and the load 3 are electrically connected by the circuit, so that when the control unit 8 opens/closes (switches) the switch 25 provided in the circuit, the supply of power from the power source 4 to the load 3 is controlled. As an example, the switch 25 may consist of at least one of a switch, a contactor and a transistor. In the meantime, the circuit may also have a DC/DC converter, instead of the switch 25 or in addition to the switch 25. In this case, the control unit 8 controls the DC/DC converter, thereby controlling the supply of power from the power source 4 to the load 3.

In FIG. 9, the voltmeter 24 is provided closer to the load 3 than the switch 25. However, in order to use the SOC-OCV method so as to acquire the SOC of the power source 4, other voltmeter may be provided closer to the power source 4 than the switch 25. The other voltmeter enables an output of an open end voltage (OCV) of the power source 4.

Figure 10:
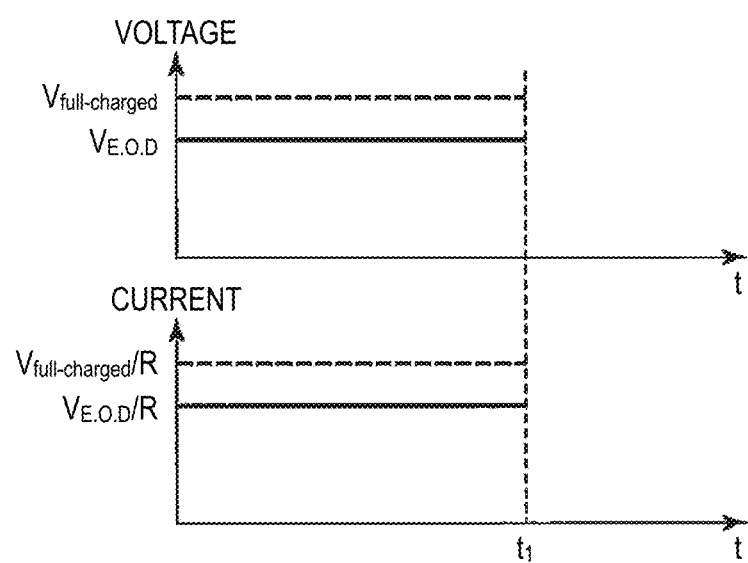
FIG. 10 is a graph depicting an example of relations of a full-charged voltage, a discharge-end voltage, a current corresponding to the full-charged voltage and a current corresponding to the discharge-end voltage in the first sub-phase of the preparation phase.

FIG. 10 is a graph depicting an example of a relation between an output voltage and an output current corresponding to the remaining amount of the power source 4 in the first sub-phase of the preparation phase. In FIG. 10, the horizontal axis indicates the tinier value t, and it should be noted that the second sub-phase after time $t_1$ is omitted. The vertical axis indicates the voltage or current that is output from the power source 4. Also, in FIG. 10, the broken line indicates the voltage and current when the remaining amount of the power source 4 is 100%. The solid line indicates the voltage and current when the discharge-end voltage or a voltage close to the discharge-end voltage is output because the remaining amount of the power source 4 is at or near 0%. In FIG. 10, $V_{full-charged}$ and Wan indicate the full-charged voltage and the discharge-end voltage of the power source 4, respectively.

In FIG. 10, it is assumed that the duty ratio $D_1$ in the first sub-phase is 100%.

For simplification, when it is assumed that the electric resistance of the circuit for electrically connecting the load 3 and the power source 4 is negligibly small and the circuit is not a target that the power source 4 supplies power at the same time with the load 3, the output current corresponding to the remaining amount of the power source 4 is obtained by dividing the output voltage of the power source 4 by a resistance value R of the load 3.

The current $I_{full-charged}$ that is output when the output voltage of the power source 4 is the full-charged voltage is obtained by the full-charged voltage/the resistance of the load 3 ($V_{full-charged}/R$), when the simplified model as described above is used.

The current $I_{E.O.D}$ that is output when the Output voltage of the power source 4 is the discharge-end voltage is obtained by the discharge-end voltage/the resistance of the load 3 ($V_{E.O.D}/R$), when the simplified model as described above is used.

In the first sub-phase of the preparation phase, the current $V_{full-charged}/R$ that is output when the output voltage of the power source 4 is the full-charged voltage $V_{full-charged}$ is greater than the current $V_{E.O.D}/R$ that is output when the output voltage of the power source 4 is the discharge-end voltage $V_{E.O.D}$.

Figure 11:
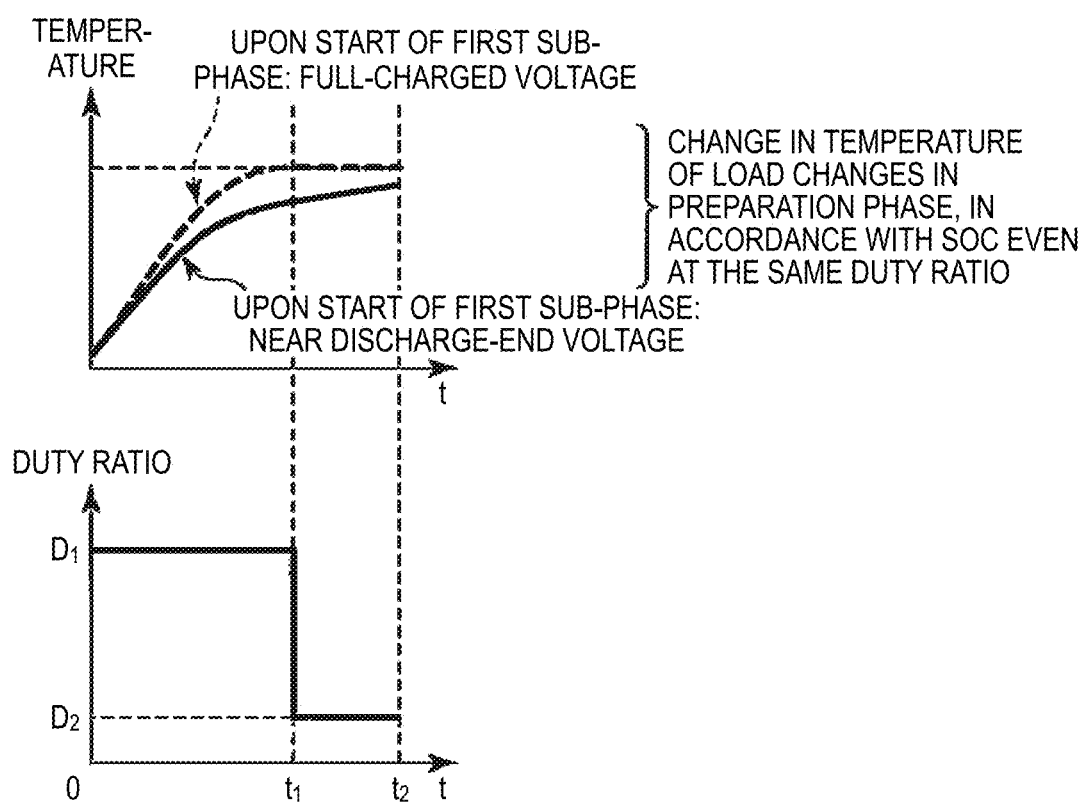
FIG. 11 is a graph depicting an example of comparison between a change in temperature of the load in the preparation phase when a voltage of the power source is a full-charged voltage at the start of the first sub-phase and a change in temperature of the load in the preparation phase when a voltage of the power source is near the discharge-end voltage at the start of the first sub-phase, in a case where a duty ratio is constant.

FIG. 11 is a graph depicting an example of comparison between a change in temperature of the load 3 in the preparation phase when a voltage of the power source 4 is the full-charged voltage at the start of the first sub-phase and a change in temperature of the load 4 in the preparation phase when a voltage of the power source 4 is near the discharge-end voltage at the start of the first sub-phase, in a case where the duty ratio is constant. In FIG. 11, the horizontal axis indicates the timer value t. The vertical axis indicates the temperature or the duty ratio of the power that is supplied to the load 3. As described above, the current that is supplied from the power source 4 to the load 3 and the voltage that is applied when the power source 4 is near the discharge-end voltage are smaller, as compared to a case where the power source 4 is at the full-charged voltage. Therefore, the change in temperature of the load 3 in the preparation phase when the power source 4 is at the full-charged voltage is larger than the change in temperature of the load 3 in the preparation phase when the power source 4 is near the discharge-end voltage.

In the meantime, when the power source 4 is at the full-charged voltage, the power that is supplied from the power source 4 to the load 3 in the first sub-phase is expressed by a following equation.

$$W=(V_{full-charged} \cdot D)^2/R$$

On the other hand, when the power source 4 is near the discharge-end voltage, the power that is supplied from the power source 4 to the load 3 in the first sub-phase is expressed by a following equation.

$$W=(V_{E.O.D} \cdot D)^2/R$$

In both the equations, D indicates the duty ratio of the power that is supplied to the load 3.

A difference between both the equations is obtained. A difference between the power that is supplied from the power source 4 to the load 3 in the first sub-phase when the power source 4 is at the full-charged voltage and the power that is supplied from the power source 4 to the load 3 in the first sub-phase when the power source 4 is near the discharge-end voltage is expressed by a following equation.

$$\Delta W=\{(V_{full-charged} \cdot D)^2-(V_{E.O.D} \cdot D)^2\}/R$$

For example, when the full-charged voltage $V_{full-charged}$ is 4.2V, the discharge-end voltage $V_{E.O.D}$ is 3.2V, the electric resistance value R of the load 3 is 1.0Ω and the duty ratio D is 100%, the power difference ΔW is 7.4 W.

For this reason, even when diverse conditions such as a condition (for example, a contact area and the like) relating to heat transfer between the load 3 and the aerosol generation article 9, an initial temperature of the load 3, a heat capacity of the aerosol generation article 9 and the like are the same, the temperature of the load 3 at the end of the preparation phase changes according to the remaining amount of the power source 4.

Therefore, in Example 1C, the control unit 8 changes the power in the first sub-phase, i.e., the duty ratio, based on the output voltage of the power source 4, thereby suppressing the variation in temperature of the load 3 at the end of the preparation phase.

Also, in Example 1C, the control unit 8 may execute the PWM control of making the voltage to be applied to the load 3 constant so as to exclude the influence of the output voltage of the power source 4. In the PWM control, a pulsed voltage waveform is changed so that an area of an effective voltage waveform is the same. Herein, the effective voltage can be obtained from "applied voltage×duty ratio". In another example, the effective voltage may be obtained from a root mean square (RMS).

Figure 12:
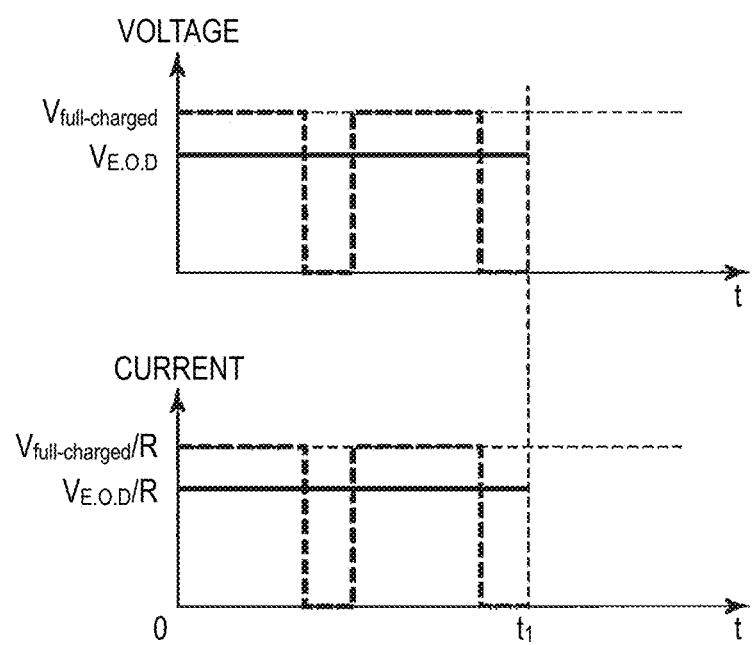
FIG. 12 is a graph exemplifying a relation between the full-charged voltage and the discharge-end voltage implemented by PWM control and a relation between a current corresponding to the full-charged voltage and a current corresponding to the discharge-end voltage.

FIG. 12 is a graph exemplifying a relation between the output voltage and the output current of the power source 4 when the PWM control is performed according to the remaining amount of the power source 4. In FIG. 12, the horizontal axis indicates the timer value t, and it should be noted that the second sub-phase after time $t_1$ is omitted. The vertical axis indicates the voltage or current that is output from the power source 4.

In the preparation phase, the control unit 8 performs control so that an area of a pulsed voltage waveform corresponding to the full-charged voltage $V_{full-charged}$ is the same as an area of a voltage waveform corresponding to the discharge-end voltage $V_{E.O.D}$.

The equation (1) indicates a relation among the duty ratio $D_{full-charged}$ corresponding to the full-charged voltage $V_{full-charged}$, the full-charged voltage $V_{full-charged}$, the discharge-end voltage $V_{E.O.D}$, and the duty ratio $D_{E.O.D}$ corresponding to the discharge-end voltage $V_{E.O.D}$.

[equation 1]

$$D_{full\_charged} = \frac{V_{E.O.D} \cdot D_{E.O.D}}{V_{full\_charged}} = \frac{3.2 \times 100\%}{4.2} \cong 0.76 \quad (1)$$

In the equation (1), when the duty ratio $D_{E.O.D}$ all corresponding to the discharge-end voltage $V_{E.O.D}$ is set to 100%, the duty ratio $D_{full\_charged}$ corresponding to the full-charged voltage $V_{full\_charged}$ is 76%.

In this way, the control unit 8 can suppress the variation in temperature of the load 3 at the end of the preparation phase by controlling the duty ratio based on the output voltage of the power source 4 in the first sub-phase included in the preparation phase.

Figure 13:
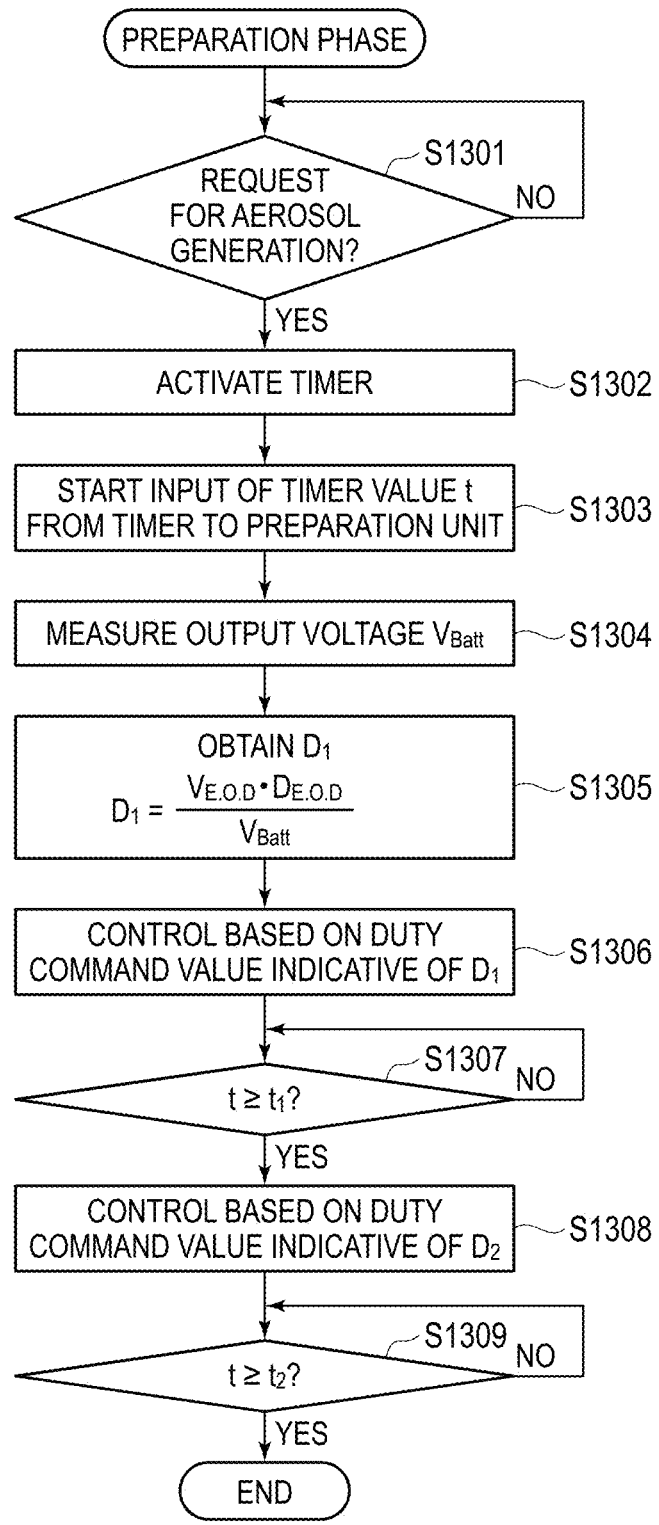
FIG. 13 is a flowchart depicting an example of processing in the preparation phase by the control unit in accordance with Example 1C.

FIG. 13 is a flowchart depicting an example of processing in the preparation phase by the control unit 8 in accordance with Example 1C.

The processing from step S1301 to step S1303 is the same as the processing from step S501 to step S503 in FIG. 5.

In step S1304, the power source measurement unit 7 measures the output voltage (battery voltage) $V_{Batt}$ of the power source 4.

In step S1305, the preparation unit 10 obtains the duty ratio $D_1 = (V_{E.O.D} \cdot D_{E.O.D})/V_{Batt}$.

In step S1306, the preparation unit 10 switches the switch 25 provided in the circuit for electrically connecting the load 3 and the power source 4, as shown in FIG. 9, based on the duty command value indicative of the duty ratio $D_1$, thereby controlling the power that is supplied to the load 3.

The processing from step S1307 to step S1309 is the same as the processing from step S505 to step S507 in FIG. 5.

In Example 1C as described above, the duty ratio $D_1$ in the first sub-phase included in the preparation phase is changed according to the output voltage of the power source 4 that is an example of the value relating to the remaining amount of the power source 4, so that the variation in temperature of the load at the end of the preparation phase can be suppressed. Therefore, it is possible to stabilize the amount of aerosol generation and the flavor and taste in the use phase after the preparation phase.

In Example 1C, the aspect where the output voltage of the power source 4 is used as an example of the value relating to the remaining amount of the power source 4 has been described. Instead, the duty ratio $D_1$ in the first sub-phase included in the preparation phase may be changed according to the SOC of the power source 4, as another example of the value relating to the remaining amount of the power source 4.

In the case where the SOC is used as the value relating to the remaining amount of the power source 4, the SOC is defined as 100% when the voltage of the power source 4 is the full-charged voltage, as well known. On the other hand, the SOC is defined as 0% when the voltage of the power source 4 is the discharge-end voltage. Also, the SOC changes continuously from 100% to 0% according to the remaining amount of the power source 4. When a lithium-ion secondary battery is used as the power source 4, the full-charged voltage and the discharge-end voltage are 4.2V and 3.2V, respectively, for example. However, the full-charged voltage and the discharge-end voltage of the power source 4 are not limited thereto. As described above, the control unit 8 may obtain the SOC of the power source 4 by the SOC-OCV method, the current integration method (Coulomb counting method) or the like.

Example 1D

In order to control the temperature of the load 3 at the end of the preparation phase with higher accuracy, the control is preferably performed based on a plurality of initial conditions, for example, both values relating to the temperature of the load 3 and the remaining amount of the power source 4.

In Example 1D, the feed-forward control of obtaining the duty ratio $D_{E.O.D}(T_{HTR})$ corresponding to the discharge-end voltage $V_{E.O.D}$, based on the measured temperature value $T_{HTR}$, obtaining the duty ratio $D_1$ in the first sub-phase, based on the discharge-end voltage $V_{E.O.D}$, the duty ratio $D_{E.O.D}(T_{HTR})$, and the battery voltage $V_{Batt}$, and switching the switch 25 provided in the circuit for electrically connecting the load 3 and the power source 4 as shown in FIG. 9 by using the duty ratio $D_1$ is performed.

Figure 14:
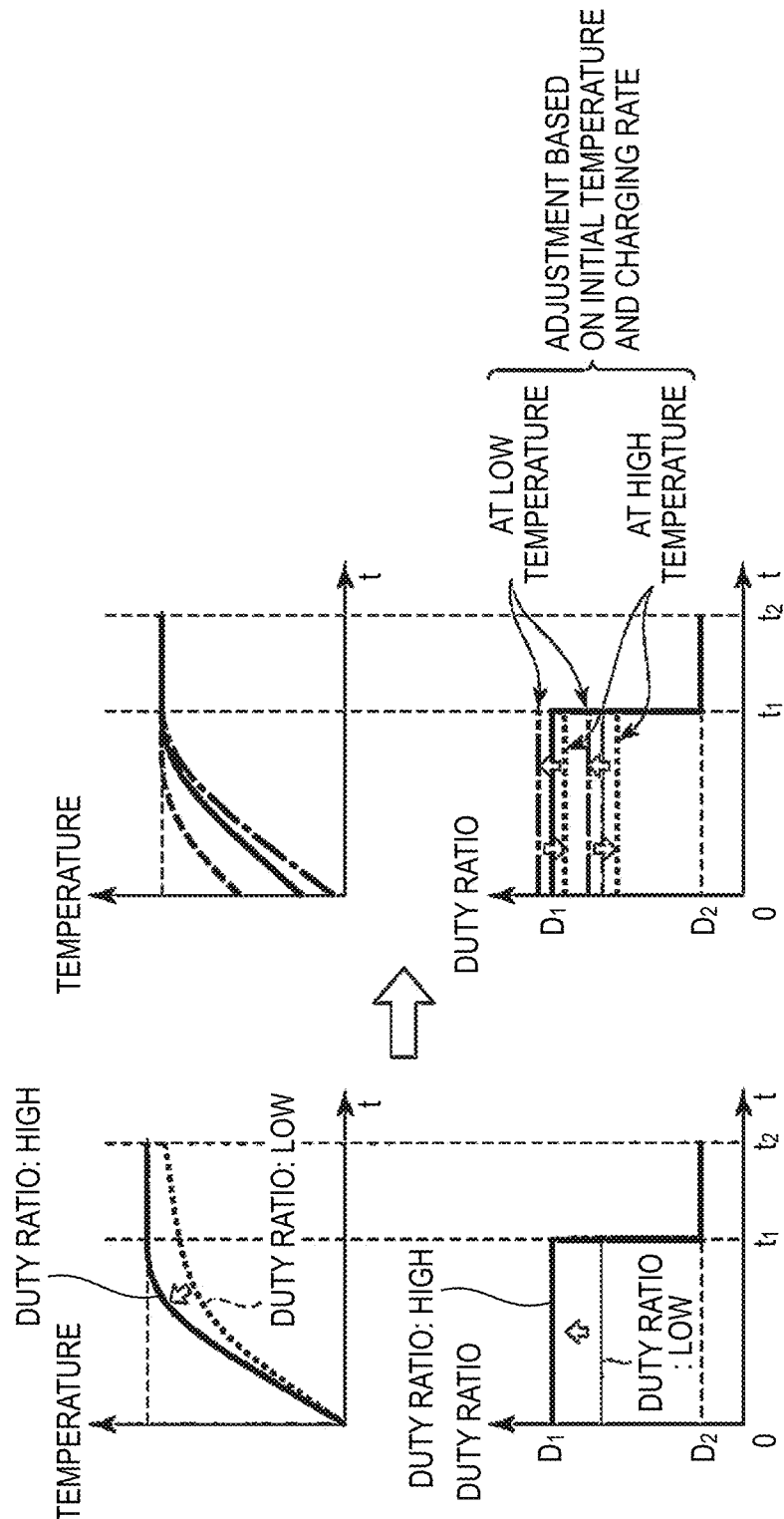
FIG. 14 is a graph depicting an example of control that is executed by the control unit in accordance with Example 1D.

FIG. 14 is a graph depicting an example of control that is executed by the control unit 8 in accordance with Example 1D. In FIG. 14, the horizontal axis indicates the timer value t. The vertical axis indicates the temperature or the duty ratio of the power that is supplied to the load 3.

The left graph of FIG. 14 pictorially depicts a relation between the duty ratio and the change in temperature of the load 3. In the left graph of FIG. 14, only the duty ratio $D_1$ in the first sub-phase of the duty ratio $D_1$ in the first sub-phase and the duty ratio $D_2$ in the second sub-phase is changed. When the duty ratio $D_1$ is set to the large duty ratio shown with the thick solid line, the temperature of the load 3 changes as shown with the solid line in the left upper graph of FIG. 14, for example. On the other hand. When the duty ratio $D_1$ is set to the small duty ratio shown with the thin solid line, the temperature of the load 3 changes as shown with the dotted line in the left upper graph of FIG. 14, for example. As shown in the left graph of FIG. 14, the temperature of the load 3 changes according to the level (height) of the duty ratio $D_1$ in the first sub-phase, i.e., the temperature of the load 3 is different at each timer value t.

That is, even though the initial conditions such as values relating to the temperature of the load 3 and the remaining amount of the power source 4 are different, when the duty ratio $D_1$ in the first sub-phase is adjusted, the temperature of the load 3 at the end of the preparation phase can be controlled further highly.

Therefore, the control unit 8 in accordance with Example 1D performs control so that the higher the temperature of the load 3 (initial temperature) at the start of the first sub-phase is, the smaller the duty ratio $D_1$ in the first sub-phase is, and the lower the temperature of the load 3 at the start of the first sub-phase is, the larger the duty ratio $D_1$ in the first sub-phase is, as shown in the right graph of FIG. 14.

In the meantime, the control unit 8 in accordance with Example 1D may change the duty ratio $D_1$, based on the value (for example, the output voltage of the power source 4) relating to the remaining amount of the power source 4, in addition to the temperature of the load 3 at the start of the first sub-phase. In this way, as shown in the right graph of FIG. 14, even though the initial conditions such as values relating to the temperature of the load 3 and the remaining amount of the power source 4 are different, it is possible to control further highly the temperature of the load 3 at the end of the preparation phase and to approach the same to a specific value.

Figure 15:
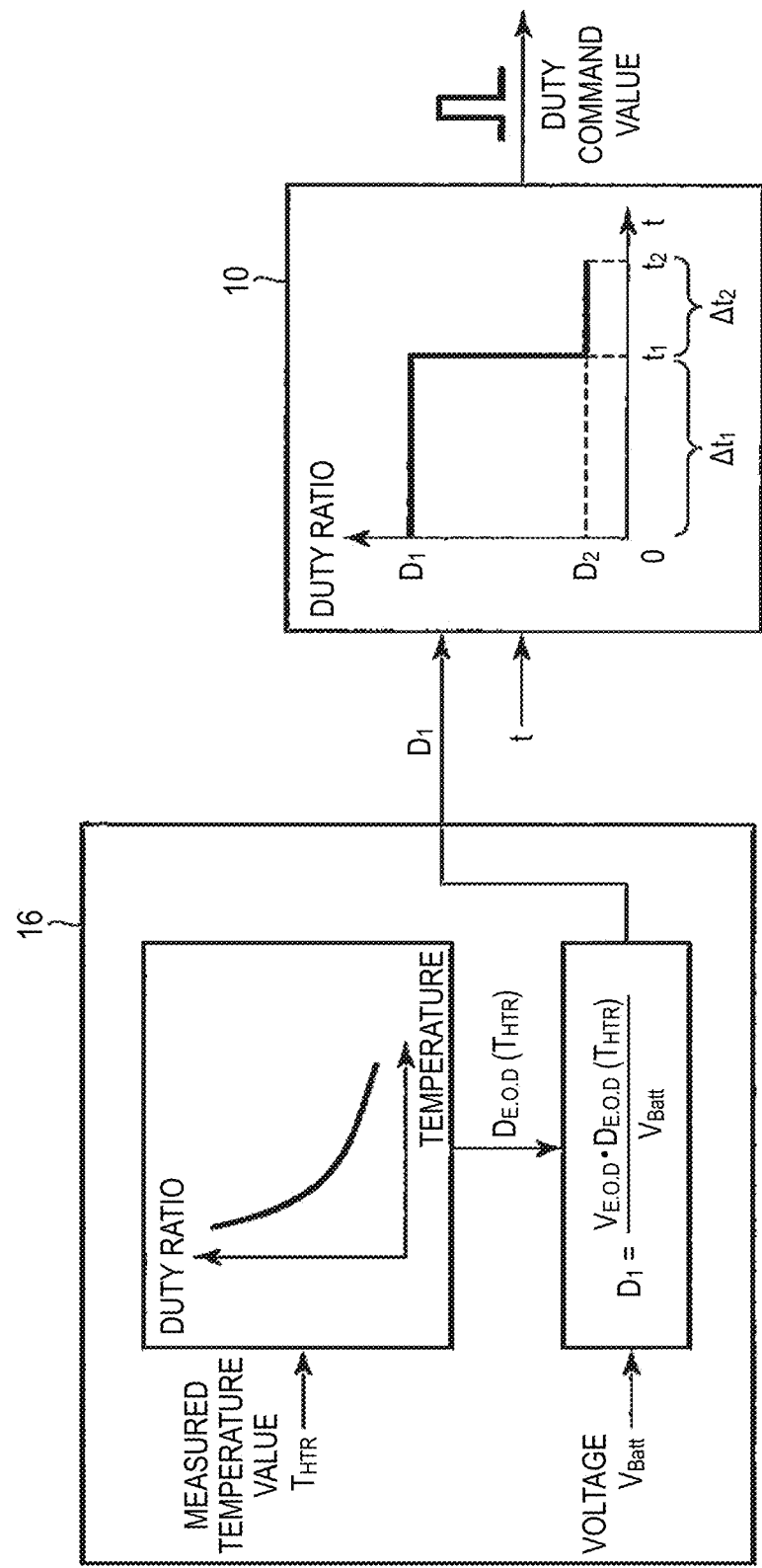
FIG. 15 is a control block diagram depicting an example of control that is executed by the control unit in accordance with Example 1D.

FIG. 15 is a control block diagram depicting an example of control that is executed by the control unit 8 in accordance with Example 1D.

In Example 1D, the control unit 8 includes an initial setting unit 16, and a preparation unit 10.

The initial setting unit 16 has a relation between the temperature of the load 3 and the duty ratio $D_{E.O.D}$ corresponding to the discharge-end voltage $V_{E.O.D}$.

The initial setting unit 16 receives the measured temperature value $T_{HTR}$ at the start of the first sub-phase from the temperature measurement unit 6, and obtains a duty ratio $D_{E.O.D}$ ($T_{HTR}$) corresponding to the discharge-end voltage $V_{E.O.D}$, based on the relation between the temperature and the duty ratio and the measured temperature value $T_{HTR}$.

Also, the initial setting unit 16 inputs the voltage $V_{Batt}$ from the power source measurement unit 7, obtains the duty ratio $D_1 = V_{E.O.D} \cdot D_{E.O.D}(T_{HTR})/V_{Batt}$, and outputs the duty command value indicative of the duty ratio $D_1$ to the preparation unit 10.

When the timer value t is input from the timer 5 to the preparation unit 10, the preparation unit 10 determines whether the timer value t is in the first sub-phase or the second sub-phase, controls the power that is supplied to the load 3, based on the duty command value indicative of the duty ratio $D_1$ in the first sub-phase, and controls the power that is supplied to the load 3, based on the duty command value indicative of the duty ratio $D_2$ in the second sub-phase.

Figure 16:
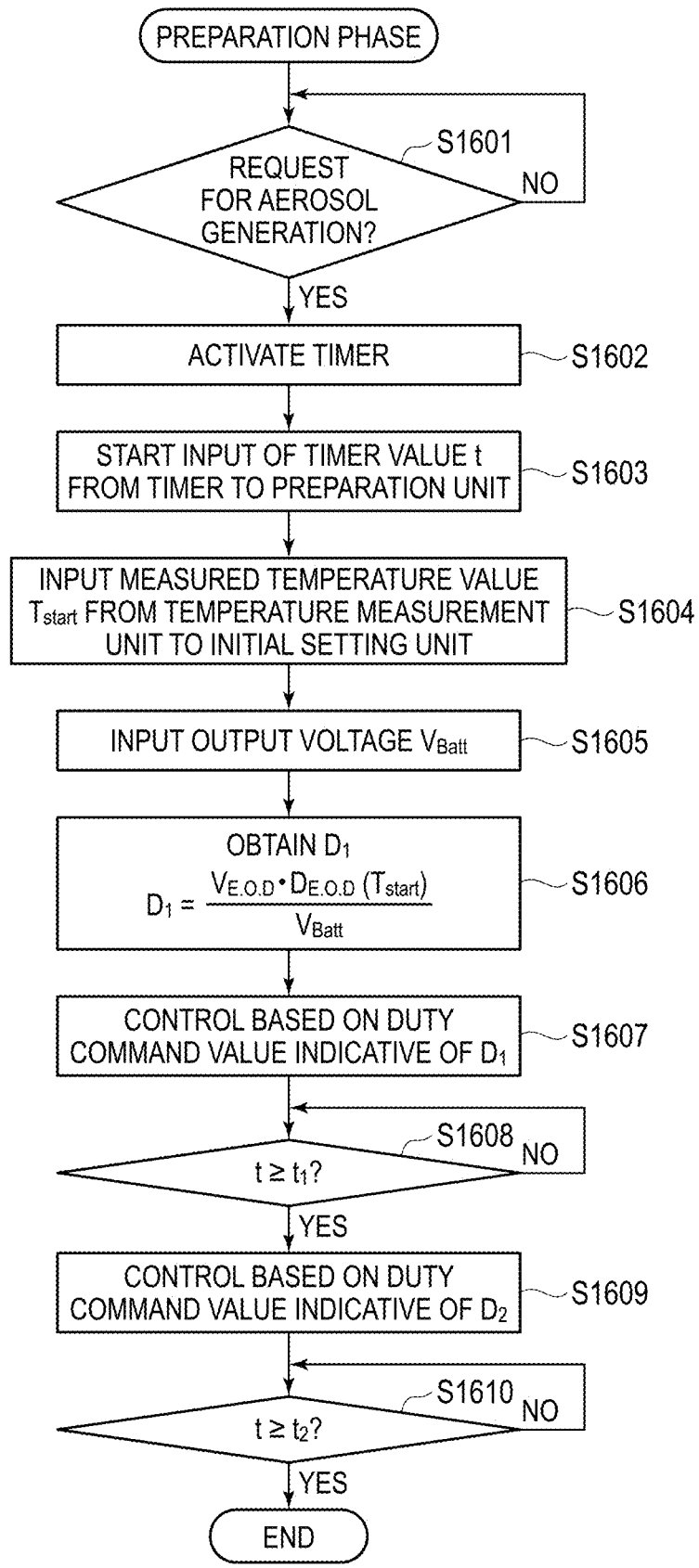
FIG. 16 is a flowchart depicting an example of processing in the preparation phase by the control unit in accordance with Example 1D.

FIG. 16 is a flowchart depicting an example of processing in the preparation phase by the control unit 8 in accordance with Example 1D.

The processing from step S1601 to step S1603 is the same as the processing from step S501 to step S503 in FIG. 5.

In step S1604, the measured temperature value $T_{start}$ at the start of the first sub-phase is input from the temperature measurement unit 6 to the initial setting unit 16.

In step S1605, the output voltage $V_{Batt}$ of the power source 4 is input from the power source measurement unit 7 to the initial setting unit 16.

In step S1606, the initial setting unit 16 obtains the duty ratio $D_{E.O.D}$ ($T_{start}$) corresponding to the discharge-end voltage $V_{E.O.D}$, based on the relation between the temperature and the duty ratio and the measured temperature value $T_{start}$ input in step S1604, and obtains the duty ratio $D_1 = _{E.O.D} \cdot D_{E.O.D}(T_{start})/V_{Batt}$, based on the voltage $V_{Batt}$ and the duty ratio $D_{E.O.D}$ ($I_{start}$).

In step S1607, the preparation unit 10 switches the switch 25 provided in the circuit for electrically connecting the load 3 and the power source 4 as shown in FIG. 9, based on the duty ratio $D_1$, thereby controlling the power that is supplied to the load 3.

The processing from step S1608 to step S1610 is the same as the processing from step S505 to step S507 in FIG. 5.

As described above, the control unit 8 in accordance with Example 1D changes the duty ratio $D_1$ in the first sub-phase, based on the values relating to the initial temperature of the load 3 and the remaining amount of the power source 4. More specifically, the initial setting unit 16 obtains the duty ratio $D_{E.O.D}$ ($T_{start}$) corresponding to the discharge-end voltage $V_{E.O.D}$, based on the relation between the temperature and the duty ratio and the measured temperature value $T_{start}$, and obtains the duty ratio $D_1$ corresponding to the first sub-phase, based on the discharge-end voltage $V_{E.O.D}$, the duty ratio $D_{E.O.D}$ ($T_{start}$), and the voltage $V_{Batt}$. Thereby, it is possible to control further highly the temperature of the load 3 at the end of the preparation phase even by the feed-forward control in which a control amount of a control target is not used as a feedback component for determining the operating amount.

Example 1E

In Example 1E, it is described that the feed-forward control is changed based on deterioration in the load 3 in the preparation phase.

When the total number of uses $N_{sum}$ of the load 3 increases, an impair, an oxidation phenomenon and the like occur, so that the load 3 is deteriorated. When the load 3 is deteriorated, the electric resistance value $R_{HTR}$ of the load 3 tends to increase. That is, there is a correlation between the total number of uses $N_{sum}$ indicative of a deterioration state in the load 3 and the electric resistance value $R_{HTR}$ of the load 3.

Therefore, in Example 1E, the power is supplied to the load 3 so that the temperature of the load 3 is stable even when the resistance value $R_{HTR}$ is increased due to the deterioration in the load 3. In the below, a method of supplying the power to the load 3 so that the temperature of the load 3 is stable irrespective of the deterioration state in the load 3 is described in detail.

When the current that flows through the load 3 is denoted as $I_{HTR}$, the voltage that is applied to the load 3 is denoted as $V_{HTR}$, the power that is supplied to the load 3 is denoted as $P_{HTR}$, a resistance of the load is denoted as $R_{HTR}$, the output voltage of the power source 4 is denoted as V, and the duty ratio of the power that is supplied to the load 3 is denoted as D, equations (2) and (3) are obtained, in the meantime, it should be noted that $V_{HTR}$ is an effective value of the voltage.

[equation 2]

$$I_{HTR} = \frac{V \cdot D}{R_{HTR}} \quad (2)$$

[equation 3]

$$P_{HTR} = V_{HTR} \cdot I_{HTR} = \frac{(V \cdot D)^2}{R_{HTR}} \quad (3)$$

Herein, the power is denoted as $P_{HTR\_new}$ when the load 3 is new (not deteriorated), the resistance is denoted as $R_{HTR\_new}$ when the load 3 is new, and the duty ratio is denoted as $D_{new}$ when the load 3 is new.

Also, the power is denoted as $P_{HTR\_used}$ when the load 3 is old (deteriorated), the resistance is denoted as $R_{HTR\_used}$ when the load 3 is old, and the duty ratio is denoted as $D_{used}$ when the load 3 is old.

The power $P_{HRT\_new}$ when the load 3 is new is preferably the same as the power $P_{HTR\_used}$ when the load 3 is old.

Therefore, a following equation (4) is obtained.

[equation 4]

$$P_{HTR\_new} = P_{HTR\_used} \rightarrow \frac{(V \cdot D_{new})^2}{R_{HTR\_new}} = \quad (4)$$

$$\frac{(V \cdot D_{used})^2}{R_{HTR\_used}} \rightarrow \frac{D_{used}}{D_{new}} = \sqrt{\frac{R_{HTR\_used}}{R_{HTR\_new}}} \rightarrow D_{used} = \sqrt{\frac{R_{HTR\_used}}{R_{HTR\_new}}} \cdot D_{new}$$

When the correlation between the total number of uses $N_{sum}$ indicative of a deterioration state in the load 3 and the electric resistance value $R_{HTR}$ of the load 3 is linear or can be linearly approximated, the equation (4) can be rewritten to a following equation (5).

[equation 5]

$$D_{used} \equiv \sqrt{\frac{\alpha \cdot N_{sum} \cdot R_{HTR\_new}}{R_{HTR\_used}}} \cdot D_{new} = \sqrt{\alpha \cdot N_{sum}} \cdot D_{new} \quad (5)$$

Therefore, in a case where the correlation between the total number of uses $N_{sum}$ indicative of a deterioration stale in the load 3 and the electric resistance value $R_{HTR}$ of the load 3 is linear or can be linearly approximated, the control unit 8 can obtain the duty ratio $D_{used}$ corresponding to the deteriorated load 3 based on the equation (5), when the total number of uses $N_{sum}$ of the load 3 is acquired.

On the other hand, in a case where the correlation between the total number of uses $N_{sum}$ indicative of a deterioration state in the load 3 and the electric resistance value $R_{HTR}$ of the load 3 is nonlinear, when the electric resistance value $R_{HTR}$ of the load 3 is indicated by the function of the total number of uses $N_{sum}$ of the load 3, the equation (4) can be rewritten to a following equation (6).

[equation 6]

$$D_{used} \equiv \sqrt{\frac{R_{HTR}(N_{sum})}{R_{HTR}(0)}} \cdot D_{new} \qquad (6)$$

Therefore, in a case where the correlation between the total number of uses $N_{sum}$ indicative of a deterioration state in the load 3 and the electric resistance value $R_{HTR}$ of the load 3 is nonlinear, when the total number of uses $N_{sum}$ of the load 3 is acquired, the control unit 8 can use the equation (6) to obtain the duty ratio $D_{used}$ corresponding to the deteriorated load 3, based on a resistance R(0) of the load 3 whose the total number of uses $N_{sum}$ is zero (the load 3 is new), a resistance $R(N_{sum})$ of the load 3 whose the total number of uses is $N_{sum}$, and the duty ratio $D_{new}$ when the load 3 is new.

Figure 17:
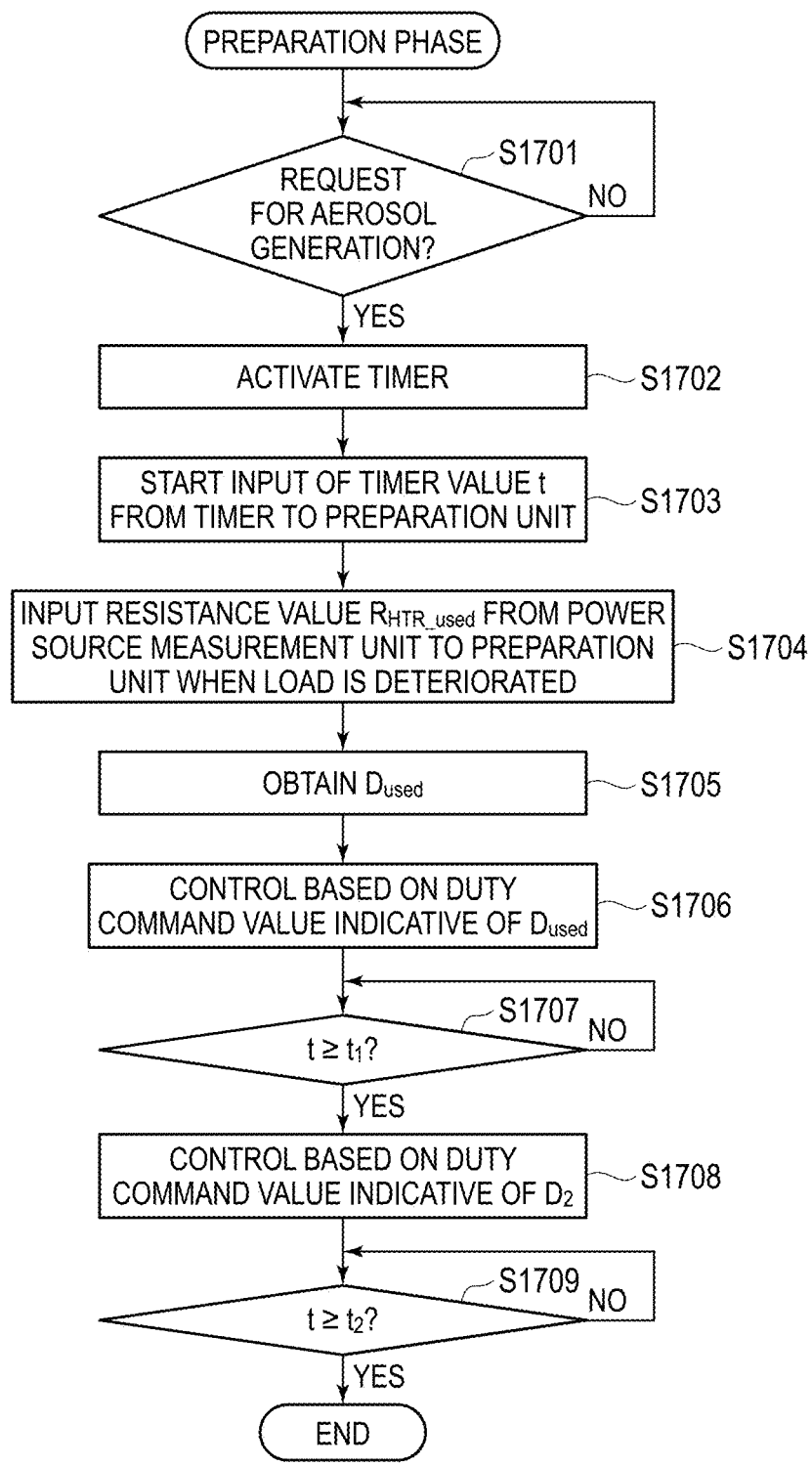
FIG. 17 is a flowchart depicting an example of processing in the preparation phase by the control unit in accordance with Example 1E.

FIG. 17 is a flowchart depicting an example of processing in the preparation phase by the control unit 8 in accordance with Example 1E.

The processing from step S1701 to step S1703 is the same as the processing from step S501 to step S503 in FIG. 5.

In step S1704, the resistance value $R_{HTR\_used}$ when the load 3 is deteriorated is input from the power source measurement unit 7 to the preparation unit 10.

In step S1705, when the correlation between the total number of uses $N_{sum}$ indicative of a deterioration state in the load 3 and the electric resistance value $R_{HTR}$ of the load 3 is linear or can be linearly approximated, the preparation unit 10 obtains the duty ratio $D_{used}$ corresponding to the deteriorated load 3, based on the acquired total number of uses $N_{sum}$ of the load 3 and the equation (5). On the other hand, when the correlation between the total number of uses $N_{sum}$ indicative of a deterioration state in the load 3 and the electric resistance value $R_{HTR}$ of the load 3 is nonlinear, the preparation unit 10 uses the equation (6) to obtain the duty ratio $D_{used}$ corresponding to the deteriorated load 3, based on the total number of uses $N_{sum}$ of the load 3, the resistance R(0) of the load 3 when the total number of uses $N_{sum}$ is zero (the load 3 is new), the resistance $R(N_{sum})$ of the load 3 when the total number of uses is $N_{sum}$, and the duty ratio $D_{new}$ when the load 3 is new.

In step S1706, the preparation unit 10 switches the switch 25 provided in the circuit for electrically connecting the load 3 and the power source 4 as shown in FIG. 9, based on the duty command value indicative of the duty ratio $D_{used}$, in the first sub-phase, thereby controlling the power that is supplied to the load 3.

The processing from step S1707 to step S1709 is the same as the processing from step S505 to step S507 in FIG. 5.

In Example 1E as described above, even when the load 3 is deteriorated due to factors such as the increase in the total number of uses $N_{sum}$ of the load 3, the power can be supplied to the load 3 so that the temperature of the load 3 is stabilized.

In the present Example, the total number of uses $N_{sum}$ of the load 3 is used as the physical quantity indicative of the deterioration state in the load 3. However, instead of the total number of uses $N_{sum}$, for example, an integrated operation time of the load 3, an integrated power consumption of the load 3, an integrated amount of aerosol generation of the load 3, an electric resistance value of the load 3 at predetermined temperatures such as room temperature and the like may also be used.

Second Embodiment

In a second embodiment, control of changing at least one of a gain of the gain unit 12 and a limiter width (range) that is used in the limiter unit 14 in the feedback control that is executed in the use phase is described.

In the aerosol generation device 1 configured to heat the aerosol generation article 9, in order to stabilize aerosols generated from the aerosol generation article 9 over time, it is necessary to gradually shift an aerosol generation position of the aerosol generation article 9 away from the vicinity of the load 3 by increasing gradually the temperature of the load 3 or the aerosol generation article 9. The reason is that when the heating of the aerosol generation article 9 starts, aerosols are generated earlier in a position closer to the load 3 in the aerosol generation article 9, taking into account heat transfer from the load 3 to the aerosol generation article 9. That is, when an aerosol source in a position of the aerosol generation article 9 close to the load 3 is completely atomized and the aerosol generation is completed, it is necessary to atomize an aerosol source distant from the load 3 so as to continuously generate aerosols from the aerosol generation article 9. That is, it is necessary to shift the aerosol generation position from a position of the aerosol generation article 9 close to the load 3 to a position of the aerosol generation article 9 distant from the load 3, in which the aerosol source is not completely atomized because the heat transfer efficiency from the load 3 decreases.

As described above, the position of the aerosol generation article 9 distant from the load 3 is inferior to the position of the aerosol generation article 9 close to the load 3, from a standpoint of heat transfer. Therefore, when it is intended to generate aerosols in the position of the aerosol generation article 9 distant from the load 3, it is necessary for the load 3 to transfer much heat to the aerosol generation article 9, as compared to a case where aerosols are generated in the position of the aerosol generation article 9 close to the load 3. In other words, when it is intended to generate aerosols in the position of the aerosol generation article 9 distant from the load 3, it is necessary to increase the temperature of the load 3, as compared to a case where aerosols are generated in the position of the aerosol generation article 9 close to the load 3.

In the second embodiment, control of stabilizing an amount of aerosols generated from the aerosol generation article 9 over time by shifting the aerosol generation position of the aerosol generation article 9 from a position close to the load 3 to a position distant from the load is described.

For example, when a first heating method in which the load 3 heats the aerosol generation article 9 from an inside thereof is used, a central part of the aerosol generation article 9 is the position of the aerosol generation article 9 close to the load 3. Also, an outer peripheral part of the aerosol generation article 9 is the position of the aerosol generation article 9 distant from the load 3.

For example, when a second heating method in which the load 3 heats the aerosol generation article 9 from an outside thereof is used, the outer peripheral part of the aerosol generation article 9 is the position of the aerosol generation article 9 close to the load 3. Also, the central part of the aerosol generation article 9 is the position of the aerosol generation article 9 distant from the load 3.

For example, when a third heating method in which the load 3 heats the aerosol generation article 9 by using induction heating (IH) is used, a position of the aerosol generation article 9 that is in contact with or close to a susceptor is the position of the aerosol generation article 9 close to the load 3. Also, a position of the aerosol generation article 9 that is not in contact with or is distant from the susceptor is the position of the aerosol generation article 9 distant from the load 3.

However, when it is intended to gradually increase the temperature of the load 3 or the aerosol generation article 9 by increasing gradually a target temperature in the feedback control, if the measured temperature value exceeds temporarily the target temperature, the increase in temperature at that time is stagnant, so that the user who inhales aerosols may feel uncomfortable.

Therefore, in the second embodiment, at least one of a gain of the gain unit 12 and the limiter width of the limiter unit 14 in the use phase is gradually increased to smoothly increase the temperature of the load 3 or the aerosol generation article 9 without delay, thereby generating stably aerosols. In the meantime, the increase in the gain of the gain unit 12 may mean adjusting a correlation between an output value and an input value of the gain unit 12 so that an absolute value of an output value to an input value input to the gain unit 12 after a gain is increased is greater than an absolute value of the output value to the input value input to the gain unit 12 before a gain is increased. Also, the increase in the limiter width of the limiter unit 14 may mean increasing a maximum value that can be taken as an absolute value of an output value that is output from the limiter unit 14.

Comparing the control by the control unit 8 in accordance with the second embodiment and the control by an aerosol generation device of the related art, the control by the control unit 8 in accordance with the second embodiment has a feature of performing the control while setting the use phase end temperature constant, not the control of increasing, decreasing and again increasing the target temperature that is used in the feedback control. That is, in the second embodiment, since the temperature of the load 3 is lower than the use phase end temperature that is used in the feedback control, in most of the use phase, the temperature of the load 3 or the aerosol generation article 9 is smoothly increased without delay over the entire use phase, so that aerosols are stably generated.

The control by the control unit 8 in accordance with the second embodiment has a feature that it is not a control of narrowing the limiter width of the limiter unit 14 based on the timer value t. Also, the control h the control unit 8 in accordance with the second embodiment has a feature that it is not a control of increasing the target temperature based on the timer value t while setting the limiter width of the limiter unit 14 constant, in other words, in the control by the control unit 8 in accordance with the second embodiment, the limiter width is continuously expanded or stepwise narrowed without being narrowed with the progress of the use phase.

When the temperature of the load 3 in the use phase is equal to or higher than a value at which the predetermined amount or more of aerosols can be generated from the aerosol generation article 9, for example, the control unit 8 in accordance with the second embodiment may acquire the temperature of the load 3 and a degree of progress of the use phase, execute the feedback control so that the temperature of the load 3 converges to a predetermined temperature, and increase a gain in the feedback control or an upper limit value of the power that is supplied from the power source 4 to the load 3, as the degree of progress progresses in the feedback control. Thereby, it is possible to increase gradually and stably the temperature of the load 3 without delay. That is, it is possible to stabilize the amount of aerosols that are generated from the aerosol generation article 9, over the entire use phase.

Herein, the control unit 8 may increase the gain in the feedback control by changing any element of proportional (P) control, integral (I) control and differential (D) control of PID (Proportional Integral Differential) control. Also, the control unit 8 may increase one gain of proportional control, integral control and differential control or may increase a plurality of gains. Also, the control unit 8 may increase both the gain and the upper limit value of the power that is supplied to the load 3.

The control unit 8 may be configured to increase the gain or upper limit value as the degree of progress progresses so that the temperature of the load 3 does not decrease from the start of the use phase. Thereby, it is possible to suppress the amount of aerosol generation from being reduced.

An increase width of the gain or upper limit value with respect to a progressing width of the degree of progress may be set constant. Thereby, it is possible to improve the stability of the feedback control.

The control unit 8 may be configured to change an increase rate of the gain or upper limit value to the progressing width of the degree of progress. Thereby, it is possible to generate an appropriate amount of aerosols according to the degree of progress.

The control unit 8 may be configured to increase the increase rate as the degree of progress progresses. Thereby, it is possible to suppress the amount of aerosol generation from being reduced. Also, it is possible to shorten a time period during which the load 3 is at high temperatures, so that it is possible to suppress the load 3 and the aerosol generation device 1 from being overheated, thereby improving the durability of the load 3 and the aerosol generation device 1. Also, since the time period during which the load 3 is at high temperatures is short, it is possible to simplify an adiabatic structure of the aerosol generation device 1. In particular, when the aerosol generation device 1 adopts the second heating method, it is possible to simplify the adiabatic structure.

The control unit 8 may be configured to reduce the increase rate as the degree of progress progresses. Thereby, it is possible to prolong a time period during which the load 3 is at high temperatures, so that it is possible to suppress the amount of aerosol generation from being reduced. Since it is possible to prolong the time period during which the load 3 is at high temperatures, it is possible to increase the amount of aerosols that are generated from one aerosol generation article 9. Also, since a time period during which the gain or upper limit value increases is long, it is possible to promptly recover the decrease in temperature (for example, temperature drop) due to the inhalation of aerosols by the user, thereby compensating for the temperature of the load 3. That is, it is possible to stabilize the amount of aerosols that are generated from one aerosol generation article 9, over the entire use phase.

The control unit 8 may be configured to determine the gain or upper limit value corresponding to the degree of progress, based on a first relation (correlation) that the gain or upper limit value increases as the degree of progress progresses, and to change the first relation, based on time-series change in the degree of progress. Thereby, it is possible to change a degree of increase in the gain or upper limit value, in accordance with a progressing degree of the degree of progress, and to supply an appropriate amount of power to the load 3 in accordance with an actual progressing degree, so that it is possible to stabilize the amount of aerosol generation.

The control unit 8 may be configured to change the first relation so that the gain or upper limit value increases as the degree of progress progresses. In this case, since the gain or upper limit value is not decreased, it is possible to suppress the amount of aerosol generation from being reduced.

When the degree of progress is delayed in comparison with a predetermined degree of progress, the control unit 8 may change the first relation so that the increase width of the gain or upper limit value corresponding to the progressing width of the degree of progress increases, and may set the temperature of the load 3 as the degree of progress. Thereby, as the increase in temperature of the load 3 is further delayed, it is possible to easily increase the temperature of the load 3, so that it is possible to suppress the amount of aerosol generation from being reduced.

When the degree of progress is further progressed in comparison with a predetermined degree of progress, the control unit 8 may change the first relation so that the increase width of the gain or upper limit value corresponding to the progressing width of the degree of progress decreases, and may set the temperature of the load 3 as the degree of progress. Thereby, as the increase in temperature of the load 3 is further progressed, it is possible to make it difficult for the temperature of the load 3 to increase, so that it is possible to suppress the amount of aerosol generation from increasing.

When the degree of progress is delayed in comparison with a predetermined degree of progress, the control unit 8 may change the first relation so that the increase width of the gain or upper limit value corresponding to the progressing width of the degree of progress decreases, and may set the degree of progress to include at least one of a number of times of aerosol inhalation, an amount of aerosol inhalation, and an amount of aerosol generation. For example, when aerosol inhalation is delayed in comparison with a predetermined degree of progress, it is believed that the aerosol source near the load 3 is not depleted. In this case, when the increase width of the gain or upper limit value is decreased, it is possible to effectively use the aerosol source in the aerosol generation article 9.

When the degree of progress is further progressed in comparison with a predetermined degree of progress, the control unit 8 may change the first relation so that the increase width of the gain or upper limit value corresponding to the progressing width of the degree of progress increases, and may set the degree of progress to include at least one of a number of times of aerosol inhalation, an amount of aerosol inhalation, and an amount of aerosol generation. For example, when the degree of progress is further progressed in comparison with a predetermined degree of progress, it is believed that the aerosol generation position of the aerosol generation article 9 is shifted to a position distant from the load 3 than expected. Even in this case, when the increase width of the gain or upper limit value is increased, it is possible to positively generate aerosols from the aerosol generation position distant from the load 3.

The control unit 8 may be configured to temporarily change the first relation or to change a part of the first relation. In this case, since the increase width of the gain or upper limit value is temporarily changed and is then returned to the original increase width, it is possible to improve the stability of the control.

The control unit 8 may be configured to change an entire part of the first relation after the latest degree of progress acquired by the control unit 8. In this case, since the increase width of the gain or upper limit value is entirely changed, it is possible to reduce a possibility that it will be necessary to again perform the change.

In the meantime, the control unit 8 may be configured to change the entire first relation including the degree of progress more past than the latest degree of progress.

The control unit 8 may be configured to change a part of the first relation after the latest degree of progress acquired by the control unit 8, and may set a relation between the degree of progress and the gain or upper limit value at the end of the use phase to be the same before and after the change of the first relation. In this case, since the gain or upper limit value does not change at the end of the use phase, it is possible to suppress the amount of power supplied to the load 3 from largely changing, thereby improving the stability of the control.

The predetermined temperature may be a temperature of the load 3 that is necessary to generate aerosols from the aerosol source or the aerosol-forming substrate 9a included in the mounted aerosol generation article 9 and located in a position most distant from the load 3. Thereby, it is possible to effectively generate aerosols from the aerosol generation article 9.

When the temperature of the load 3 reaches the predetermined temperature, the control unit 8 may end the use phase. Thereby, it is possible to suppress the aerosol generation article 9 from being overheated.

When the temperature of the load 3 reaches the predetermined temperature or when the degree of progress reaches the predetermined threshold value, the control unit 8 may end the use phase. Thereby, it is possible to end the feedback control more safely and securely.

When the temperature of the load 3 reaches the predetermined temperature and the degree of progress reaches a predetermined threshold value, the control unit 8 may end the use phase. Thereby, it is possible to generate more aerosols from the aerosol generation article 9 while strictly setting the end condition in an appropriate range.

The control unit 8 may be configured to increase the gain or upper limit value so that a time period in which the temperature of the load 3 is lower than the predetermined temperature is longer than a time period in which the temperature of the load 3 is equal to or higher than the predetermined temperature, in the use phase. In this case, since the time period in which the temperature of the load 3 is not near the predetermined temperature is longer than the time period in which the temperature of the load 3 is near the predetermined temperature, it is possible to suppress the increase in amount of aerosol generation.

As the degree of progress, elapse time of the use phase, the number of times of aerosol inhalation, the amount of aerosol inhalation, the amount of aerosol generation or the temperature of the load 3 can be used according to the control of the control unit 8.

The control unit 8 in accordance with the second embodiment is configured to increase the gain in the feedback control or the upper limit value of the power that is supplied from the power source 4 to the load so that the temperature of the load 3 gradually approaches from a first temperature, at which the predetermined amount or more of aerosols can be generated from the aerosol source or the aerosol-forming substrate 9a included in the aerosol generation article 9 and located in a closest position to the load 3, to a second temperature at which the predetermined amount or more of aerosols can be generated from the aerosol source or the aerosol-forming substrate 9a included in the aerosol generation article 9 and located in a position most distant from the load 3, for example. Thereby, the control unit 8 can effectively perform the aerosol generation over the entire range from a position close to the load 3 to a position of the aerosol generation article 9 distant from the load 3 by the feedback control.

In the case of the use phase where the temperature of the load 3 is equal to or greater than a value at Which the predetermined amount or more of aerosols can be generated from the aerosol generation article 9, for example, the control unit 8 in accordance with the second embodiment may acquire the temperature of the load 3 and the degree of progress of the use phase, determine the power that is supplied from the power source 4 to the load 3, based on a difference between the temperature of the load 3 and the predetermined temperature, and execute the feedback control so that a change rate of the supply amount of power with the progressing of the use phase is greater than a change rate of the predetermined temperature with the progressing of the use phase. In the meantime, the change rate may also include a state in which the change rate is zero, i.e., there is no change. Thereby, it is possible to increase gradually and stably the temperature of the load 3 without delay.

In the case of the use phase where the temperature of the load 3 is equal to or greater than a value at which the predetermined amount or more of aerosols can be generated from the aerosol generation article 9, for example, the control unit 8 in accordance with the second embodiment may acquire the temperature of the load 3 and the degree of progress of the use phase, determine the power that is supplied from the power source 4 to the load 3, based on a difference between the temperature of the load 3 and the predetermined temperature, and execute the feedback control so that a value obtained by subtracting the temperature of the load 3 from the predetermined temperature decreases with the progressing of the use phase and the supply amount of power that is supplied from the power source 4 to the load 3 increases with the progressing of the use phase. Thereby, it is possible to increase gradually and stably the temperature of the load 3 without delay.

The diverse controls by the control unit 8 may also be implemented as the control unit 8 executes the program.

Regarding the second embodiment, specific control examples are further described in following embodiments 2A to 2F.

Example 2A

Figure 18:
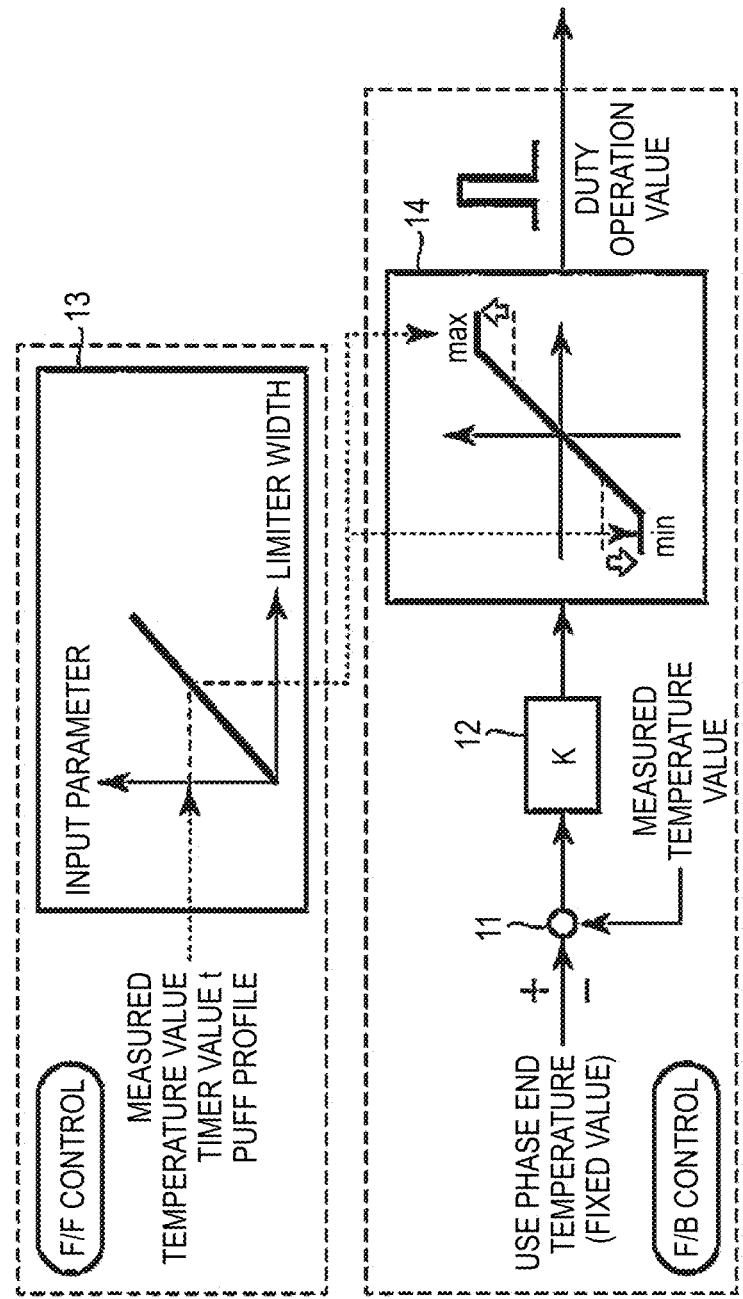
FIG. 18 is a control block diagram depicting an example of control that is executed by the control unit in accordance with Example 2A.

FIG. 18 is a control block diagram depicting an example of control that is executed by the control unit 8 in accordance with Example 2A.

The limiter change unit 13 of the control unit 8 keeps the first relation in Which an input parameter including at least one of the tinier value t, the measured temperature value of the load 3 and a puff profile and the limiter width of the limiter unit 14 are associated with each other. The timer value t, the measured temperature value of the load 3, and the puff profile are examples of the value indicative of the degree of progress of the use phase. Instead, other physical quantities or variables that tend to increase according to the degree of progress of the use phase may also be used.

In Example 2A, a case where the timer value t, the measured temperature value and the puff profile are used as the input parameter is described. However, a part of the timer value t, the measured temperature value and the puff profile may also be used as the input parameter.

The association between the input parameter and the limiter width may be managed by a table or a data structure such as a list structure and a function relating to the input parameter and the limiter width may be used. The same applies to a variety of associations described later.

In the use phase, the control unit 8 inputs the timer value t from the timer 5, and inputs the measured temperature value indicative of the temperature of the load 3 from the temperature measurement unit 6.

The control unit 8 detects the user's inhalation, based on an output value of a sensor configured to detect a physical quantity that varies with the user's inhalation, such as a flow rate sensor, a flow velocity sensor and a pressure sensor provided in the aerosol generation device 1, for example, and generates a puff profile indicative of an inhalation state such as the number of times of user's time-series inhalation or an amount of inhalation, for example.

The control unit 8 includes the limiter change unit 13, the differential unit 11, the gain unit 12, and the limiter unit 14.

The limiter change unit 13 determines an increase width of the limiter width that is used in the limiter unit 14, based on the input parameter, and gradually expands the limiter width as the use phase progresses.

In Example 2A, the limiter change unit 13 may not narrow the limiter width, for example. In other words, when changing the limiter width, the limiter change unit 13 may only expand the limiter width. In the below, also in Examples 2B to 2F of the second embodiment, the limiter width that is used in the limiter change unit 13 may not be narrowed.

More specifically, the limiter change unit 13 changes the limiter width of the limiter unit 14 so that a width between a limiter maximum value and a limiter minimum value is expanded, as the timer value t increases.

The differential unit 11 obtains a difference between the measured temperature value measured by the temperature measurement unit 6 and the use phase end temperature. In Example 2A, it is assumed that the use phase end temperature is a fixed value and is a value that the temperature of the load 3 should reach at the end of the use phase by the feedback control, for example.

The gain unit 12 obtains, based on the difference between the measured temperature value and the use phase end temperature, a duty ratio at which the difference is removed or reduced. In other words, the gain unit 12 outputs, to the limiter unit 14, a duty ratio having a correlation of a difference between the measured temperature value and the use phase end temperature and the duty ratio and corresponding to a difference between the input measured temperature value and the use phase end temperature.

The limiter unit 14 controls so that the duty ratio obtained by the gain unit 12 is included in the limiter width. Specifically, when the duty ratio obtained by the gain unit 12 exceeds the maximum value of the limiter width obtained by the limiter change unit 13, the limiter unit 14 sets the duty ratio as the maximum value of the limiter width, and when the obtained duty ratio falls below the minimum value of the limiter width obtained by the limiter change unit 13, the limiter unit 14 limits the duty ratio to the minimum value of the limiter width. The limiter unit 14 outputs, as a result of the limiter processing, a duty operation value indicative of the duty ratio included in the limiter width to the comparison unit 15 shown in FIG. 3, for example. The duty operation value is a value obtained as a result of the feedback control by the control unit 8.

Figure 19:
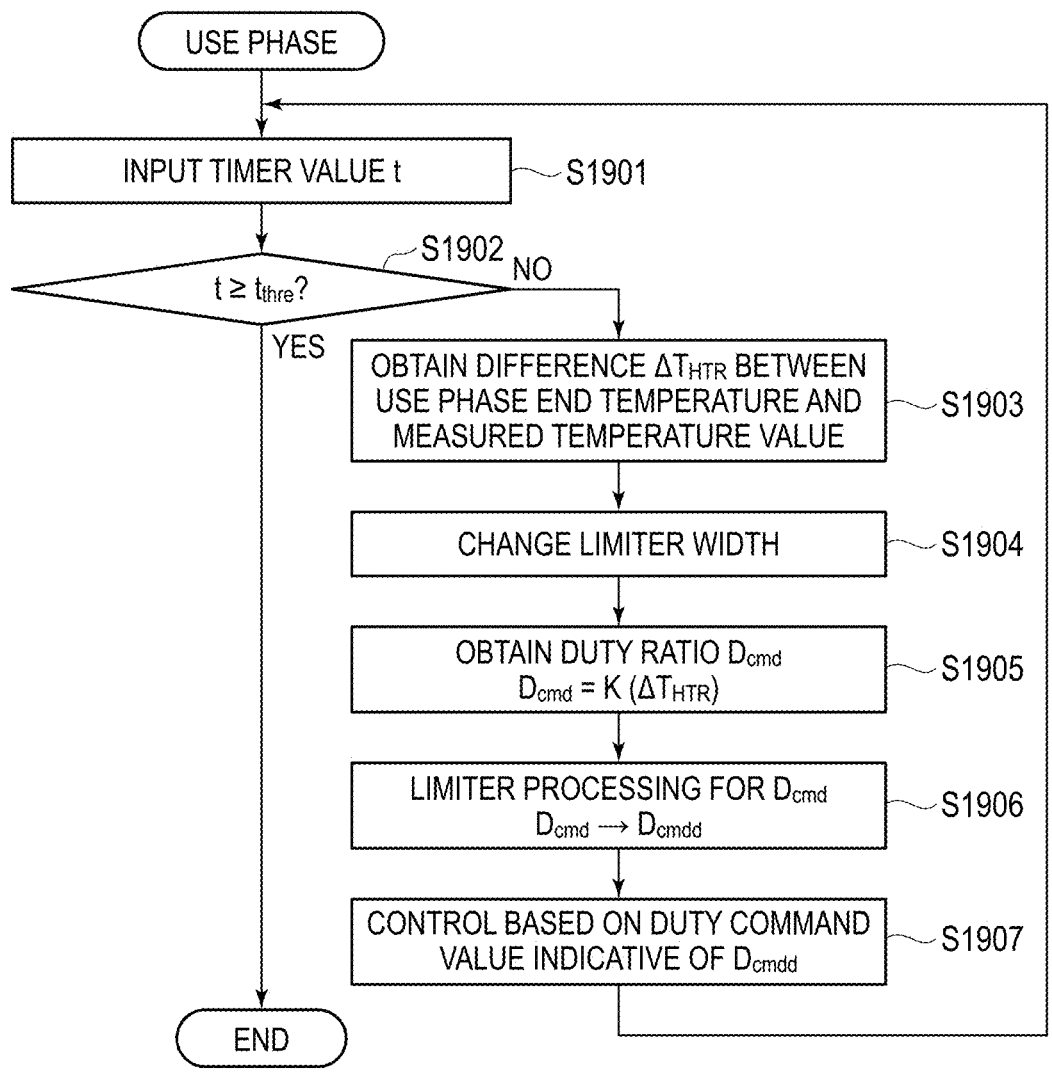
FIG. 19 is a flowchart depicting an example of processing in the use phase by the control unit in accordance with Example 2A.

FIG. 19 is a flowchart depicting an example of processing in the use phase by the control unit 8 in accordance with Example 2A.

In step S1901, the control unit 8 inputs the timer value t from the timer 5.

In step S1902, the control unit 8 determines whether the timer value t is equal to or greater than time $t_{thre}$ indicative of an end of the use phase.

When it is determined that the tinier value t is equal to or greater than time $t_{thre}$ (a determination result in step S1902 is affirmative), the control unit 8 stops the supply of power to the load 3, and ends the use phase.

When it is determined that the timer value t is not equal to or greater than time $t_{thre}$ (a determination result in step S1902 is negative), the differential unit 11 of the control unit 8 obtains a difference $\Delta T_{HTR}$ between the use phase end temperature of the load 3 and the measured temperature value input from the temperature measurement unit 6, in step S1903.

In step S1904, the limiter change unit 13 of the control unit 8 determines the increase width of the limiter width that is used in the limiter unit 14, based on at least one of the timer value t, the measured temperature value and the puff profile, and changes the limiter width.

In step S1905, the gain unit 12 of the control unit 8 obtains the duty ratio (the duty operation value) $D_{cmd}$, based on the difference $\Delta T_{HTR}$. When a correlation between the input value and the output value in the gain unit 12 is denoted as a function K, the processing of the gain unit 12 can be expressed by $D_{cmd}=K(\Delta T_{HTR})$. In particular, in a case where the correlation between the input value and the output value in the gain unit 12 is linear, when a gain coefficient that is a gradient of the correlation is denoted as K, the processing of the gain unit 12 can be expressed by $D_{cmd}=K\times\Delta T_{HTR}$.

In step S1906, the limiter unit 14 of the control unit 8 performs the limiter processing so that the duty ratio $D_{cmd}$ obtained by the gain unit 12 falls in the limiter width of the limiter unit 14, thereby obtaining a limiter processed duty ratio $D_{cmdd}$.

In step S1907, the control unit 8 controls the power that is supplied to the load 3, based on a duty command value indicative of the duty ratio $D_{cmdd}$, and then the processing returns to step S1901. In the meantime, the duty ratio $D_{cmdd}$ may also be applied to the switch 25 provided between the power source 4 and the load 3 or to the DC/DC converter provided between the power source 4 and the load 3.

In the above processing, the sequence of step S1904 and step S1905 may be interchanged.

In the control that is executed by the control unit 8 in accordance with Example 2A, the limiter width that is used in the limiter unit 14 is changed to be gradually expanded each time the use phase progresses, and the temperature of the load 3 is controlled based on the duty ratio $D_{cmdd}$ in the limiter width. Thereby, it is possible to smoothly increase the temperature of the load 3 or the aerosol generation article 9 without delay, so that it is possible to stably generate aerosols.

Example 2B

In Example 2B, control in which the limiter change unit 13 determines the increase width of the limiter width, based on a determination as to whether a heat capacity of the aerosol generation article 9 is greater than expected with the time-series progressing of the use phase, and changes the limiter width is described.

In Example 2B, the heat capacity of the aerosol generation article 9 may also be strictly obtained from a mass and a specific heat of the aerosol generation article 9. As another example, the heat capacity of the aerosol generation article 9 may be treated as a physical quantity that depends on compositions or structures of the aerosol-forming substrate 9a, the flavor source and the aerosol source provided in the aerosol generation article 9 and shows a larger value as the remaining amounts of the aerosol generation article 9, the flavor source and the aerosol source are larger. That is, when the aerosol generation article 9 is heated by the load 3, at least a part of the aerosol-forming substrate 9a and the flavor source or the aerosol source is consumed, so that the heat capacity of the aerosol generation article 9 tends to decrease with the progressing of the use phase. In other words, it is assumed that the heat capacity of the aerosol generation article 9 indicates an amount of aerosols that can be generated by the aerosol generation article 9, a remaining amount of aerosols that can be inhaled by the user of the aerosol generation device 1, the number of times of remaining inhalation or an amount of heat that can be applied to the aerosol generation article 9 by the aerosol generation device 1. In the meantime, it should be noted that, even when an amount of aerosols that can be generated by the aerosol generation article 9, a remaining amount of aerosols that can be inhaled by the user of the aerosol generation device 1 or the number of times of remaining inhalation is zero, the heat capacity of the aerosol generation article 9 is not zero.

The control unit 8 and/or the limiter change unit 13 in accordance with Example 2B may determine whether the heat capacity of the aerosol generation article 9 is larger than expected with the time-series progressing of the use phase, based on the measured temperature value or the puff profile. As an example, the control unit 8 and/or the limiter change unit 13 in accordance with Example 2B stores in advance ideal time-series data about the temperature of the load 3 or the aerosol generation article 9 in the use phase, the number of times of inhalation by the user of the aerosol generation device 1 in the use phase or an integrated value of the amount of inhalation. By comparing the ideal time-series data and the measured temperature value or the puff profile, it may be determined whether the heat capacity of the aerosol generation article 9 is greater than expected with the time-series progressing of the use phase.

Specifically, when the measured temperature value is delayed with respect to the ideal time-series data, the control unit 8 and/or the limiter change unit 13 may determine that the heat capacity of the aerosol generation article 9 is greater than expected. On the other hand, when the measured temperature value is progressing with respect to the ideal time-series data, the control unit 8 and/or the limiter change unit 13 may determine that the heat capacity of the aerosol generation article 9 is less than expected.

In other words, in a state where the heat capacity of the aerosol generation article 9 is large, it is estimated that the measured temperature value is small. On the other hand, in a state where the heat capacity of the aerosol generation article 9 is not large (is small), it is estimated that the measured temperature value is large.

When the measured temperature value is small, the limiter change unit 13 expands the increase width of the limiter width.

When the measured temperature value is large, the limiter change unit 13 narrows the increase width of the limiter width.

In the meantime, when the puff profile is delayed with respect to the ideal time-series data, the control unit 8 and/or the limiter change unit 13 may determine that the heat capacity of the aerosol generation article 9 is larger than expected. In this case, as can be clearly seen from the delay of the puff profile, the user does not inhale the aerosol generation device 1 more than expected. Therefore, it should be noted that it is less necessary to expand the increase width of the limiter width so as to increase or keep the amount of aerosols that are generated from the aerosol generation article 9 by expanding the increase width of the limiter width.

Also, when the puff profile progresses with respect to the ideal time-series data, the control unit 8 and/or the limiter change unit 13 may determine that the heat capacity of the aerosol generation article 9 is smaller than expected. In this case, as can be clearly seen from the progressing of the puff profile, the user inhales the aerosol generation device 1 more than expected, Therefore, it should be noted that it is necessary to positively expand the increase width of the limiter width so as to increase or keep the amount of aerosols that are generated from the aerosol generation article 9 by expanding the increase width of the limiter width.

When the puff profile is delayed, the limiter change unit 13 narrows the increase width of the limiter width.

When the puff profile progresses, the limiter change unit 13 expands the increase width of the limiter width.

In the meantime, as described above, even when any of the measured temperature value and the puff profile is used for the degree of progress of the use phase, in Example 2B, the limiter change unit 13 does not narrow the limiter width with the progressing of the use phase.

Figure 20:
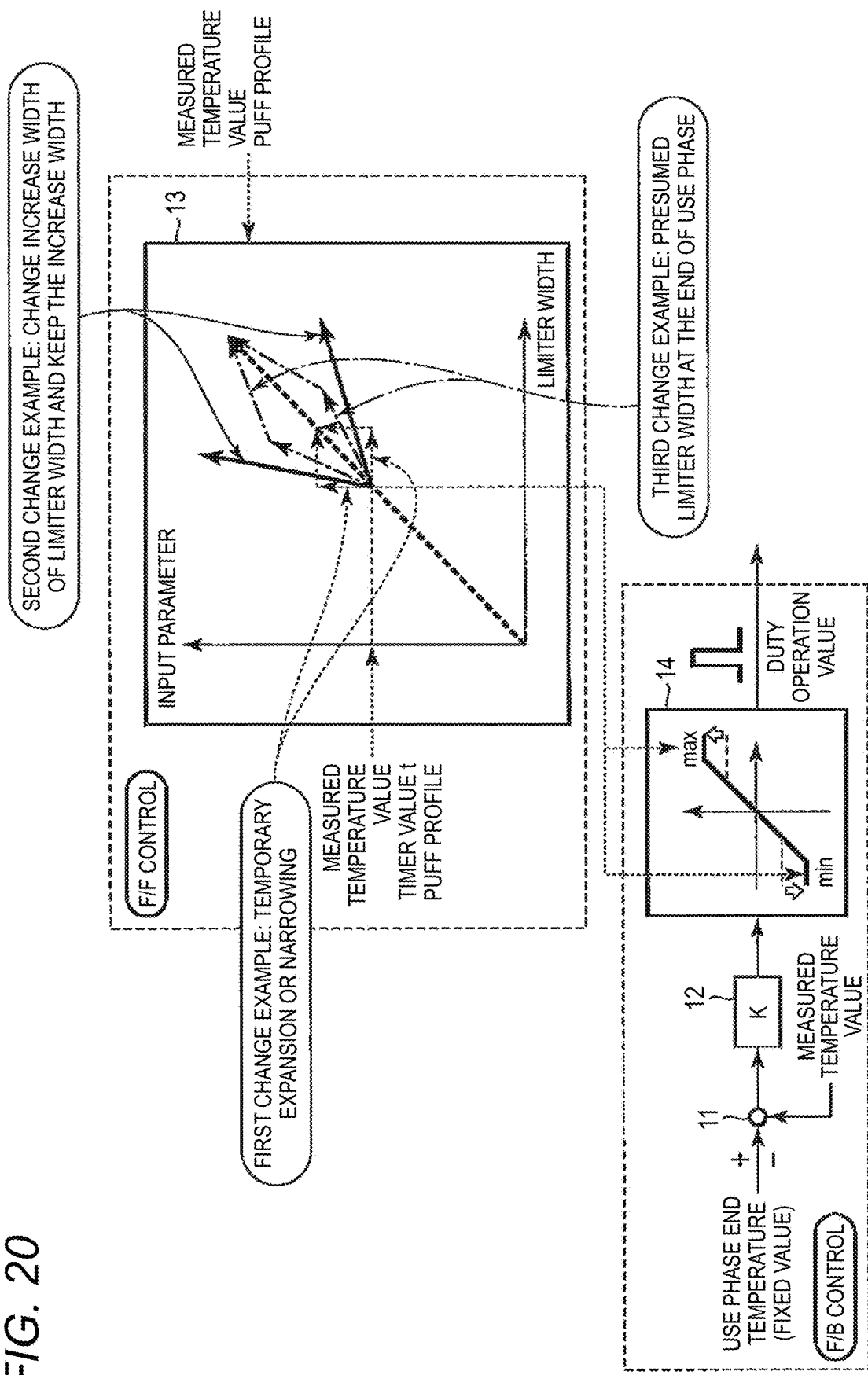
FIG. 20 is a control block diagram depicting an example of changing a limiter width in a limiter change unit in accordance with Example 2B.

FIG. 20 depicts an example of changing the limiter width in the limiter change unit 13 in accordance with Example 2B. In FIG. 20, the upward-sloping broken line indicates the increase width of the limiter width before change. In a first change example of the limiter width shown with the dotted line in FIG. 20, the limiter change unit 13 expands or narrows temporarily the increase width of the limiter width, based on the input parameter, and then returns the increase width of the limiter width to the state before change shown with the upward-sloping broken line in FIG. 20. In the meantime, it should be noted that the limiter change unit 13 does not output the increase width of the limiter width before change shown with the broken line, in an area in which the limiter width shown with the dotted line in the first change example of the limiter width is applied.

In a second change example of the limiter width shown with the solid line in FIG. 20, the limiter change unit 13 expands or narrows the increase width of the limiter width, based on the input parameter, and then maintains the change of the limiter width by the increase width. In other words, in the second change example, intercepts of the function including the limiter width and the input parameter are uniformly changed.

In a third change example of the limiter width shown with the dashed-dotted line in FIG. 20, the limiter change unit 13 expands or narrows the increase width of the limiter width, based on the input parameter, and then changes the increase width of the limiter width so as to be a limiter width expected at the end of the use phase.

Figure 21:
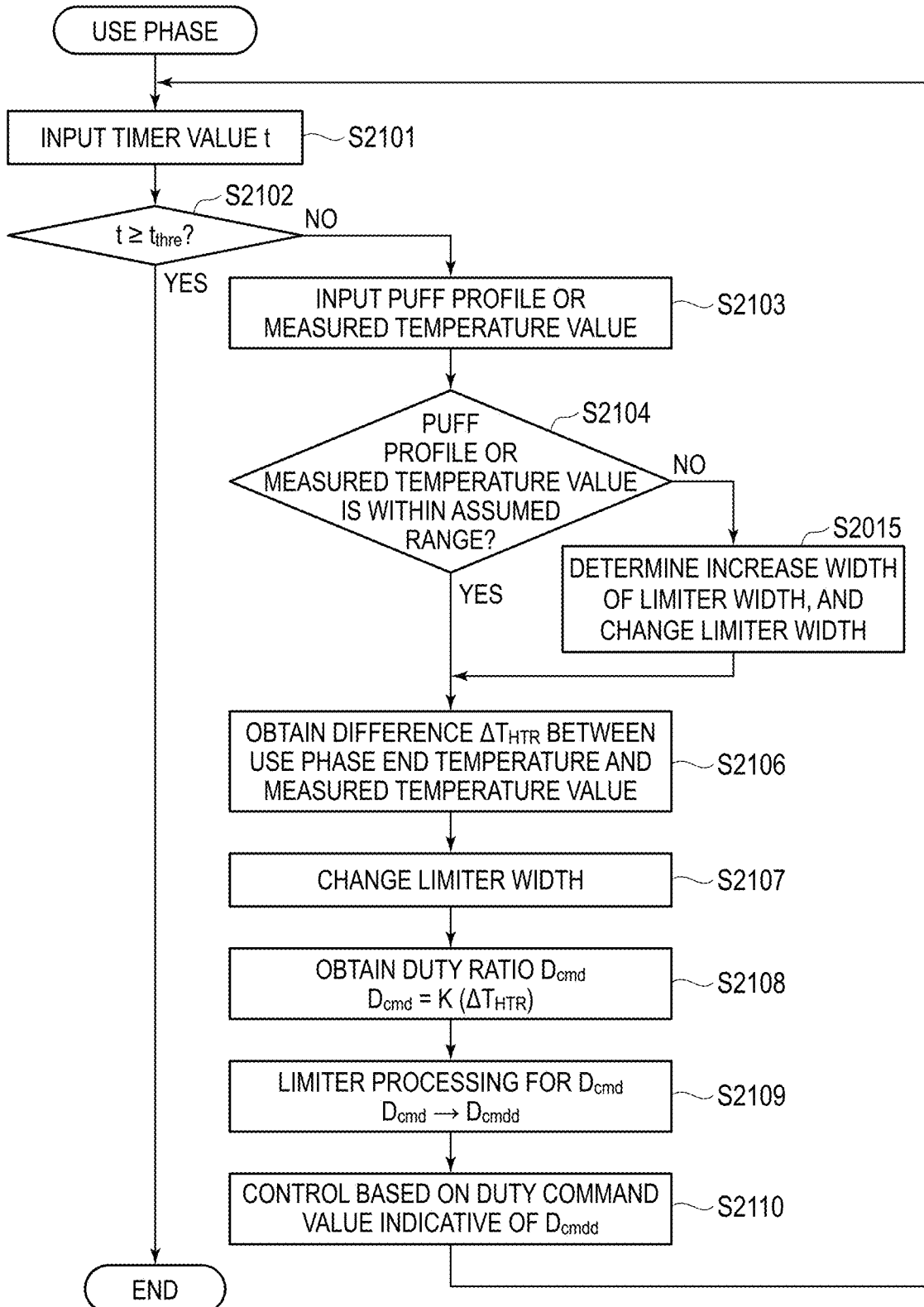
FIG. 21 is a flowchart depicting an example of processing in the use phase by the control unit 8 in accordance with Example 2B.

FIG. 21 is a flowchart depicting an example of processing in the use phase by the control unit 8 in accordance with Example 2B. In FIG. 21, a case where the increase width of the limiter width is determined based on the puff profile or the measured temperature value and the limiter width is changed based on the determined increase width is exemplified.

The processing of step S2101 and step S2102 is the same as the processing of step S1901 and step S1902 in FIG. 19.

When it is determined in step S2102 that the tinier value t is not equal to or greater than time $t_{thre}$ (a determination result is negative), the puff profile or the measured temperature value is input to the limiter change unit 13 in step S2103, for example.

In step S2104, the limiter change unit 13 determines whether the input puff profile or measured temperature value is within an assumed range (within a predetermined range). In the meantime, the description "the input puff profile or measured temperature value is within an assumed range" indicates that there is no deviation between the ideal time-series data and the input puff profile or measured temperature value or there is a slight deviation.

When it is determined that the puff profile or the measured temperature value is within the assumed range (a determination result in step S2104 is affirmative), the processing proceeds to step S2106.

When it is determined that the puff profile or the measured temperature value is not within the assumed range (a determination result in step S2104 is negative), the limiter change unit 13 changes the increase width of the limiter width in step S2105, and the processing proceeds to step S2106.

The processing from step S2106 to step S2110 is the same as the processing from step S1903 to step S1907 in FIG. 19.

The operational effects of Example 2B described above are described.

The user's aerosol inhalation pace by the aerosol generation device 1 is different depending on users. Also, there is an inevitable product error between the aerosol generation device 1 and/or the aerosol generation article 9. In Example 2B, in order to resolve/absorb the error based on the user's aerosol inhalation pace and the product error, the increase width of the limiter width that is used in the limiter unit 14 is changed based on the degree of progress of the use phase. Thereby, it is possible to stabilize the control on the aerosol generation.

Example 2C

It is possible to suppress the aerosol generation article 9 from being overheated by suppressing the time period in which the load 3 is at high temperatures, for example.

In the meantime, it is possible to promote the aerosol generation in a position of the aerosol generation article 9 distant from the load 3 by prolonging the time period in which the load 3 is at high temperatures.

Therefore, in Example 2C, it is described that the increase width of the limiter width is expanded or narrowed and the temperature of the load 3 is controlled, so as to suppress the aerosol generation article 9 from being overheated or to promote the aerosol generation.

In order to stably generate aerosols over the entire use phase, it is necessary to generate aerosols from a position of the aerosol generation article 9 distant from the load 3 over time from the start of aerosol generation.

As described above, when a position of the aerosol generation article 9 distant from the load 3 is subjected to a temperature suitable for aerosol generation, it is necessary to put the load 3 in higher temperatures than at the start of aerosol generation.

The control unit 8 performs control so that the load 3 is at the use phase end temperature at the end of the use phase. However, it is possible to suppress the load 3 from being overheated as a time period in which the load is maintained at the use phase end temperature is shorter.

In the meantime, there is a case where the load 3 is preferably at high temperatures for a long time so as to generate a sufficient amount of aerosols even in a position distant from the load 3.

Figure 22:
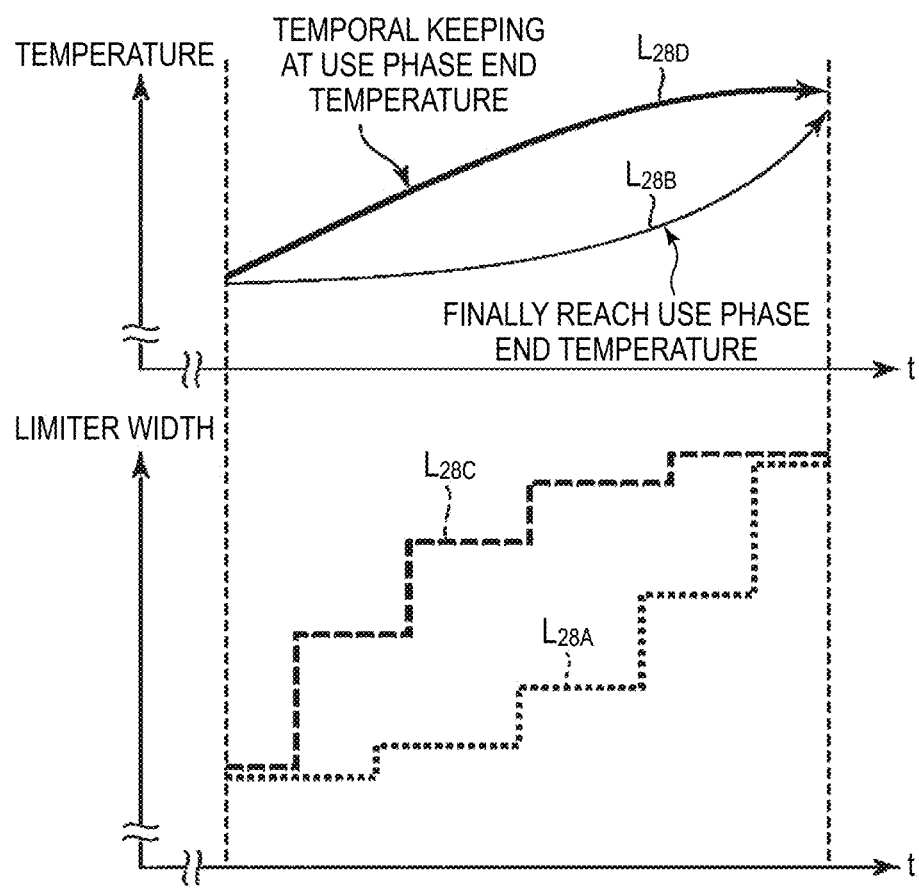
FIG. 22 is a graph depicting an example of a change in limiter width that is used in the limiter unit and a state of increase in temperature of the load.

FIG. 22 is a graph depicting an example of a change in the limiter width that is used in the limiter unit 14 and a state of increase in temperature of the load 3. In FIG. 22, the horizontal axis indicates the timer value t. The vertical axis indicates the temperature or the limiter width.

A line $L_{28A}$ indicates that the smaller the timer value (time) t is, the smaller the increase width of the limiter width is, and the larger the timer value t is, the larger the increase width of the limiter width is. A change in temperature corresponding to the line $L_{28A}$ is a line $L_{28B}$. The line $L_{28B}$ shows that an increase in temperature of the load 3 is slow and the temperature of the load 3 increases as it comes close to the end of the use phase. The limiter change unit 13 can prevent an overheated state of the load 3 by changing the increase width of the limiter width so as to follow the line $L_{28A}$ and the line $L_{28B}$.

In the meantime, a line $L_{28C}$ indicates that the smaller the tinier value (time) t is, the larger the increase width of the limiter width is, and the larger the timer value t is, the smaller the increase width of the limiter width is. A change in temperature corresponding to the line $L_{28C}$ is a line $L_{28D}$. The line USD shows that an increase in temperature of the load 3 is fast and the time period in which the temperature of the load 3 is maintained near the use phase end temperature is prolonged. The limiter change unit 13 can generate a sufficient amount of aerosols from a position of the aerosol generation article 9 distant from the load 3 by changing the increase width of the limiter width so as to follow the line $L_{28C}$ and the line $L_{28D}$.

Figure 23:
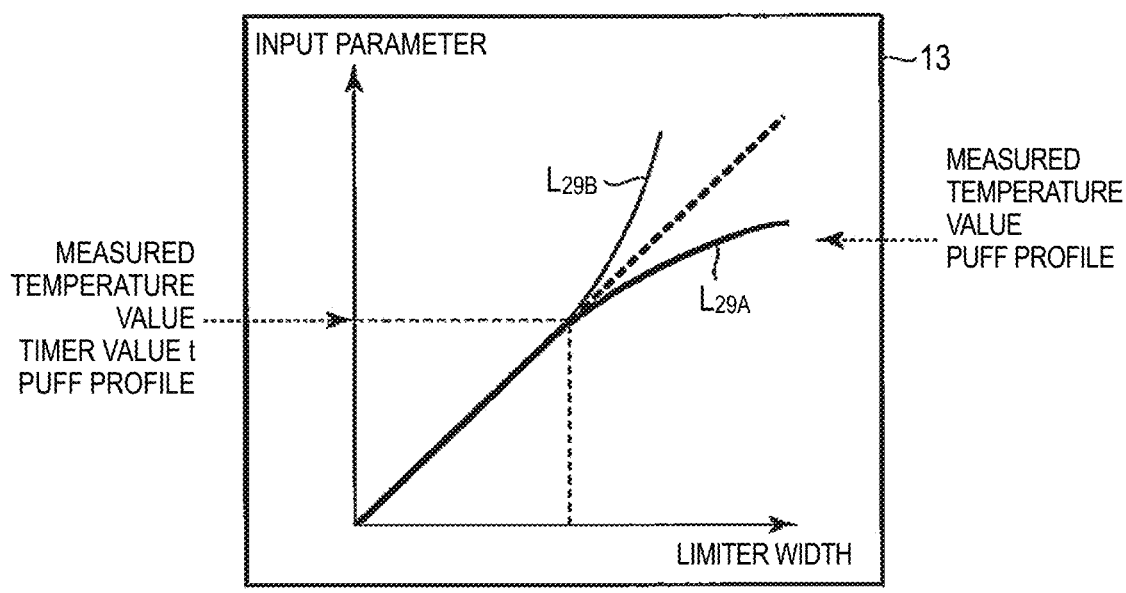
FIG. 23 is a graph depicting an example of a change in the limiter width in accordance with Example 2C.

FIG. 23 is a graph depicting an example of a change in the limiter width in accordance with Example 2C.

The limiter change unit 13 changes the limiter width, based on the timer value tin principle, for example, and determines the increase width of the limiter width at the time of changing the limiter width, based on at least one of the puff profile and the measured temperature value.

A line $L_{29A}$ indicates an expanded state of the increase width of the limiter width, and a line $L_{29B}$ indicates a narrowed state of the increase width of the limiter width.

In Example 2C described above, the increase width of the limiter width is changed according to the degree of progress, thereby suppressing the load 3 from being overheated.

Also, in Example 2C, it is possible to effectively generate aerosols in the position of the aerosol generation article 9 distant from the load 3.

Example 2D

In Example 2A to Example 2C, the limiter change unit 13 changes the limiter width that is used in the limiter unit 14.

In contrast, in Example 2D, the gain of the gain unit 12 is changed based on the input parameter including at least one of the timer value t, the temperature of the load 3 and the puff profile.

Figure 24:
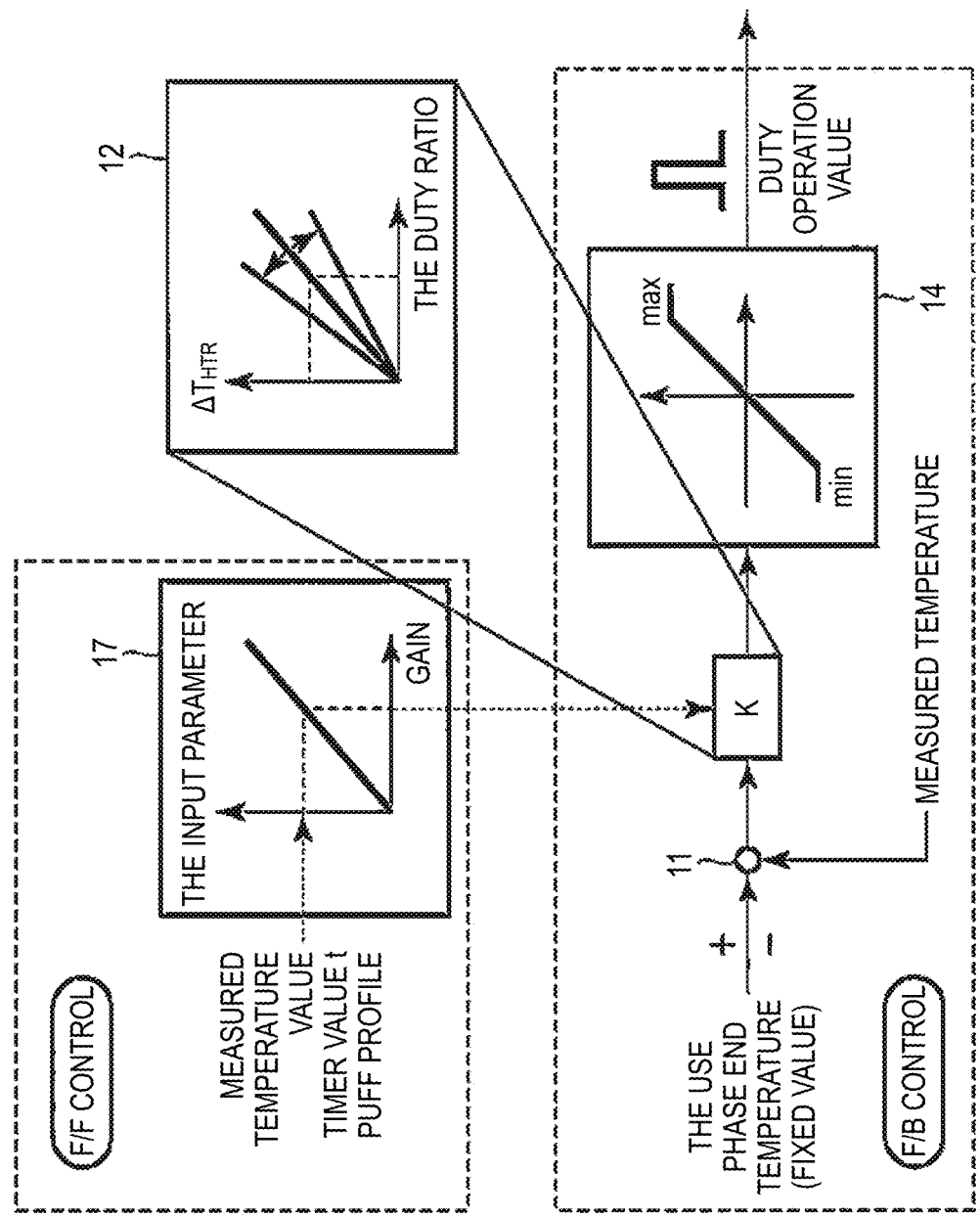
FIG. 24 is a control block diagram depicting an example of control that is executed by the control unit in accordance with Example 2D.

FIG. 24 is a control block diagram depicting an example of control that is executed by the control unit 8 in accordance with Example 2D.

A gain change unit 17 provided in the control unit 8 in accordance with Example 2D changes a gain that is used in the gain unit 12, based on the input parameter including at least one of the timer value t, the measured temperature value and the puff profile. The change of the gain includes a change of a control characteristic, a change of a gain function and a change of a value included in a gain function, for example. The gain function has a second relation in which a difference between the use phase end temperature and the measured temperature value and a duty ratio corresponding to the difference are associated with each other, for example.

When the gain change unit 17 changes a gain that is used in the gain unit 12, based on the input parameter, a duty ratio that is obtained based on the difference input from the differential unit 11 can be changed.

Figure 25:
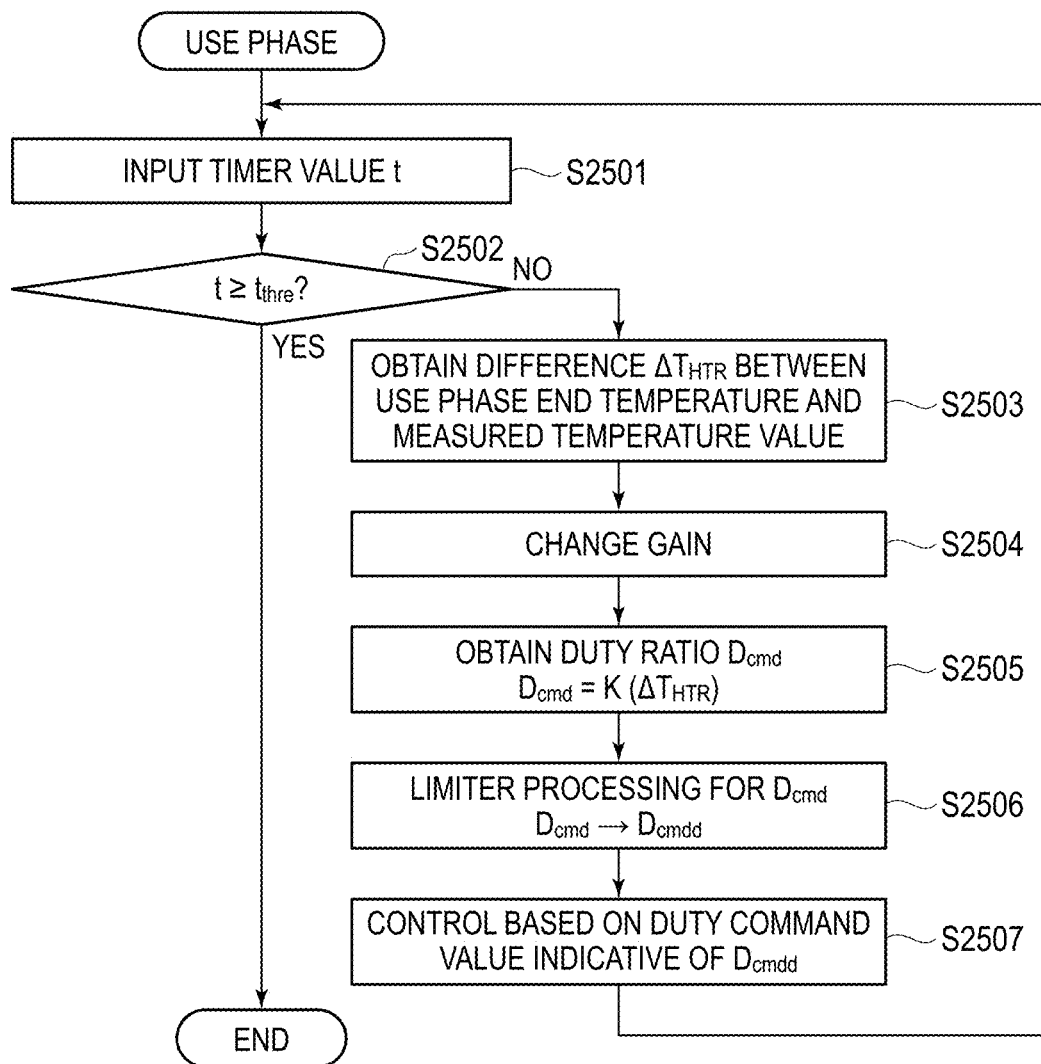
FIG. 25 is a flowchart depicting an example of processing in the use phase by the control unit in accordance with Example 2D.

FIG. 25 is a flowchart depicting an example of processing in the use phase by the control unit 8 in accordance with Example 2D.

The processing from step S2501 to step S2503 is the same as the processing from step S1901 to step S1903 in FIG. 19.

In step S2504, the gain change unit 17 of the control unit 8 changes a gain of the gain unit 12, based on the input parameter.

The processing from step S2505 to step S2507 is the same as the processing from step S1905 to step S1907 in FIG. 19.

In Example 2D as described above, the gain of the gain unit 12 other than the limiter width of the limiter unit 14 is changed to stabilize the control on the aerosol generation.

Example 2E

In Example 2E, an end condition of the use phase is that the measured temperature value is equal to or greater than a predetermined temperature, and control of ending the use phase when the measured temperature value is equal to or greater than the predetermined temperature is described. Herein, for example, the predetermined temperature may be equal to or higher than the use phase end temperature of the load 3. The predetermined temperature may be the temperature of the load 3 that is necessary to generate aerosols from the aerosol source or the aerosol-forming substrate 9a included in the aerosol generation article 9 and located in the position most distant from load 3, as described above, for example.

Figure 26:
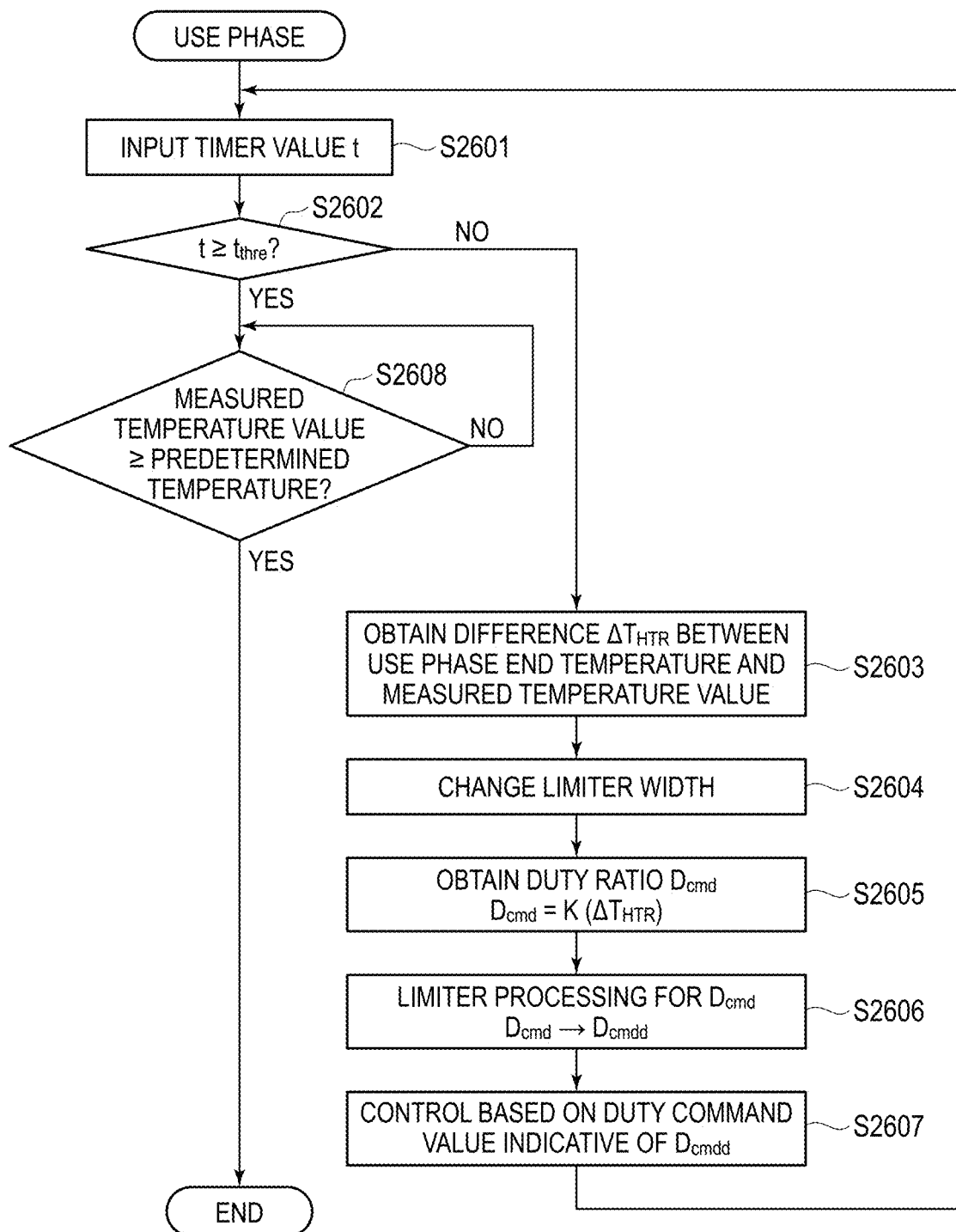
FIG. 26 is a flowchart depicting an example of the use phase by the control unit in accordance with Example 2E.

FIG. 26 is a flowchart depicting an example of processing in the use phase by the control unit 8 in accordance with Example 2E.

The processing from step S2601 to step S2607 is the same as the processing from step S1901 to step S1907 in FIG. 19.

When it is determined in step S2602 that the timer value t is equal to or greater than time $t_{thre}$ (a determination result is affirmative), the control unit 8 determines in step S2608 whether the measured temperature value is equal to or greater than the predetermined temperature.

When it is determined that the measured temperature value is equal to or greater than the predetermined temperature (a determination result in step S2608 is affirmative), the control unit 8 stops the supply of power to the load 3 and ends the use phase.

When it is determined that the measured temperature value is not equal to or greater than the predetermined temperature (a determination result in step S2608 is negative), the control unit S repeats step S2608.

In Example 2E as described above, when the measured temperature value is equal to or greater than the predetermined temperature, the use phase is ended.

Particularly, in Example 2E, as the end condition of the use phase, the condition where the timer value t is equal to or greater than time $t_{thre}$ and the measured temperature value is equal to or greater than the predetermined temperature is used.

Thereby, the end condition is strictly set, so that it is possible to generate more aerosols from the aerosol generation article 9 while suppressing the aerosol generation article 9 from being overheated.

In the meantime, as the end condition of the use phase, the condition where the timer value t is equal to or greater than time $t_{thre}$ may also be used, as described in Examples 2A to 2C.

Also, as the end condition of the use phase, any one of the condition where the timer value t is equal to or greater than time $L_{thre}$ and the condition where the measured temperature value is equal to or greater than the predetermined temperature may also be used. Thereby, it is possible to end the use phase safely and securely, thereby suppressing the aerosol generation article 9 from being overheated.

Example 2F

In Example 2F, features of the control by the control unit 8 in the use phase in the second embodiment are described.

Figure 27:
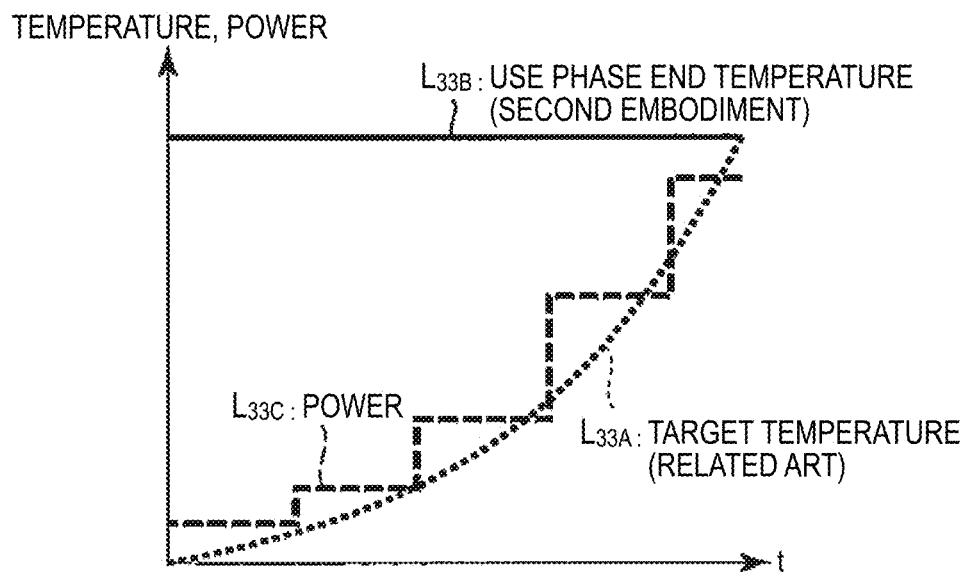
FIG. 27 is a graph depicting an example of comparison between a use phase end temperature in accordance with a second embodiment and a target temperature in accordance with an aerosol generation device of the related art.

FIG. 27 is a graph depicting an example of comparison between a use phase end temperature in accordance with the second embodiment and a target temperature in accordance with an aerosol generation device of the related art. In FIG. 27, the horizontal axis indicates the timer value t. The vertical axis indicates the temperature or the power. The power may also be indicated by the duty ratio, for example.

For example, in the aerosol generation device of the related art, as shown with a line $L_{33A}$, control of increasing the target temperature of the load 3 and/or the aerosol generation article 9 over time is executed.

In contrast, in the control that is executed by the control unit 8 of the second embodiment, as shown with a line $L_{33B}$, the use phase end temperature is constant, i.e., does not change. In the second embodiment, the increase width of the power that is supplied to the load 3 stepwise increases, as shown with a line $L_{33C}$.

In other words, in the control that is executed by the control unit 8 of the second embodiment, a rate of change in the power that is supplied to the load 3 with the progressing of the use phase is greater than a rate of change in the use phase end temperature with the progressing of the use phase.

Figure 28:
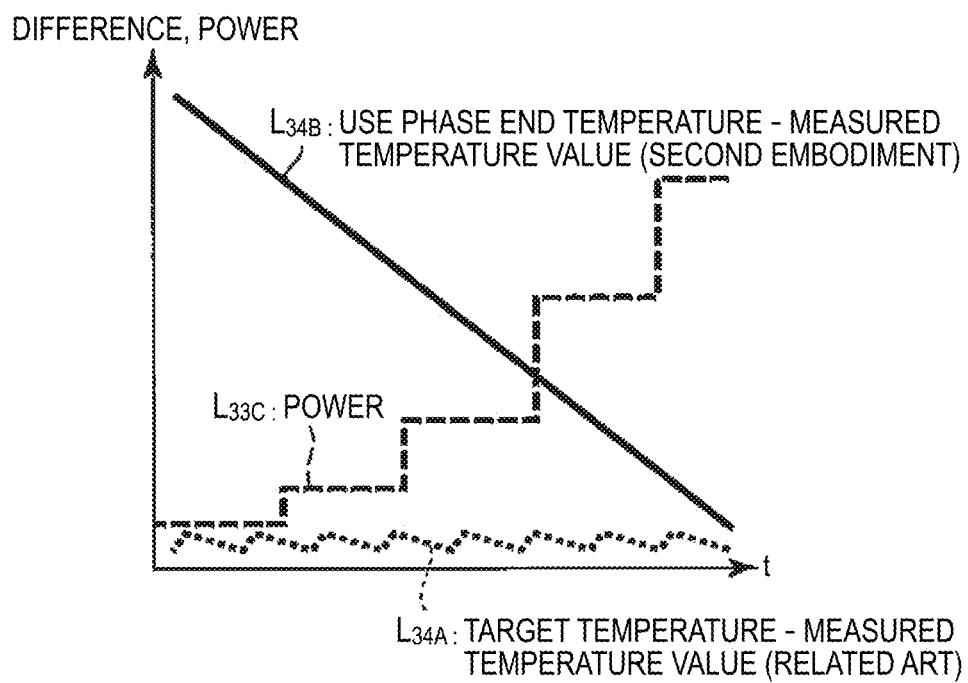
FIG. 28 is a graph depicting an example of comparison of a difference between the use phase end temperature and a measured temperature value in accordance with the second embodiment and a difference between the target temperature and a measured temperature value in accordance with the aerosol generation device of the related art.

FIG. 28 is a graph depicting an example of comparison of a difference between the use phase end temperature and the measured temperature value in accordance with the second embodiment and a difference between the target temperature and the measured temperature value in accordance with the aerosol generation device of the related art. In FIG. 28, the horizontal axis indicates the timer value t. The vertical axis indicates the difference or the power.

For example, in the aerosol generation device of the related art, as shown with a line $L_{34A}$, the temperature of the load 3 is immediately controlled so that a value obtained by subtracting the measured temperature value from the target temperature reduces.

In contrast, in the control that is executed by the control unit 8 of the second embodiment, as shown with a line $L_{34B}$, a value obtained by subtracting the measured temperature value from the use phase end temperature reduces as the timer value t increases, i.e., over time.

In this way, in the control that is executed by the control unit 8 of the second embodiment, the value obtained by subtracting the measured temperature value from the use phase end temperature reduces with the progressing of the use phase and the power that is supplied from the power source 4 to the load 3 increases with the progressing of the use phase at the same time.

Third Embodiment

In a third embodiment, a case where the aerosol generation device 1 executes different controls in multiple phases and the multiple phases includes a first phase that is first executed and a second phase that is executed later than the first phase is described.

The aerosol generation device 1 in accordance with the third embodiment includes the load 3 configured to heat the aerosol generation article 9 by using the power that is supplied from the power source 4, and the control unit 8 configured to control the power that is supplied from the power source 4 to the load 3 in multiple phases where different control modes are executed. The control modes are different in the multiple phases relating to the heating of the aerosol generation article 9, so that a control mode having a characteristic suitable for a phase can be used and the temperatures of the load 3 and the aerosol generation article 9, which is heated by the load 3, can be further highly controlled. Therefore, even with the aerosol generation article 9 having a complicated structure, it is possible to highly control aerosols to be generated.

As described in the first and second embodiments, for example, the control unit 8 may be configured to execute a first feed-forward control in the first phase and to execute at least feedback control of a second feed-forward control and the feedback control in the second phase. In this way, the control by the control unit 8 is shifted from the teed-forward control to the feedback control, so that it is possible to realize the high-speed temperature increase of the load 3 and the aerosol generation article 9 by the feed-forward control and the stable aerosol generation by the feedback control at the same time, which are conflicting effects.

The number of the control modes that are used in the second phase may be larger than the number of the control modes that are used in the first phase. Thereby, after the shift from the first phase to the second phase, it is possible to realize the stable aerosol generation by using the plurality of control modes.

An execution time of the first phase may be shorter than an execution time of the second phase where the rate of temperature increase of the load 3 is lower than in the first phase. Thereby, the execution time is shortened in the phase where the temperature increase of the load 3 and the aerosol generation article 9 is faster, so that it is possible to early generate aerosols.

The execution time of the first phase may be shorter than the execution time of the second phase where the temperature of the load or an average temperature of the load is higher than in the first phase. Thereby, the execution time is shortened in the phase where the temperatures of the load 3 and the aerosol generation article 9 or the average temperatures of the load 3 and the aerosol generation article 9 are lower, so that it is possible to early generate aerosols.

An amount of power that is supplied from the power source 4 to the load 3 in the first phase may be smaller than an amount of power that is supplied from the power source 4 to the load 3 in the second phase where the rate of temperature increase of the load 3 is lower than in the first phase. Thereby, an amount of power to be consumed is reduced in the phase where the rate of temperature increase of the load 3 and the aerosol generation article 9 is higher, so that it is possible to improve use efficiency of the power source 4 for aerosol generation.

The amount of power that is supplied from the power source 4 to the load 3 in the first phase may be smaller than the amount of power that is supplied from the power source 4 to the load 3 in the second phase where the temperature of the load or an average temperature of the load is higher than in the first phase. Thereby, an amount of power to be consumed is reduced in the phase where the temperatures of the load 3 and the aerosol generation article 9 or the average temperatures of the load 3 and the aerosol generation article 9 are lower, so that it is possible to improve the use efficiency of the power source 4 for aerosol generation.

The power that is supplied from the power source 4 to the load 3 in the first phase may be more than the power that is supplied from the power source 4 to the load 3 in the second phase where the rate of temperature increase of the load 3 is lower than in the first phase. In this way, the power that is consumed in the first phase is more than the power that is consumed in the second phase, so that it is possible to quickly generate aerosols in the first phase, to stably generate a preferable amount of aerosols in the second phase and to suppress the power that is consumed in the second phase.

The power that is supplied from the power source 4 to the load 3 in the first phase may be more than the power that is supplied from the power source 4 to the load 3 in the second phase where the temperature of the load or an average temperature of the load is higher than in the first phase. In this way, the power that is consumed in the first phase is more than the power that is consumed in the second phase, so that it is possible to quickly generate aerosols in the first phase, to stably generate a preferable amount of aerosols in the second phase and to suppress the power that is consumed in the second phase.

The rate of temperature increase of the load 3 in the second phase may be lower than the rate of temperature increase of the load 3 in the first phase, and the number of conditions of ending the second phase when satisfied may be larger than the number of conditions of ending the first phase when satisfied. Thereby, it is possible to stably end the aerosol generation.

The rate of temperature increase of the load 3 in the second phase may be lower than the rate of temperature increase of the load 3 in the first phase, and the number of end conditions that should be satisfied so as to end the second phase may be larger than the number of end conditions that should be satisfied so as to end the first phase. Thereby, since the end of the second phase is more carefully determined, it is possible to sufficiently secure the time during which the second phase is executed, thereby generating more aerosols from the aerosol generation article 9.

The temperature or average temperature of the load 3 in the second phase may be higher than the temperature or average temperature of the load 3 in the first phase, and the number of conditions of ending the second phase when satisfied may be larger than the number of conditions of ending the first phase when satisfied. Thereby, it is possible to stably end the aerosol generation.

The temperature or average temperature of the load 3 in the second phase may be higher than the temperature or average temperature of the load 3 in the first phase, and the number of end conditions that should be satisfied so as to end the second phase may be larger than the number of end conditions that should be satisfied so as to end the first phase. Thereby, since the end of the second phase is more carefully determined, it is possible to sufficiently secure the time during which the second phase is executed, thereby generating more aerosols from the aerosol generation article 9.

The multiple phases include the first phase, and the second phase where the rate of temperature increase of the load 3 is lower than in the first phase, and the number of variables that are acquired by the control unit 8 before execution of the first phase or before the increase in temperature of the load 3 in the first phase and are used in the control on the power that is supplied from the power source 4 to the load 3 in the first phase may be larger than the number of variables that are acquired by the control unit 8 before execution of the second phase or before the increase in temperature of the load 3 in the second phase and are used in the control on the power that is supplied from the power source 4 to the load 3 in the second phase. Thereby, environment settings at the start of the phase increase in the phase where the rate of temperature increase is higher, so that it is possible to increase the temperatures of the load 3 and the aerosol generation article 9 more stably and faster.

The multiple phases includes a phase where the rate of temperature increase of the load 3 is the lowest, and the control unit 8 may not acquire variables that are used in the control on the power that is supplied from the power source 4 to the load 3 in the lowest phase before execution of the lowest phase or before the increase in temperature of the load 3 in the lowest phase or may not execute the control on the power that is supplied from the power source 4 to the load 3 in the lowest phase, based on variables acquired before execution of the lowest phase or before the increase in temperature of the load 3 in the lowest phase. Thereby, since it is possible to omit the acquisition of variables for the phase where the rate of temperature increase is the lowest, it is possible to promptly execute the phase where the rate of temperature increase is the lowest. Also, it is possible to simplify the control on the phase where the rate of temperature increase is the lowest.

The multiple phases include the first phase, and the second phase where the temperature or average temperature of the load 3 is higher than in the first phase, and the number of variables that are acquired by the control unit 8 before execution of the first phase or before the increase in temperature of the load 3 in the first phase and are used in the control on the power that is supplied from the power source 4 to the load 3 in the first phase may be larger than the number of variables that are acquired by the control unit 8 before execution of the second phase or before the increase in temperature of the load 3 in the second phase and are used in the control on the power that is supplied from the power source 4 to the load 3 in the second phase. Thereby, environment settings at the start of the phase increase in the phase where the rate of temperature increase is higher, so that it is possible to increase the temperatures of the load 3 and the aerosol generation article 9 more stably and faster.

The multiple phases include a phase where the temperature or average temperature of the load 3 is highest, and the control unit 8 may not acquire variables that are used in the control on the power that is supplied from the power source 4 to the load 3 in the highest phase before execution of the highest phase or before the increase in temperature of the load 3 in the highest phase or may not execute the control on the power that is supplied from the power source 4 to the load 3 in the highest phase, based on variables acquired before execution of the highest phase or before the increase in temperature of the load 3 in the highest phase. Thereby, since it is possible to omit the acquisition of variables for the phase where the temperature or average temperature is the highest, it is possible to promptly execute the phase where the temperature or average temperature is the highest. Also, it is possible to simplify the control on the phase where the temperature or average temperature is the highest.

The rate of temperature increase of the load 3 in the second phase may be lower than the rate of temperature increase of the load 3 in the first phase, and the number of times of changing variables and/or algorithms that are used in the control on the second phase during control execution of the second phase may be larger than the number of times of changing variables and/or algorithms that are used in the control on the first phase during control execution of the first phase. Thereby, the number of change times during the phase increases in the phase where the rate of temperature increase of the load 3 is lower, so that the temperatures of the load 3 and the aerosol generation article 9 can be further highly controlled to stably generate aerosols.

Herein, the change of variables that are used in the control includes changing one variable to another variable and changing a value stored in a variable, for example.

The change of algorithm includes changing one algorithm to another algorithm, changing a function, processing and a variable that are used in an algorithm, changing a part of a function and changing a part of processing, for example.

The control unit 8 may be configured not to change a variable and/or an algorithm that is used in the control on a phase of the multiple phases where the rate of temperature increase of the load 3 is the highest, during control execution of the highest phase. Thereby, it is possible to omit the acquisition of variables for the phase where the rate of temperature increase is the highest, and to simplify the control on the phase where the rate of temperature increase is the highest.

The temperature or average temperature of the load 3 in the second phase may be higher than the temperature or average temperature of the load 3 in the first phase, and the number of times of changing variables and/or algorithms that are used in the control on the second phase during control execution of the second phase may be larger than the number of times of changing variables and/or algorithms that are used in the control on the first phase during control execution of the first phase. Thereby, the number of change times during the phase increases in the phase where the temperature or average temperature of the load 3 is higher, so that the temperatures of the load 3 and the aerosol generation article 9 can be further highly controlled to stably generate aerosols.

The control unit 8 may be configured not to change a variable and/or an algorithm that is used in the control on a phase of the multiple phases where the temperature or average temperature of the load 3 is the lowest, during control execution of the lowest phase. Thereby, since it is possible to omit the acquisition of variables for the phase where the temperature or average temperature is the lowest, it is possible to promptly execute the phase where the temperature or average temperature is the lowest. Also, it is possible to simplify the control on the phase where the temperature or average temperature is the lowest.

The rate of temperature increase of the load 3 in the second phase may be lower than the rate of temperature increase of the load 3 in the first phase, the control unit 8 may be configured to detect inhalation of aerosols generated from the aerosol generation article 9, and the increase width of the power that is supplied from the power source 4 to the load 3 in accordance with the inhalation detected in the second phase may be set greater than the increase width of the power that is supplied from the power source 4 to the load 3 in accordance with the inhalation detected in the first phase. Thereby, the temperature can be recovered with a larger increase width with respect to the decrease in temperature due to the inhalation in the phase where the rate of temperature increase of the load 3 is lower, so that it is possible to suppress the amount of aerosol generation and the temperature of the load 3 from being lowered due to the inhalation.

The temperature or average temperature of the load 3 in the second phase may be higher than the temperature or average temperature of the load 3 in the first phase, the control unit 8 may be configured to detect inhalation of aerosols generated from the aerosol generation article 9, and the increase width of the power that is supplied from the power source 4 to the load 3 in accordance with the inhalation detected in the second phase may be set greater than the increase width of the power that is supplied from the power source 4 to the load 3 in accordance with the inhalation detected in the first phase. Thereby, the temperature can be recovered with a larger increase width with respect to the decrease in temperature due to the inhalation in the phase where the temperature or average temperature of the load 3 is higher, so that it is possible to suppress the amount of aerosol generation and the temperature of the load 3 from being lowered due to the inhalation.

The control unit 8 may be configured to obtain degrees of progress, based on different variables, for each of the multiple phases. In this way, a variable corresponding to the degree of progress is changed for each phase, so that it is possible to recognize the progress of phase more appropriately.

The control unit 8 may be configured to obtain a degree of progress of a phase of the multiple phases where the rate of temperature increase of the load 3 is the highest, based on time. In this way, it is possible to suppress the load 3 from being overheated by determining temporally the degree of progress of the phase where the rate of temperature increase is high.

The control unit 8 may be configured to obtain a degree of progress of a phase of the multiple phases where the temperature or average temperature of the load 3 is the lowest, based on time. In this way, it is possible to suppress the load 3 from being overheated by determining temporally the degree of progress of the phase where the temperature or average temperature of the load 3 is the lowest.

The control unit 8 may be configured to detect inhalation of aerosols generated from the aerosol generation article 9, and to obtain a degree of progress of a phase of the multiple phases where the rate of temperature increase of the load 3 is the lowest, based on the temperature of the load 3 or the inhalation. In this way, the degree of progress is determined based on the temperature of the load 3 or the inhalation, so that the degree of progress of the phase can be determined based on a result of the aerosol generation of the aerosol generation article 9. Therefore, it is possible to generate more aerosols from the aerosol generation article 9.

The control unit 8 may be configured to detect inhalation of aerosols generated from the aerosol generation article 9, and to obtain a degree of progress of a phase of the multiple phases where the temperature or average temperature of the load 3 is the highest, based on the temperature of the load 3 or the inhalation. In this way, the degree of progress is determined based on the temperature of the load 3 or the inhalation in the phase where the temperature or average temperature is the highest, so that the degree of progress of the phase can be determined based on a result of the aerosol generation of the aerosol generation article 9. Therefore, it is possible to generate more aerosols from the aerosol generation article 9.

The control unit 8 may be configured to execute the feedback control in the multiple phases where the target temperatures are different, and to set at least one of the gain in the feedback control and the upper limit value of the power that is supplied from the power source 4 to the load 3 different in each of the multiple phases. The control modes in the multiple phases relating to the heating are different, so that a control mode having a characteristic suitable for a phase can be used and the temperatures of the load 3 and the aerosol generation article 9, which is heated by the load 3, can be further highly controlled. Therefore, even with the aerosol generation article 9 having a complicated structure, it is possible to highly control aerosols to be generated.

In the third embodiment, the use phase may be further divided into multiple phases, and the multiple phases may include the first phase and the second phase.

In this case, the target temperature of the first phase may be lower than the target temperature of the second phase, and at least one of the gain and the upper limit value that are used in the first phase by the control unit 8 may be set greater than at least one of the gain and the upper limit value that are used in the second phase by the control unit 8. Thereby, at least one of the gain and the upper limit value can be increased in the phase where the target temperature is lower. Also, in the first phase, the rate of temperature increase of the load 3 can be highly controlled according to the target temperature by the feedback control, instead of the feed-forward control.

A change width of the temperature of the load 3 in the first phase may be larger than a change width of the temperature of the load 3 in the second phase, and at least one of the gain and the upper limit value that are used in the first phase by the control unit 8 may be set greater than at least one of the gain and the upper limit value that are used in the second phase by the control unit 8. Thereby, at least one of the gain and the upper limit value can be increased in the phase where the change width of the temperature of the load 3 is larger. Also, in the first phase, the rate of temperature increase of the load 3 can be highly controlled according to the target temperature by the feedback control, instead of the feed-forward control.

The target temperature of the second phase may be higher than the target temperature of the first phase, and a change width of at least one of the gain and the upper limit value that are used in the first phase by the control unit 8 may be set smaller than a change width of at least one of the gain and the upper limit value that are used in the second phase by the control unit 8. Thereby, the change width of at least one of the gain and the upper limit value can be increased in the phase where the target temperature is higher. Also, in the first phase, the rate of temperature increase of the load 3 can be highly controlled according to the target temperature by the feedback control, instead of the teed-forward control.

The change width of the temperature of the load 3 in the second phase may be smaller than the change width of the temperature of the load 3 in the first phase, and a change width of at least one of the gain and the upper limit value that are used in the first phase by the control unit 8 may be set smaller than at least one of the gain and the upper limit value that are used in the second phase by the control unit 8. Thereby, the change width of at least one of the gain and the upper limit value can be increased in the phase where the change width of the temperature of the load 3 is smaller. Also, in the first phase, the rate of temperature increase of the load 3 can be highly controlled according to the target temperature by the feedback control, instead of the feed-forward control.

The control unit 8 may be configured to change at least one of the target temperature, the gain and the upper limit value of the power of the second phase, based on the degree of progress of the first phase. Thereby, it is possible to change a variable value of a later phase, based on a degree of progress of an earlier phase. Therefore, a smooth shift from the earlier phase to the later phase is possible.

The control unit 8 may be configured to execute the feedback control in the multiple phases, and to set different gains in the feedback control in each of the multiple phases. Thereby, it is possible to perform appropriate control in each phase by the feedback control.

The diverse controls by the control unit 8 may also be implemented as the control unit 8 executes a program.

FIG. 29 is a table showing comparison of the preparation phase and the use phase that are executed by the control unit in accordance with the third embodiment. As described above, the preparation phase is a phase corresponding to the preparation state where the load 3 cannot generate the predetermined amount or more of aerosols from the aerosol generation article 9, for example. Also, the use phase is a phase corresponding to the use state where the load 3 can generate the predetermined amount or more of aerosols from the aerosol generation article 9, for example. Therefore, in order to generate aerosols from the aerosol generation article 9, it is necessary for the control unit 8 to shift a phase to be executed in order from the preparation phase to the use phase.

As described in the first embodiment, the control mode that is used in the preparation phase is the feed-forward control. The end condition of the preparation phase is that a predetermined time elapses since the start of the preparation phase, for example.

In the preparation phase, the load 3 in the preparation state is shifted to the use state, and aerosols are quickly generated from the aerosol generation article 9. Therefore, the execution time of the preparation phase is shorter than the execution time of the use phase.

The preparation phase is provided so as to shift the load 3 in the preparation state to the use state. In the preparation phase, the aerosol generation is not required, and the power consumption per unit time in the preparation phase is larger than the power consumption per unit time in the use phase. In the meantime, since the preparation phase is preferably executed only for a short time, a total amount of power consumption over the entire preparation phase is smaller than a total amount of power consumption over the entire use phase.

In the feed-forward control that is used in the preparation phase, it is difficult to reflect a state of the control target in the control during execution of the control. Therefore, in the preparation phase, as described above, an environment setting of changing the control characteristic may be performed based on the measured temperature value at the start of the preparation phase, the charging rate of the power source 4, or the like. By the environment setting, the state of the load 3 and/or the aerosol generation article 9 at the end of the preparation phase can be made uniform.

In the preparation phase, the control variable (control parameter) or control function may be changed or may not be changed from a predetermined value or function before execution of the phase.

The preparation phase is provided so as to shift the load 3 in the preparation state to the use state. In the preparation phase, the aerosol generation is not required, and the inhalation by the user of the aerosol generation device 1 is not assumed in the preparation phase. Therefore, in the preparation phase, the recovery of the decrease in temperature due to the user's inhalation is not performed.

The preparation phase is preferably executed only for a short time for the purpose thereof. Therefore, as the input parameter of the feed-forward control that is executed in the preparation phase, the timer value t, i.e., the operating time is used. The operating time that increases securely over time is used as the input parameter, so that the preparation phase can be securely progressed to shorten the operating time as much as possible.

The change in the measured temperature value (temperature profile) in the preparation phase shows a more linear increase trend because it shifts the load 3 from the preparation state to the standby state in a time as short as possible.

In contrast, as described in the second embodiment, the control mode that is used in the use phase is the feedback control, and the feed-forward control may also be used partially.

Since one of purposes of the use phase is to generate more aerosols from the aerosol generation article 9, it is necessary to design more carefully the condition as to whether to end the use phase. Therefore, as the end condition of the use phase, for example, lapse of a predetermined time, reaching a predetermined temperature or lapse of a predetermined time and reaching a predetermined temperature are used.

The use phase is used so as to generate more aerosols from the aerosol generation article 9. Therefore, an execution time period of the use phase is longer than an execution time period of the preparation phase.

The load 3 is already in the use state upon execution of the use phase. Therefore, since it is not necessary to considerably increase the temperature of the load 3 in the use phase, as compared to the preparation phase, an amount of power that is used in the use phase is smaller than an amount of power that is used in the preparation phase and the power consumption in the use phase is less than the power consumption in the preparation phase. In the meantime, since it is necessary to generate many aerosols from the aerosol generation article 9 in the use phase, the total amount of power over the entire use phase is larger than the total amount of power in the preparation phase. Since the feedback control is mainly executed in the use phase, the environment setting at the start of the use phase may not be required or the measured temperature value at the end of the preparation phase may be used as the environment temperature.

In the use phase, for example, the control variable such as a gain may be changed to highly control the temperature of the load 3 and/or the temperature of the aerosol generation article 9.

In the use phase, since it is necessary to stabilize aerosols that are generated from the aerosol generation article 9, the recovery of the decrease in temperature due to the inhalation is executed.

When executing the feed-forward control in the use phase, the input parameter of the feed-forward control in the use phase may be any one of the timer value t, the measured temperature value and the puff profile or a combination thereof, for example. Since it is necessary to generate more aerosols from the aerosol generation article 9 in the use phase, it is necessary to further highly control the temperatures of the load 3 and the aerosol generation article 9. Therefore, it should be noted that the measured temperature value or the puff profile, which increases only when the phase progresses, can be used as the input parameter of the feed-forward control.

Since the temperature of the load 3 is controlled in the use phase so that the aerosol generation position of the aerosol generation article 9 changes over time, the temperature of the load 3 changes in a curve in the use phase.

In the third embodiment as described above, the feed-forward control is executed in the preparation phase and the feedback control is executed in the use phase, so that aerosols are generated. Therefore, for example, as compared to a case where only the feedback control is used, it is possible to improve the convenience for the user who inhales aerosols, to improve the power efficiency, and to stably generate aerosols.

Fourth Embodiment

In a fourth embodiment, a case where the power that is supplied to the load 3 is controlled using a larger value of an operation value obtained as a result of the feedback control in the use phase and a predetermined value is described. By the control, it is possible to suppress the decrease in temperature of the load 3 that occurs upon shift from the preparation phase to the use phase, for example.

The control unit 8 in accordance with the fourth embodiment is configured to determine the power that is supplied from the power source 4 to the load 3, based on comparison between an operation value obtained in the feedback control and a predetermined value, for example. For example, the predetermined value may be a minimum guaranteed value. Thereby, as compared to a case where there is no minimum guaranteed value, it is possible to suppress the temperatures of the load 3 and the aerosol generation article 9 from dropping sharply.

The control unit 8 may also be configured to determine the power that is supplied from the power source 4 to the load 3, based on a larger value of the operation value and the predetermined value. Thereby, it is possible to prevent a situation where the power that is supplied to the load 3 is controlled based on a value smaller than the predetermined value and thus the temperatures of the load 3 and the aerosol generation article 9 drop sharply.

The control unit 8 may be configured to control the power that is supplied from the power source 4 to the load 3 in the multiple phases, the multiple phases may include the first phase, and the second phase that is executed after the first phase, and the predetermined value that is used in the second phase may be determined based on the power that is supplied from the power source 4 to the load 3 in the first phase. In this way, the predetermined value that is used in the second phase is determined based on the power used in the first phase, so that it is possible to suppress the decrease in temperatures of the load 3 and the aerosol generation article 9 upon shift from the first phase to the second phase.

The predetermined value that is used in the second phase may also be determined based on a value relating to power that is finally determined in the first phase. In this way, the predetermined value that is used in the second phase is determined based on a value relating to power that is finally determined in the first phase, so that it is possible to efficiently suppress the decrease in temperatures of the load 3 and the aerosol generation article 9 upon shift from the first phase to the second phase.

The control unit 8 may be configured to execute the feedback control so that the temperature of the load 3 gradually increases, and the predetermined value may change with the increase in temperature of the load 3. In this case, since the minimum guaranteed value is changed as the phase progresses, it is possible to use the appropriate minimum guaranteed value corresponding to the phase progress. Therefore, even when the phase progresses, it is possible to suppress the temperature of the load 3 from dropping sharply.

The control unit 8 may also be configured to execute the feedback control so that the operation value gradually increases, and the predetermined value may change with the increase in temperature of the load 3. Thereby, even when the phase progresses and the temperature of the load 3 increases, it is possible to suppress the temperature of the load 3 from dropping sharply by using the appropriate minimum guaranteed value corresponding to the phase progress.

The control unit 8 may also be configured to gradually increase a gain in the feedback control. Thereby, it is possible to increase the operation value as the phase progresses. Therefore, since it is possible to increase the temperature of the load 3 and/or the aerosol generation article 9 according to the progress of the phase, it is possible to stably generate aerosols from the aerosol generation article 9 over the entire use phase, as described in the second embodiment.

The control unit 8 may also be configured to gradually increase the upper limit of the power that is supplied from the power source 4 to the load 3 in the feedback control. Thereby, it is possible to increase the operation value as the phase progresses. Therefore, since it is possible to increase the temperature of the load 3 and/or the aerosol generation article 9 according to the progress of the phase, it is possible to stably generate aerosols from the aerosol generation article 9 over the entire use phase, as described in the second embodiment.

The predetermined value may gradually decrease. In this case, it is possible to reduce the minimum guaranteed value with the phase progress. In particular, when the minimum guaranteed value is provided so as to suppress the decrease in temperature of the load 3 that occurs upon shift from the preparation phase to the use phase, the necessity to provide the minimum guaranteed value decreases with the phase progress. Therefore, it is possible to reduce an influence of the minimum guaranteed value on the control with the phase progress.

The control unit 8 may be configured to change the predetermined value to zero during the execution of the feedback control. In this case, it is possible to suppress an influence of the minimum guaranteed value on the control, which is not required as the phase progresses, as described above.

Herein, the change of the predetermined value to zero includes temporarily changing the predetermined value to zero.

The control unit 8 may decrease the predetermined value when an overshoot where the temperature of the load 3 changes by a threshold value or larger per predetermined time is detected. In this way, when the overshoot of the temperature of the load 3 is detected, the minimum guaranteed value is decreased to reduce an influence of the minimum guaranteed value on the operation value obtained by the feedback control that is executed by the control unit 8. Therefore, it is possible to early resolve the overshoot.

When the overshoot is resolved, he control unit 8 may return the predetermined value to a value before the overshoot is detected. Thereby, it is possible to return the minimum guaranteed value, based on the resolving of the overshoot, and to suppress the temperatures of the load 3 and the aerosol generation article 9 from dropping sharply after the overshoot is resolved.

The predetermined value may be determined as a value or larger necessary to keep the temperature of the load 3. Thereby, the minimum guaranteed value is determined so that the temperature of the load 3 is not decreased, so that it is possible to suppress the decrease in temperatures of the load 3 and the aerosol generation article 9.

The control unit 8 may also be configured to determine or correct the predetermined value, based on the temperature of the load 3. Thereby, since the minimum guaranteed value is determined or corrected based on the temperature of the load 3, the minimum guaranteed value becomes a value that reflects a state of the load 3, as compared to a case where the minimum guaranteed value is not determined or corrected. Therefore, it is possible to suppress the decrease in temperature of the load 3.

The control unit 8 may also be configured to determine or correct the predetermined value so that an absolute value of a difference between the temperature of the load 3 and the predetermined temperature does not increase. Thereby, since the minimum guaranteed value is determined or corrected so that the difference between the predetermined temperature and the temperature of the load 3 does not increase, the minimum guaranteed value becomes a value that reflects the progress of the use phase, as compared to a case where the minimum guaranteed value is not determined or corrected. Therefore, it is possible to suppress the decrease in temperature of the load 3.

The control unit 8 may also be configured to acquire the temperature of the load 3, to control the power that is supplied from the power source 4 to the load 3 by the feedback control, based on the difference between the temperature of the load 3 and the predetermined temperature, and to correct the operation value obtained in the feedback control so as to suppress the decrease in temperature of the load 3. Thereby, the operation value is corrected to a value that reflects the temperature of the load 3, which is a control value of the feedback control that is executed by the control unit 8. Therefore, even when a small operation value is obtained in the feedback control, it is possible to effectively suppress the temperature of the load 3 from dropping sharply.

The diverse controls by the control unit may also be implemented as the control unit 8 executes a program.

Example 4A

Figure 30:
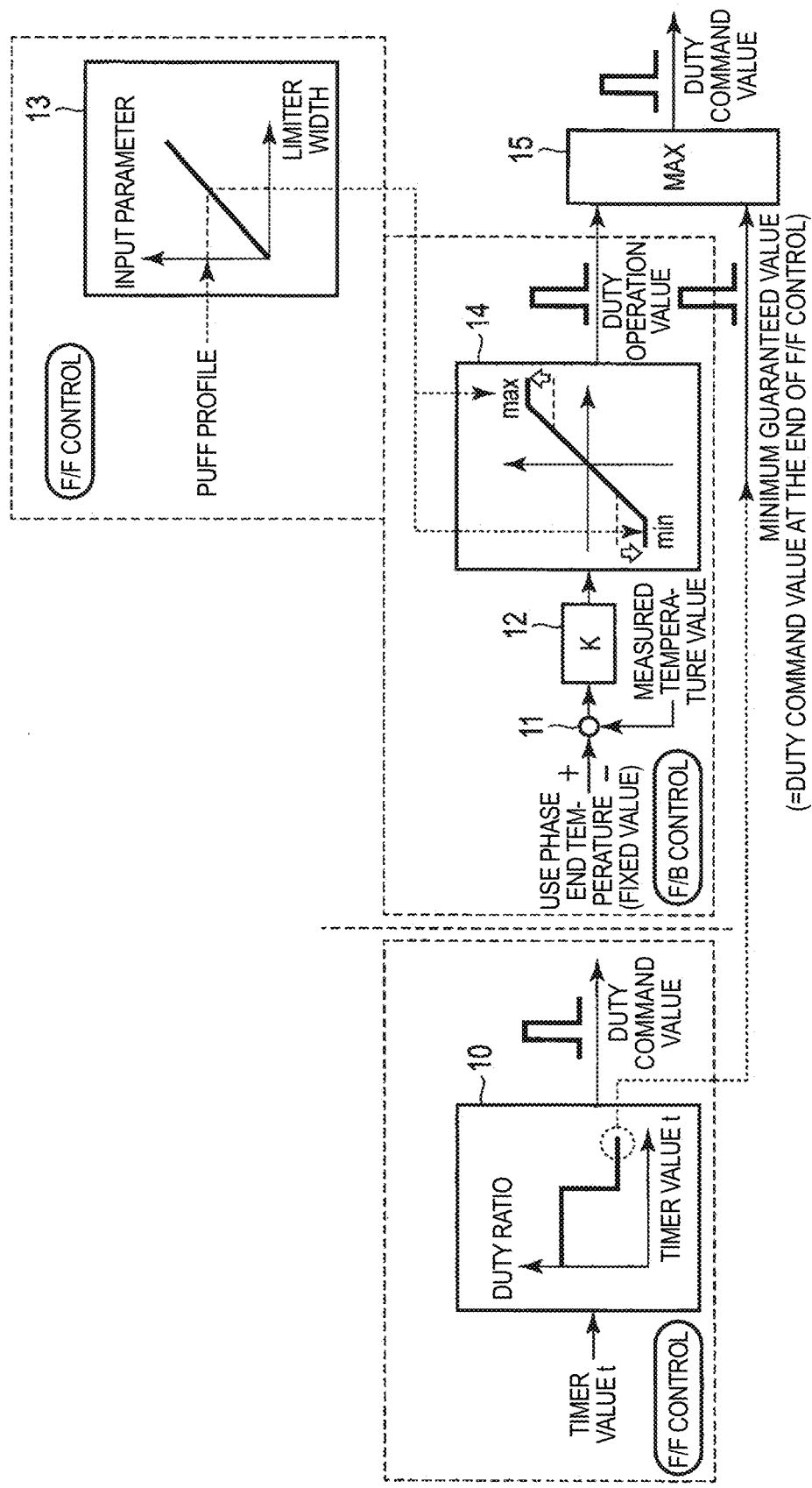
FIG. 30 is a control block diagram depicting an example of control that is executed by the control unit in accordance with Example 4A.

FIG. 30 is a control block diagram depicting an example of control that is executed by the control unit 8 in accordance with Example 4A.

The comparison unit 15 provided in the control unit 8 in accordance with Example 4A compares an operation value obtained as a result of the feedback control and a predetermined value, and outputs a larger value, in the use phase.

The predetermined value is, for example, a minimum guaranteed value of the duty command value indicative of the duty ratio relating to the power that is supplied to the load 3. As the predetermined value, for example, the duty ratio at the end of the preparation phase may be used as the value relating to the power in the preparation phase.

The comparison unit 15 is more specifically described. The comparison unit 15 is input with a duty operation value from the limiter unit 14 and a minimum guaranteed value, in the use phase. The comparison unit 15 compares the duty operation value and the minimum guaranteed value, and obtains a larger value as the duty command value. The control unit 8 controls the power that is supplied to the load 3, based on the duty command value. In the meantime, the duty command value may be applied to the switch 25 provided between the power source 4 and the load 3 or may be applied to the DC/DC converter provided between the power source 4 and the load 3.

Figure 31:
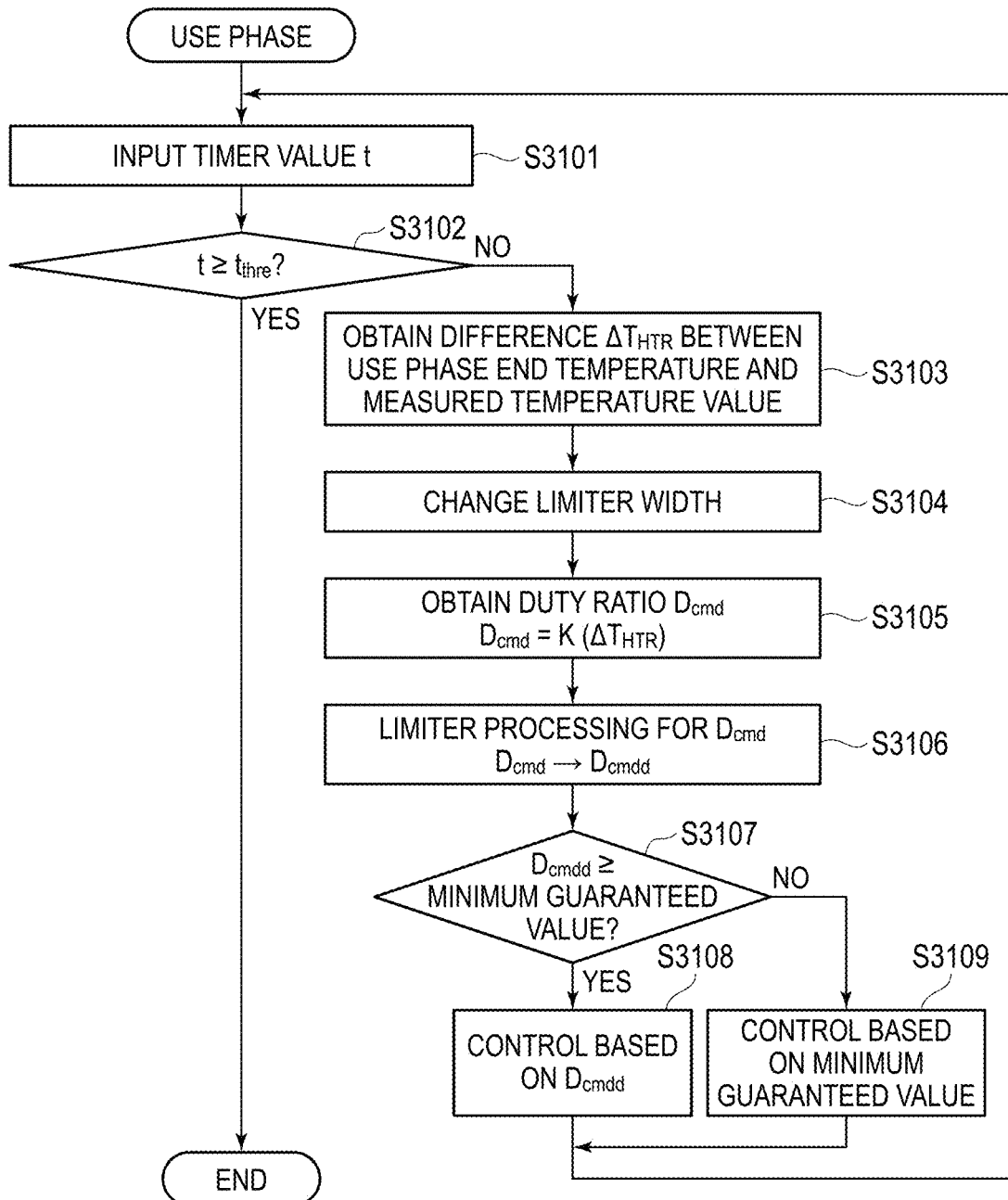
FIG. 31 is a flowchart depicting an example of processing in the use phase by the control unit in accordance with Example 4A.

FIG. 31 is a flowchart depicting an example of processing in the use phase by the control unit 8 in accordance with Example 4A.

The processing from step S3101 to step S3106 is the same as the processing from step S1901 to step S1906 in FIG. 19.

In step S3107, the comparison unit 15 of the control unit 8 determines whether the duty ratio $D_{cmdd}$ indicated by the duty operation value input from the limiter unit 14 is equal to or larger than the minimum guaranteed value.

When it is determined that the duty ratio $D_{cmdd}$ is equal to or larger than the minimum guaranteed value (a determination result in step S3107 is affirmative), the control unit 8 controls the power that is supplied to the load 3, based on the duty command value indicative of the duty ratio $D_{cmdd}$, in step S3108, and then the processing returns to step S3101.

When it is determined that the duty ratio $D_{cmdd}$ is not equal to or larger than the minimum guaranteed value (a determination result in step S3107 is negative), the control unit 8 controls the power that is supplied to the load 3, based on the minimum guaranteed value, in step S3109, and then the processing returns to step S3101.

The operational effects of Example 4A described above are described.

For example, in order to prevent the user from feeling uncomfortable, the aerosol generation device 1 configured to heat the aerosol generation article 9 for aerosol generation controls the power that is supplied to the load 3 so that aerosols generated by the heating do not largely vary. As described above, the control on the power that is supplied to the load 3 is preferably executed in the multiple phases such as the preparation phase and the use phase, for example. As an example, as described in the first embodiment and the second embodiment, the control unit 8 executes the use phase after the preparation phase, so that it is possible to achieve both the early aerosol generation by the aerosol generation device 1 and the stable aerosol generation thereafter.

Also, in the control for shift from one phase to another phase, it is preferably to suppress the temperature of the load 3 from changing sharply upon the phase shift. In particular, when the controls used before and after the shift are more different, the shift time from one phase to another phase becomes a transition period of the control. Therefore, it can be said that the temperature of the load 3, which is a common control amount, is likely to vary through the multiple phases.

In Example 4A, upon the phase shift, the control parameter used in the phase before the shift is used as the minimum guaranteed value. Therefore, as compared to a case where the minimum guaranteed value is not used, it is possible to suppress the temperatures of the load 3 and the aerosol generation article 9 from changing sharply upon the phase shift.

Example 4B

In Example 4B, control of appropriately suppressing overshoot even when the overshoot, i.e., the sharp increase occurs in the temperature of the load 3 is described.

Figure 32:
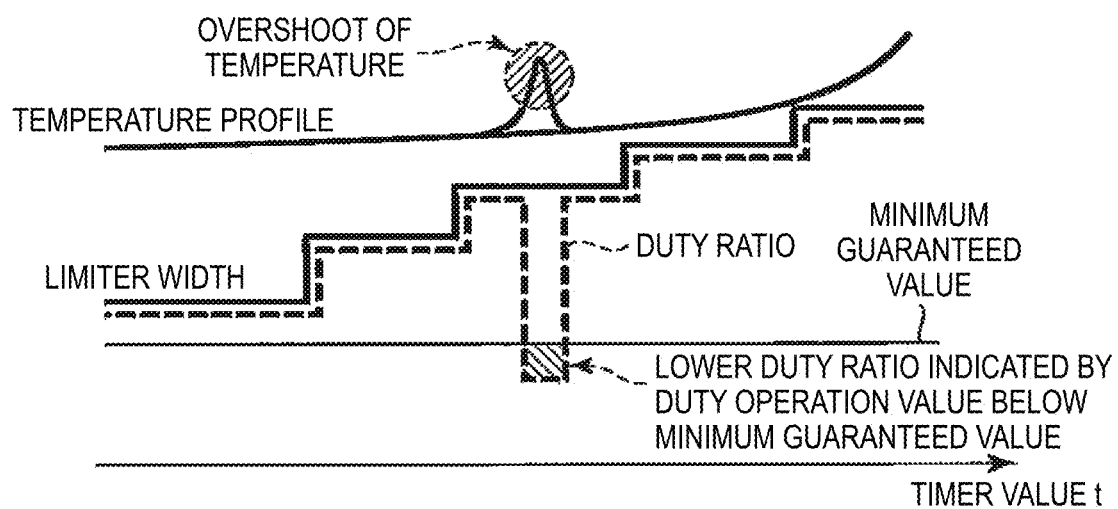
FIG. 32 is a graph depicting an example of a generation state of overshoot in the temperature of the load 3.

FIG. 32 is a graph depicting an example of a generation state of overshoot in the temperature of the load 3. In FIG. 32, it is assumed that the minimum guaranteed value is constant.

The temperature of the load 3 gradually increases as the timer value t, which is an example of an index indicative of a degree of progress of a phase in the use phase, increases, i.e., over time.

The limiter width increases stepwise as the timer value t increases.

The gain unit 12 obtains a duty ratio, based on a difference between the measured temperature value and the use phase end temperature.

The limiter unit 14 obtains a duty ratio within a range of the limiter width, based on the duty ratio obtained by the gain unit 12, and obtains a duty operation value indicative of the duty ratio within the range of the limiter width. Since the limiter width increases stepwise, the duty ratio indicated by the duty operation value may also increase stepwise.

When overshoot occurs in the temperature of the load 3 in the use phase, the control unit 8 decreases the duty command value so as to suppress the overshoot. For example, when the temperature of the load 3 exceeds instantly the use phase end temperature in the feedback control, the control unit 8 lowers the temperature of the load 3 that is a control value by decreasing the duty ratio that is an operation value. However, since the duty ratio indicated by the duty command value does not fall below the minimum guaranteed value, there is a possibility that the temperature of the load 3 will be insufficiently recovered.

Therefore, in Example 4B, the minimum guaranteed value is gradually decreased according to the degree of progress of the use phase, based on the input parameter including at least one of the timer value t, the temperature of the load 3 and the puff profile, so that the temperature of the load 3 can be appropriately recovered even when the overshoot occurs in the temperature of the load 3. The minimum guaranteed value is provided so as to suppress the sharp change in temperatures of the load 3 and the aerosol generation article 9 which may be generated upon shift from the preparation phase to the use phase. That is, when the control unit 8 executes once the use phase, the necessity to provide the minimum guaranteed value is reduced. Therefore, even when the minimum guaranteed value is gradually decreased according to the degree of progress of the use phase, the control unit 8 can control highly the temperatures of the load 3 and the aerosol generation article 9.

Figure 33:
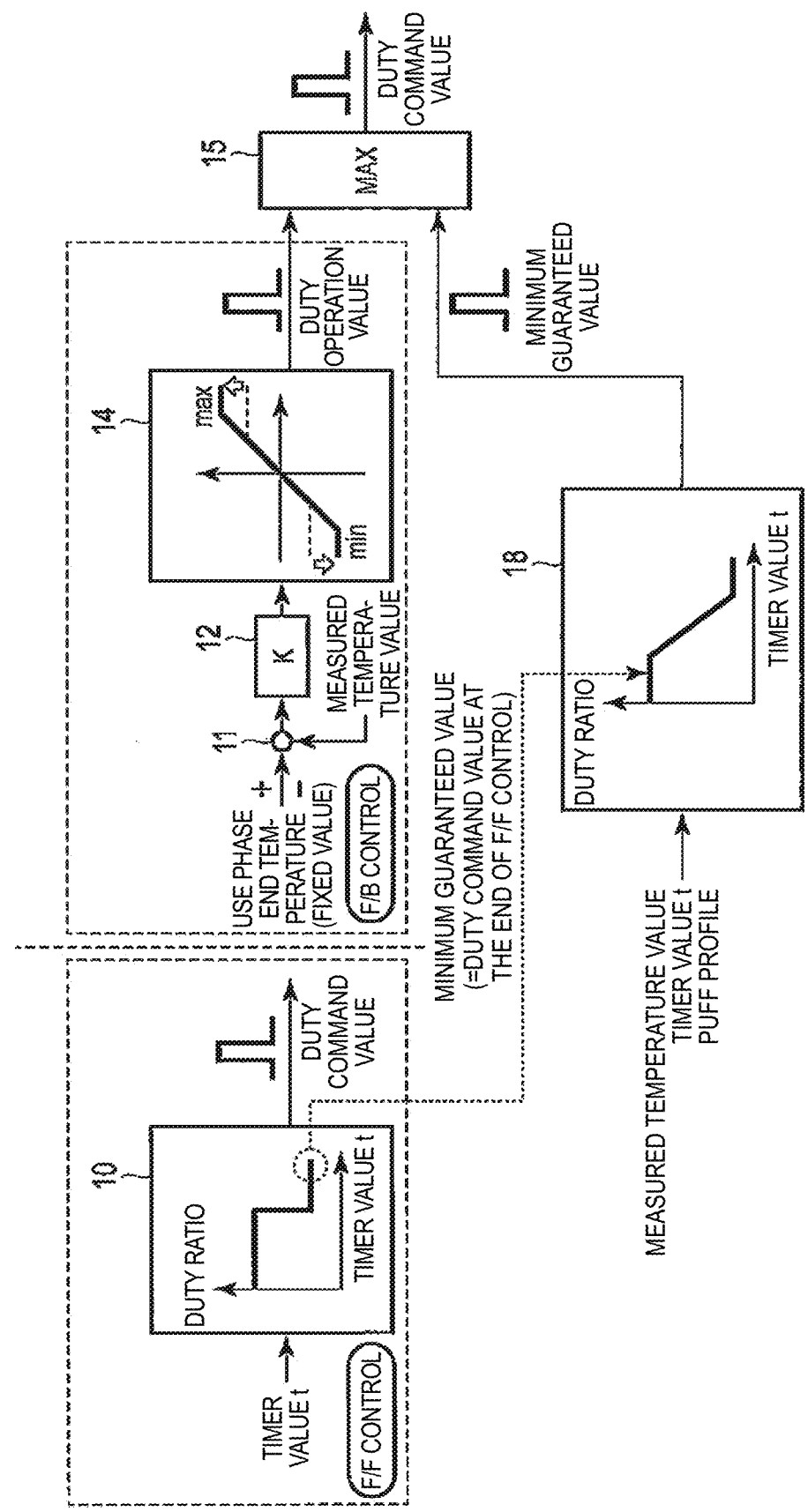
FIG. 33 is a control block diagram depicting an example of control that is executed by the control unit in accordance with Example 4B.

FIG. 33 is a control block diagram depicting an example of control that is executed by the control unit 8 in accordance with Example 4B.

A gradual decrease unit 18 provided in the control unit 8 in accordance with Example 4B decreases gradually the minimum guaranteed value indicative of the duty ratio at the end of the preparation phase, based on the degree of progress of the use phase indicated by the input parameter including at least one of the timer value t, the measured temperature value and the puff profile, for example. In the meantime, ones of the timer value t, the measured temperature value and the puff profile that are used when the gradual decrease unit 18 indicates the degree of progress of the use phase may be the same as or different from ones that are used when the limiter change unit 13 and/or the gain change unit 17 indicates the degree of progress of the use phase.

The comparison unit 15 compares the duty ratio $D_{cmdd}$ limiter-processed by the limiter unit 14 and the minimum guaranteed value decreased gradually by the gradual decrease unit 18, and obtains one indicative of a larger value as a result of the comparison, as the duty command value.

Figure 34:
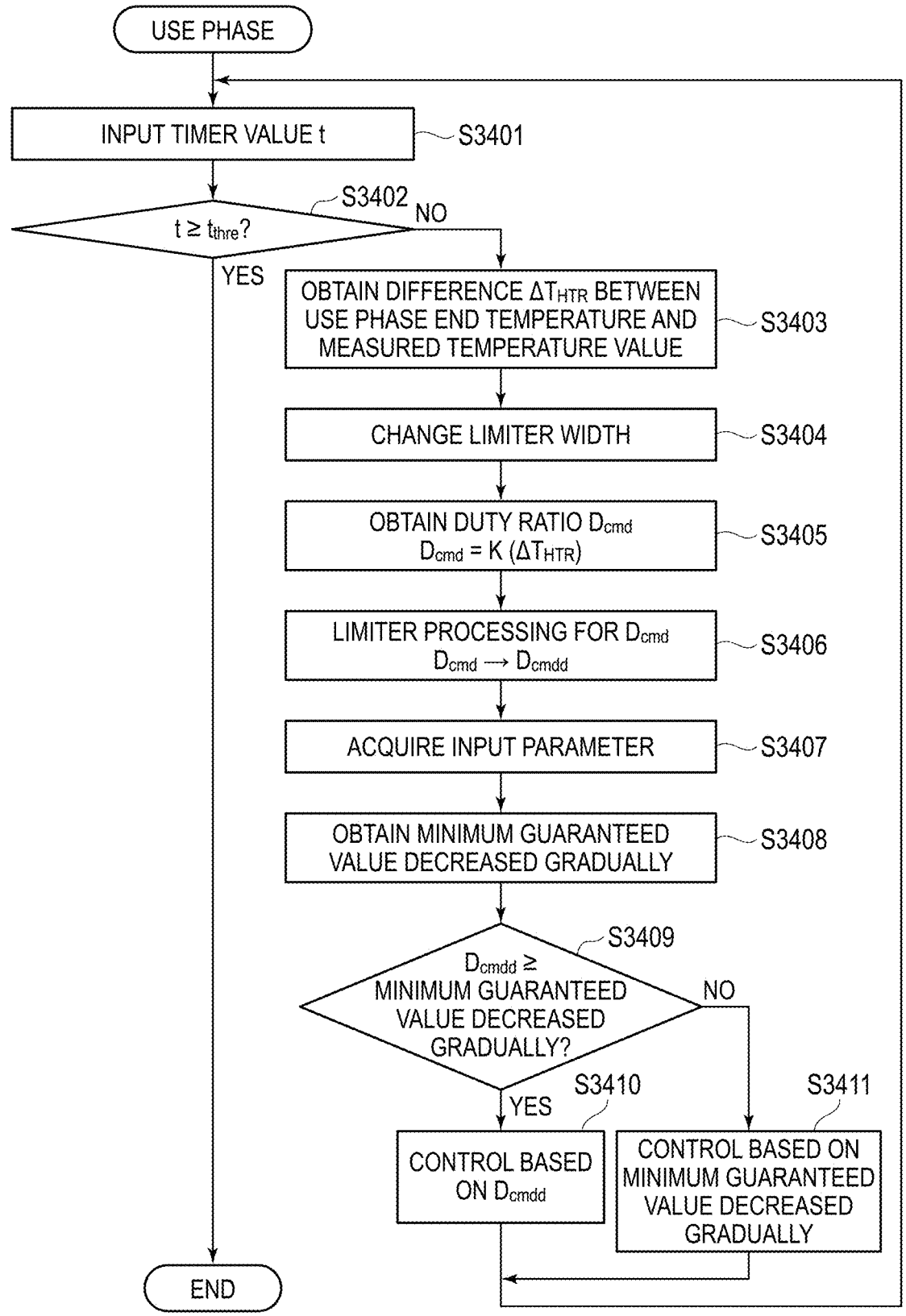
FIG. 34 is a flowchart depicting an example of processing in the use phase by the control unit in accordance with Example 4B.

FIG. 34 is a flowchart depicting an example of processing in the use phase by the control unit 8 in accordance with Example 49.

The processing from step S3401 to step S3406 is the same as the processing from step S1901 to step S1906 in FIG. 19.

In step S3407, the control unit 8 acquires the input parameter.

In step S3408, the gradual decrease unit 18 of the control unit 8 obtains the minimum guaranteed value decreased gradually, based on the input parameter, for example. For example, when the input parameter is the timer value t, it is determined that the larger the timer value t is, the further the use phase progresses, and the minimum guaranteed value is reduced. In the meantime, the gradual decrease unit 18 may decrease gradually the minimum guaranteed value, based on at least one of the measured temperature value and the puff profile, instead of the timer value t or together with the timer value t.

In step S3409, the comparison unit 15 of the control unit 8 determines whether the limiter-processed duty ratio $D_{cmdd}$ is equal to or larger than the minimum guaranteed value decreased gradually.

When it is determined that the duty ratio $D_{cmdd}$ is equal to or larger than the minimum guaranteed value decreased gradually (a determination result in step S3409 is affirmative), the control unit 8 controls the power that is supplied to the load 3, based on the duty command value indicative of the duty ratio $D_{cmdd}$, in step S3410, and then the processing returns to step S3401.

When it is determined that the duty ratio $D_{cmdd}$ is not equal to or larger than the minimum guaranteed value decreased gradually (a determination result in step S3409 is negative), the control unit 8 controls the power that is supplied to the load 3, based on the minimum guaranteed value decreased gradually, in step S3411, and then the processing returns to step S3401.

In Example 4B as described above, the degree of progress of the use phase is determined based on the input parameter including at least one of the timer value t, the temperature of the load 3 and the puff profile, and the minimum guaranteed value is gradually decreased as the degree of progress of the use phase progresses. Thereby, when the overshoot occurs in the load 3, it is possible to sufficiently suppress the power that is supplied to the load 3, so that it is possible to resolve the overshoot promptly and appropriately.

Example 4C

Example 4C is a modified example of Example 4B. In Example 4C, when the use phase progresses, the control is performed so that the duty operation value is used as the duty command value. In other words, in the control of Example 4C, the minimum guaranteed value is invalidated or is made to zero, based on the input parameter or the processing of the comparison unit 15 based on the minimum guaranteed value is cancelled.

Figure 35:
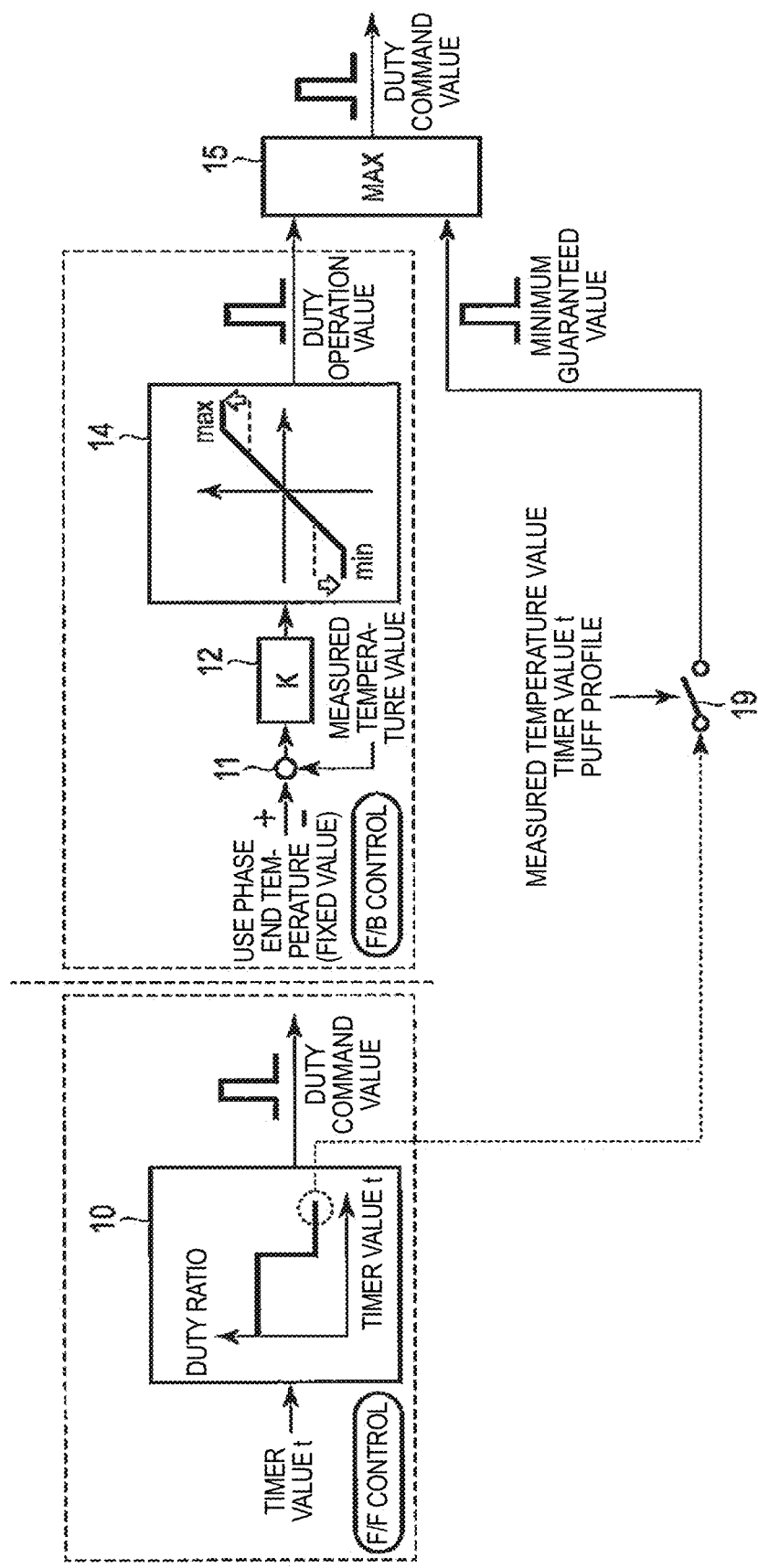
FIG. 35 is a control block diagram depicting an example of control that is executed by the control unit in accordance with Example 4C.

FIG. 35 is a control block diagram depicting an example of control that is executed by the control unit 8 in accordance with Example 4C.

A change unit 19 provided in the control unit 8 in accordance with Example 4C switches the minimum guaranteed value to zero or invalidates the same when the input parameter including at least one of the timer value t, the measured temperature value and the puff profile indicates a predetermined degree of progress, for example.

When the minimum guaranteed value is switched to zero by the change unit 19, the comparison unit 15 sets the duty operation value input from the limiter unit 14, as the duty command value.

The control unit 8 controls the power that is supplied to the load 3, based on the duty command value corresponding to the duty operation value.

Figure 36:
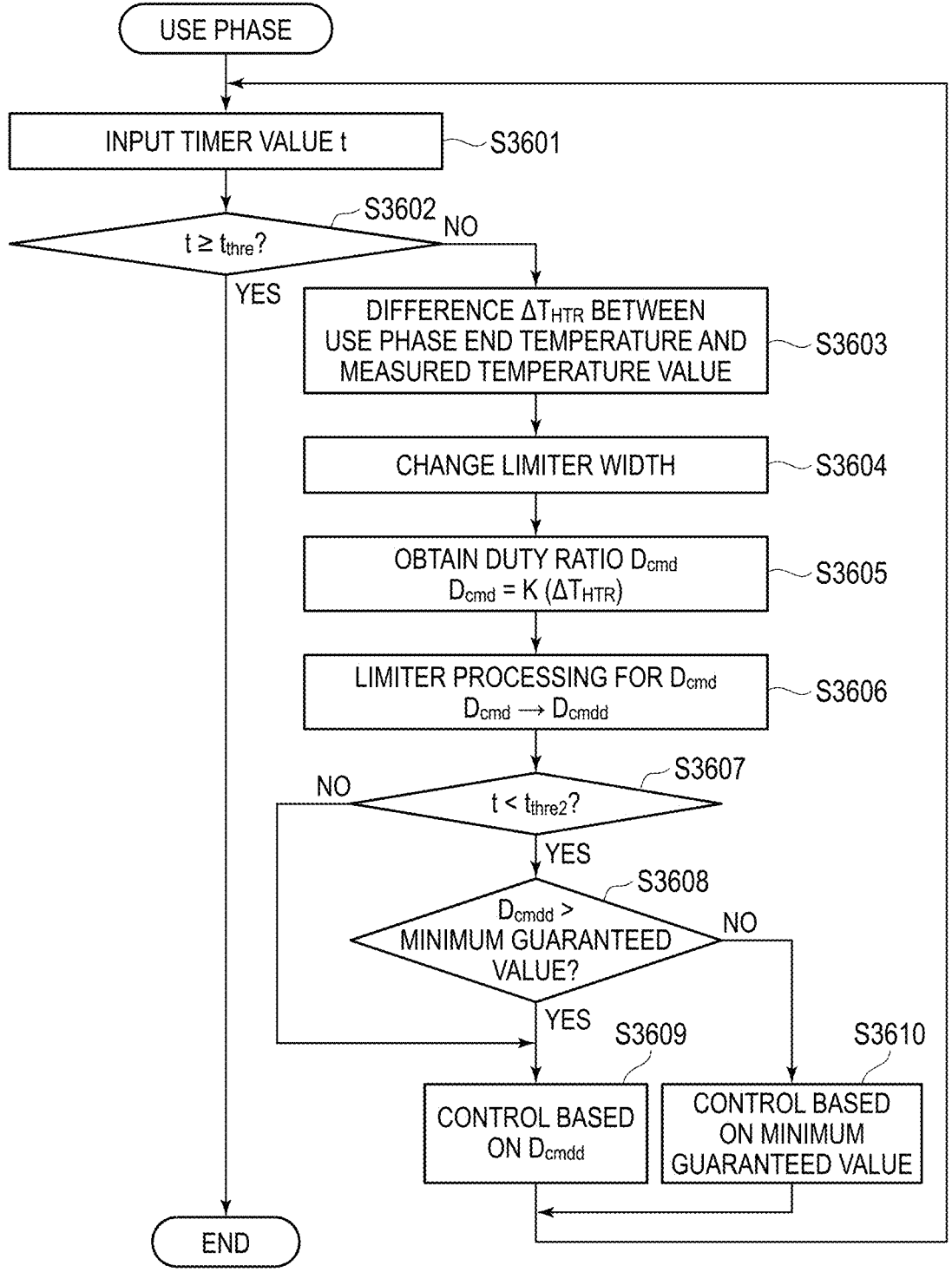
FIG. 36 is a flowchart depicting an example of processing in the use phase by the control unit in accordance with Example 4C.

FIG. 36 is a flowchart depicting an example of processing in the use phase by the control unit 8 in accordance with Example 4C. in FIG. 36, a case where the degree of progress of the use phase is determined using the timer value t as the input parameter is exemplified. However, the degree of progress of the use phase may also be determined using the measured temperature value or the puff profile.

The processing from step S3601 to step S3606 is the same as the processing from step S1901 to step S1906 in FIG. 19.

In step S3607, the change unit 19 of the control unit 8 determines whether the timer value t is less than a predetermined time $t_{thre2}$, for example.

When it is determined that the timer value t is less than a predetermined time $t_{thre2}$ (a determination result in step S3607 is affirmative), the comparison unit 15 of the control unit 8 determines whether the limiter-processed duty ratio $D_{cmdd}$ is equal to or larger than the minimum guaranteed value, in step S3608.

When it is determined by the Change unit 19 that the tinier value t is not less than the predetermined rime $t_{thre2}$ (a determination result in step S3607 is negative), or when it is determined by the comparison unit 15 that the duty ratio $D_{cmdd}$ is equal to or larger than the minimum guaranteed value (a determination result in step S3608 is affirmative), the control unit 8 controls the power that is supplied to the load 3, based on the duty command value indicative of the duty ratio $D_{cmdd}$, in step S3609, and then the processing returns to step S3601.

When it is determined by the comparison unit 15 that the duty ratio $D_{cmdd}$ is not equal to or larger than the minimum guaranteed value (a determination result in step S3608 is negative), the control unit 8 controls the power that is supplied to the load 3, based on the minimum guaranteed value, in step S3610, and then the processing returns to step S3601.

In Example 4C as described above, it is determined whether the progress of the use phase is equal to or greater than the predetermined value, based on the input parameter, and when it is determined that the progress of the use phase is equal to or greater than the predetermined value, the control is switched to the control in which the minimum guaranteed value is not used. Thereby, when a disturbance occurs in the behavior of the temperature of the load 3, such as the overshoot in the temperature, the feedback control functions to output a large operating amount, so that it is possible to highly control the power that is supplied to the load 3. Therefore, it is possible to resolve or converge promptly and appropriately the disturbance in the behavior of the temperature of the load 3.

Example 4D

Example 4D is a modified example of Example 4C. In Example 4D, when e overshoot of the temperature is detected, the control unit 8 invalidates the minimum guaranteed value, sets the minimum guaranteed value to zero or cancels the processing of the comparison unit 15 based on the minimum guaranteed value.

Figure 37:
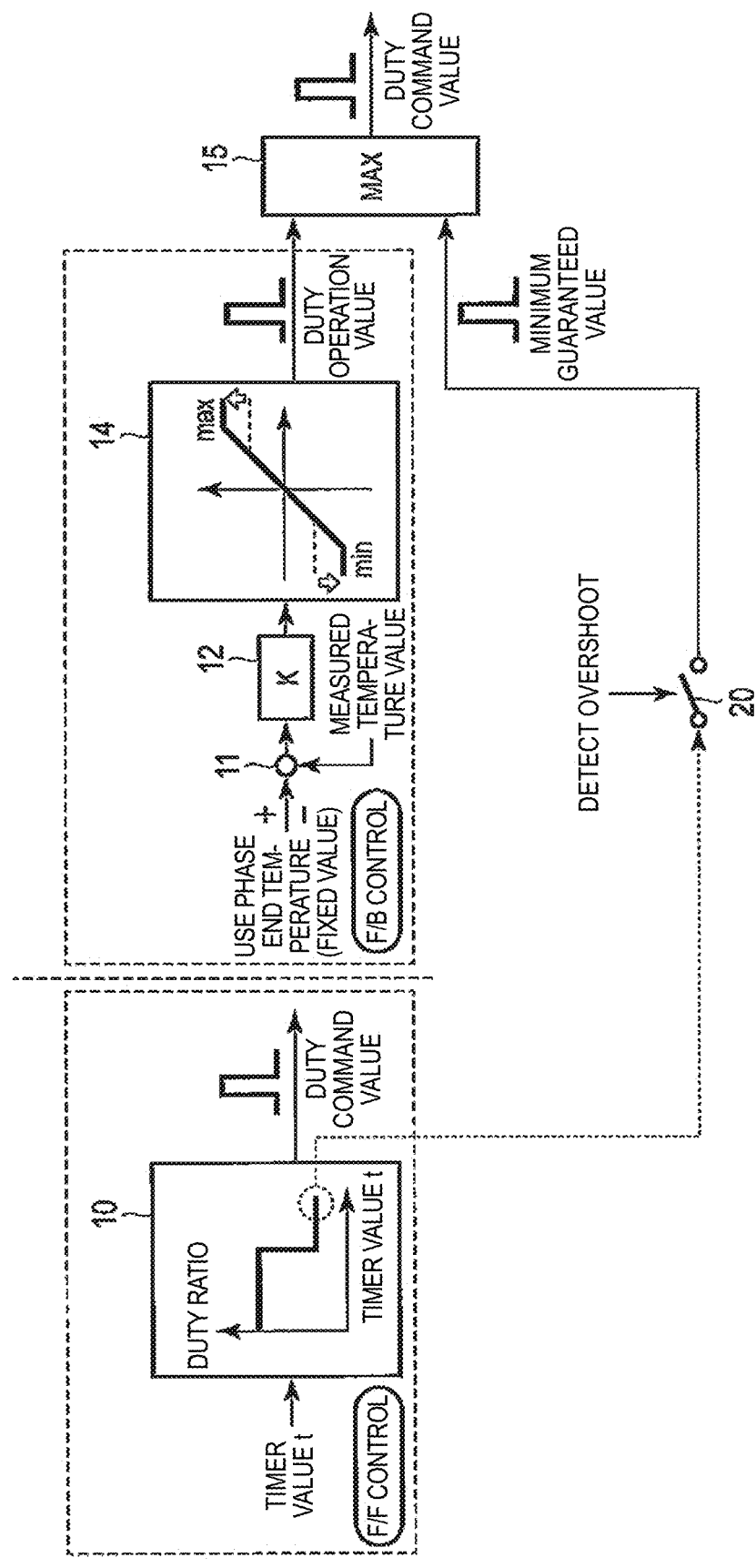
FIG. 37 is a control block diagram depicting an example of control that is executed by the control unit in accordance with Example 4D.

FIG. 37 is a control block diagram depicting an example of control that is executed by the control unit 8 in accordance with Example 4D.

An overshoot detection unit 20 provided in the control unit in accordance with Example 4D invalidates or reduces the minimum guaranteed value when the overshoot of the temperature is detected, for example, and validates or increases again the minimum guaranteed value when the overshoot of the temperature is resolved.

Figure 38:
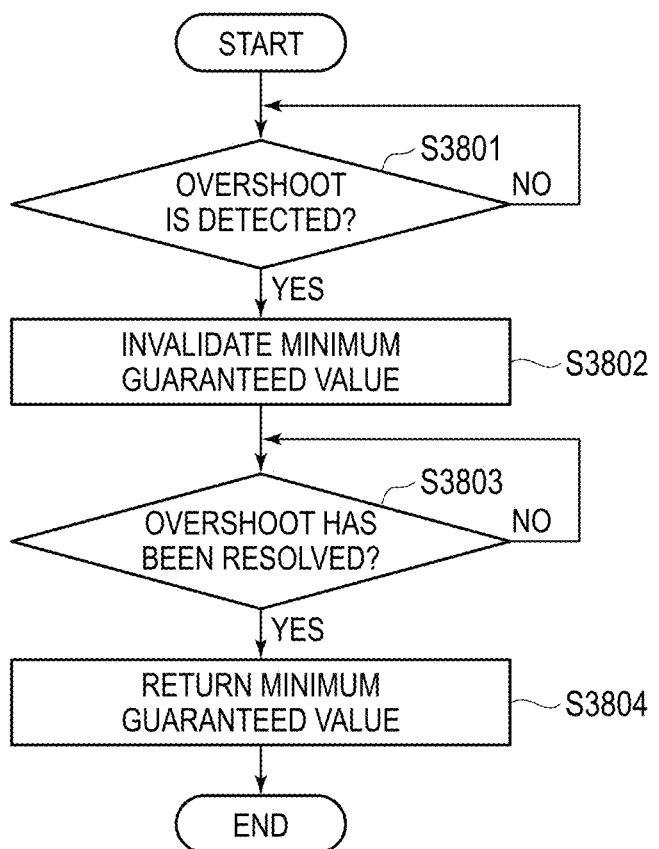
FIG. 38 is a flowchart depicting an example of processing in an overshoot detection unit in accordance with Example 4D.

FIG. 38 is a flowchart depicting an example of processing in the overshoot detection unit 20 in accordance with Example 4D.

In step S3801, the overshoot detection unit 20 executes detection of the overshoot of the temperature, and determines whether the overshoot is detected.

When it is determined that the overshoot is not detected (a determination result in step S3801 is negative), the processing of step S3801 is repeated.

When it is determined that the overshoot is detected (a determination result in step S3801 is affirmative), the overshoot detection unit 20 invalidates or reduces the minimum guaranteed value, in step S3802.

In step S3803, the overshoot detection unit 20 determines whether the overshoot has been resolved.

When it is determined that the overshoot has not been resolved (a determination result in step S3803 is negative), the processing of step S3803 is repeated.

When is determined that the overshoot has been resolved, the overshoot detection unit 20 returns the minimum guaranteed value, in step S3804.

In Example 4D as described above, when the overshoot of the temperature is detected, the minimum guaranteed value is invalidated or reduced, so that it is possible to resolve promptly and appropriately the overshoot of the temperature.

Example 4E

In Example 4E, the control unit 8 obtains a minimum guaranteed value having a duty ratio necessary to keep the temperature of the load 3, based on the input parameter indicative of the degree of progress in the use phase, sets, as the duty command value, a larger value of the duty operation value obtained by the gain unit 12 and the minimum guaranteed value, and controls the power that is supplied to the load 3, based on the duty command value.

In Example 4E, a case where the measured temperature value is used as the input parameter indicative of the degree of progress in the use phase is described as an example. However, the timer value t or the puff profile may also be used as the input parameter.

Figure 39:
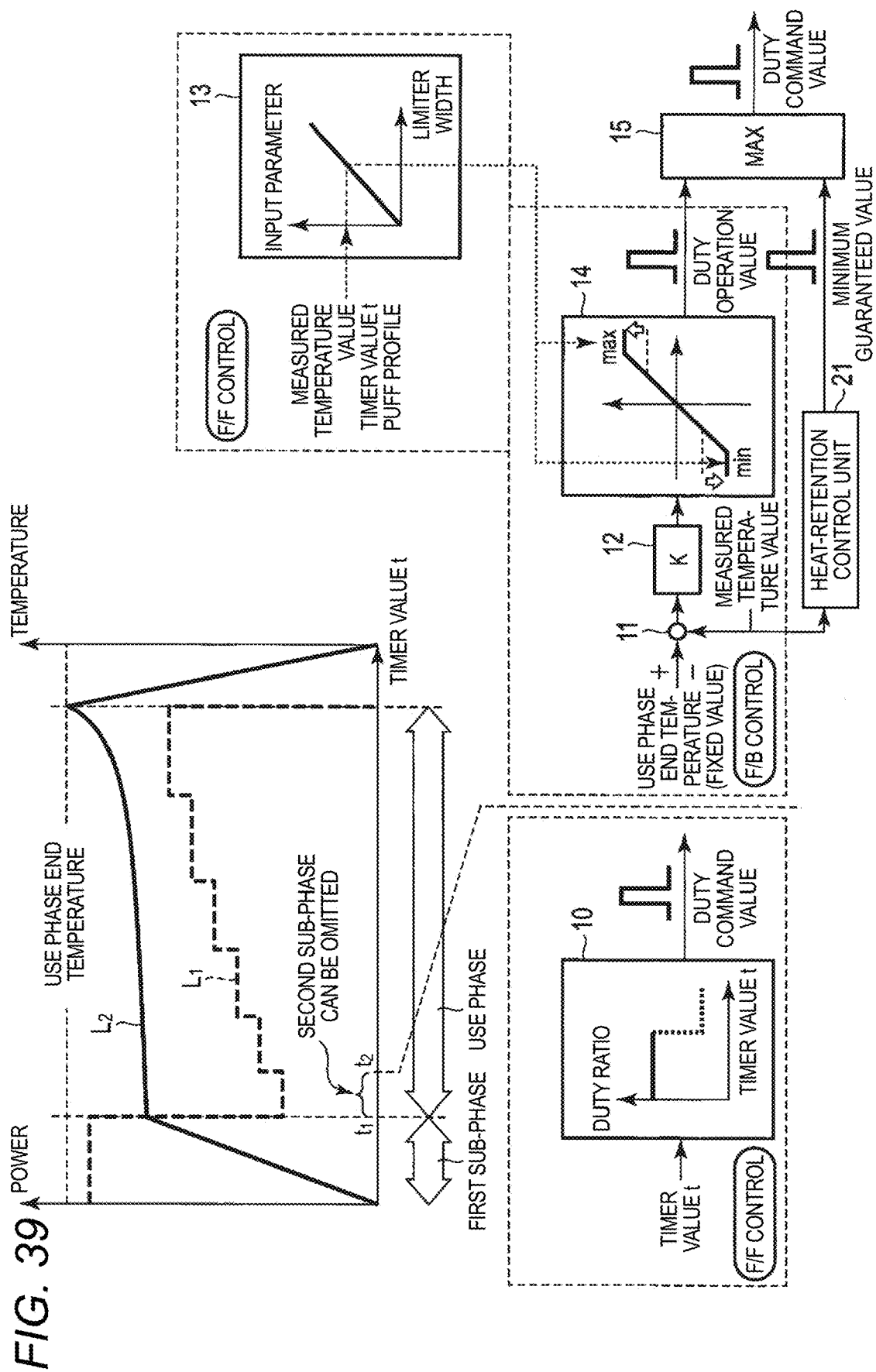
FIG. 39 is a control block diagram depicting an example of control that is executed by the control unit in accordance with Example 4E.

FIG. 39 is a control block diagram depicting an example of control that is executed by the control unit 8 in accordance with Example 4E.

A heat-retention control unit 21 provided in the control unit 8 in accordance with Example 4E obtains a minimum guaranteed value that is a duty ratio necessary to keep the temperature of the load 3, based on the measured temperature value, for example, and outputs the minimum guaranteed value necessary for heat retention to the comparison unit 15. For example, the measured temperature value and the minimum guaranteed value that is a duty ratio necessary for heat retention of the load 3 corresponding to the measured temperature value are analytically or experimentally. Then, the heat-retention control unit 21 may also use a model formula or a table relating to a correlation between the measured temperature value and the minimum guaranteed value derived from the analysis result or experiment result, for example. In the meantime, the heat-retention control unit 21 may also use a correlation between another input parameter such as the timer value t or the puff profile indicative of the degree of progress in the use phase and the minimum guaranteed value.

In this way, the duty ratio necessary to keep the temperature of the load 3 is used as the minimum guaranteed value, so that the second sub-phase included in the preparation phase can be incorporated into the use phase. Thereby, the second sub-phase can be omitted from the preparation phase. Therefore, in Example 4E, the time period of the preparation phase can be shortened, and the decrease in temperature of the load 3 can be suppressed because the temperature of the load 3 is kept according to the minimum guaranteed value.

Figure 40:
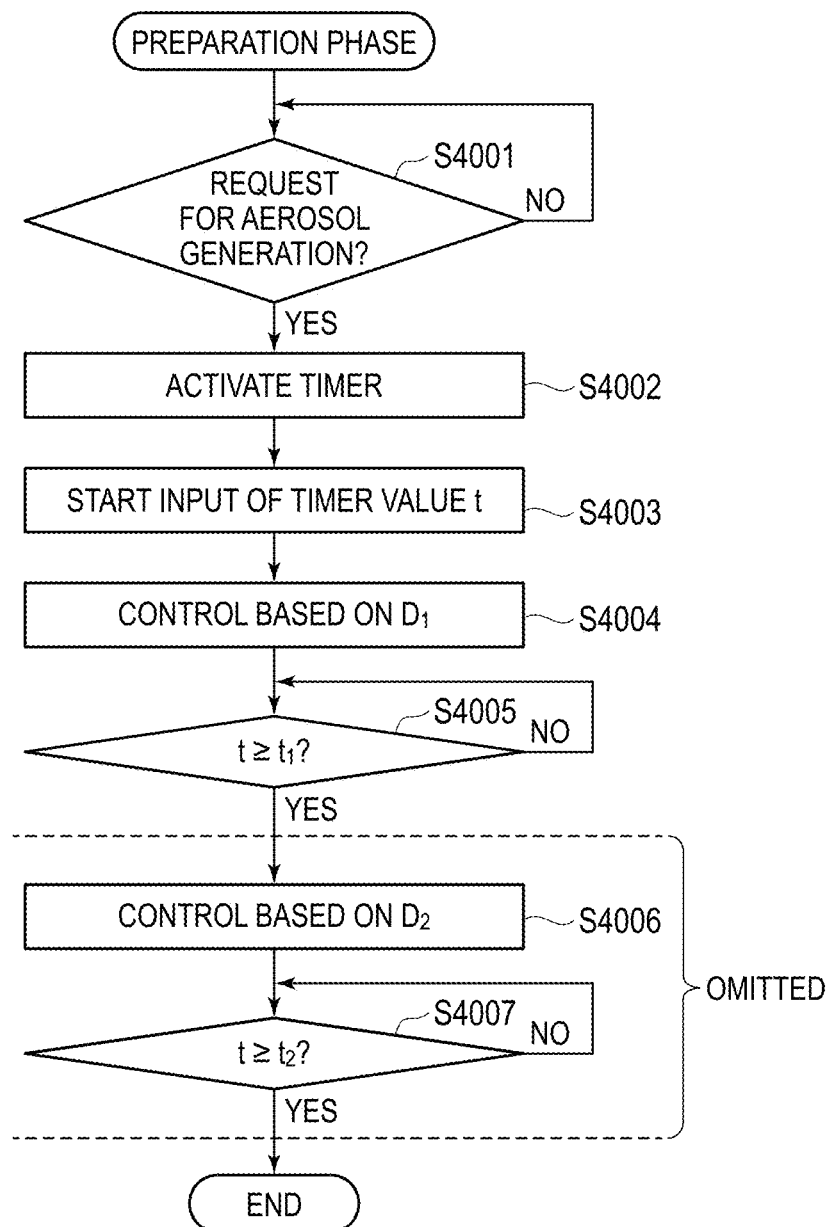
FIG. 40 is a flowchart depicting an example of processing in the preparation phase by the control unit in accordance with Example 4E.

FIG. 40 is a flowchart depicting an example of processing in the preparation phase by the control unit 8 in accordance with Example 4E.

The processing from step S4001 to step S4005 in FIG. 40 is the same as the processing from step S501 to step S505 in FIG. 5.

In the processing of FIG. 40, it should be noted that the processing of step S4006 and step S4007 corresponding to step S506 and step S507 is omitted from the processing of FIG. 5.

Figure 41:
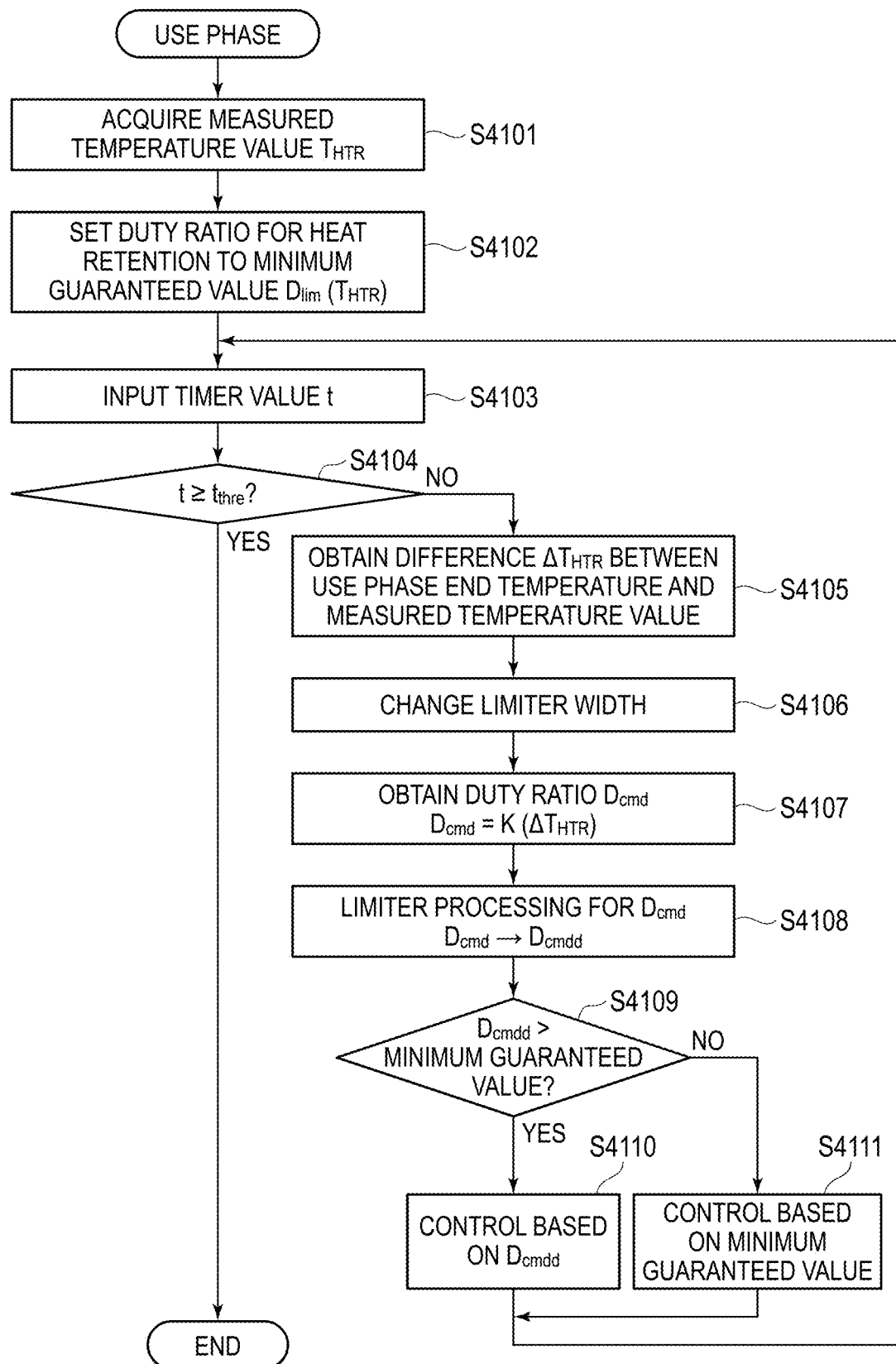
FIG. 41 is a flowchart depicting an example of processing in the use phase by the control unit in accordance with Example 4E.

FIG. 41 is a flowchart depicting an example of processing in the use phase by the control unit 8 in accordance with Example 4E.

In step S4101, the heat-retention control unit 21 of the control unit 8 inputs the measured temperature value $T_{HTR}$ from the temperature measurement unit 6.

In step S4102, the heat-retention control unit 21 obtains the duty ratio necessary to keep the temperature indicated by the measured temperature value $T_{HTR}$, and outputs a minimum guaranteed value $D_{lim}$ ($T_{HTR}$) indicative of the duty ratio necessary for heat retention to the comparison unit 15. As an example, when the heat-retention control unit 21 has the correlation between the input parameter and the minimum guaranteed value, as a model formula, $D_{lim}$ ($T_{HTR}$) is a function. As an example, when the heat-retention control unit 21 has the correlation between the input parameter and the minimum guaranteed value, as a table, $D_{lim}$ ($T_{HTR}$) is a query for the table.

The processing from step S4103 to step S4111 is the same as the processing from step S3101 to step S3109 in FIG. 31. In the meantime, after step 4110 and step S4111, the processing may return to step S4103 or step S4101.

In Example 4E as described above, it is possible to resolve appropriately the change in temperature such as overshoot while securing the heat retention of the load 3. Also, in Example 4E, it is possible to omit the second sub-phase from the preparation phase, thereby shortening the preparation phase.

Fifth Embodiment

In an electronic cigarette or a heating type cigarette, in order not to impair the amount and flavor and taste of aerosols generated from the aerosol generation article 9 even when the temperature of the load 3 is feedback-controlled and the temperature of the load 3 is decreased due to the user's inhalation, it is preferably to promptly recover the decrease in temperature and to compensate for the temperature of the load 3.

However, for example, when the operating amount obtained by the feedback control is small, the sufficient power is not supplied to the load 3 whose temperature has been decreased, so that it may take to recover the decrease in temperature of the load 3.

Therefore, in a fifth embodiment, when the user's inhalation is detected, the operating amount obtained by the feedback control is temporarily increased to promptly recover the decrease in temperature of the load 3 due to the inhalation. More specifically, when the decrease in temperature occurs due to the aerosol inhalation in the use phase, for example, the control unit 8 of the fifth embodiment performs control of expanding the limiter width of the limiter unit 14 used in the feedback control, as compared to the limiter width before the decrease in temperature occurs. Thereby, in the fifth embodiment, the decrease in temperature of the load 3 upon the inhalation is promptly recovered to compensate for the temperature of the load 3. Therefore, even when the user's inhalation is performed, it is possible to suppress the impair in amount and flavor and taste of aerosols generated from the aerosol generation article 9.

When the temperature drop of the load 3 is detected during the execution of the feedback control, the control unit 8 of the fifth embodiment may change the value of the variable that is used in the feedback control so as to increase the power that is supplied from the power source 4 to the load 3. Thereby, as compared to a case where the value of the variable that is used in the feedback control is not changed, it is possible to promptly recover the temperature of the load 3. Herein, the change of the variable that is used in the control includes changing one variable to another variable and changing a value stored in a variable, for example.

When the drop is detected, the control unit 8 may increase at least one of the gain that is used in the feedback control and the upper limit value of the power that is supplied from the power source 4 to the load 3. Thereby, as compared to a case where both the gain and the upper limit value of the power are not increased, the temperature of the load 3 can be promptly recovered.

When the drop is detected, the control unit 8 may increase the target temperature that is used in the feedback control. Thereby, as compared to a case where the target temperature is not increased, the temperature of the load 3 can be promptly recovered.

The control unit 8 may be configured to execute the feedback control so that the temperature of the load 3 gradually increases, and may change the variable to a value that is different from a value before the change, based on the detection of the drop, when the drop is resolved. Thereby, for example, it is possible to supply more power to the load 3 than before the drop is detected. As described in the second embodiment, in order to stabilize the amount of aerosols generated from the aerosol generation article 9, it is necessary to increase the temperature of the load 3 and the temperature of the aerosol generation article 9 heated by the load 3 over time. Therefore, more power than before the drop is detected is supplied to the load 3, so that it is possible to suppress the decrease in the amount of aerosol generation before and after the drop.

The control unit 8 may be configured to execute the feedback control so that the power that is supplied from the power source 4 to the load 3 gradually increases, and may change the variable to a value that is different from a value before the change, based on the detection of the drop, when the drop is resolved. Thereby, for example, it is possible to supply more power to the load 3 than before the drop is detected. As described above, more power than before the drop is detected is supplied to the load 3, so that it is possible to suppress the decrease in the amount of aerosol generation before and after the drop.

The control unit 8 may be configured to gradually increase at least one of the gain that is used in the feedback control and the upper limit value of the power that is supplied from the power source 4 to the load 3 as the feedback control progresses, may increase at least one of the gain and the upper limit value by an increment or larger corresponding to the progress of the feedback control when the drop is detected, and may change at least one of the gain and the upper limit value to a value that is different from a value before the increase based on the detection of the drop, when the drop is resolved. Thereby, for example, it is possible to supply more power to the load 3 than before the drop is detected. Therefore, it is possible to suppress the decrease in the amount of aerosol generation before and after the drop.

The control unit 8 may change at least one of the gain and the upper limit value so as not to decrease when the drop is detected or when the drop is resolved. Thereby, it is possible to suppress the temperature of the load 3 from being stagnant. Therefore, the amount of aerosol generation is difficult to decrease over time.

The control unit 8 may change at least one of the gain and the upper limit value so as to increase when the drop is detected or when the drop is resolved. Thereby, it is possible to suppress the reduction in the amount of aerosol generation.

The control unit 8 may increase at least one of the gain and the upper limit value by an increment corresponding to the progress of the feedback control when the drop is resolved. Thereby, since it is possible to increase the temperature of the load 3 in accordance with the same control before the drop is detected, after the drop is resolved, it is possible to stably generate aerosols without being influenced by the inhalation state. Therefore, the user of the aerosol generation device 1 does not feel uncomfortable with respect to the amount and flavor and taste of aerosols generated from the aerosol generation article 9 over the entire use phase. Therefore, it is possible to improve the quality of the aerosol generation device 1.

When the drop is resolved, the control unit 8 may change at least one of the gain and the upper limit value to a value that is different from a value before the increase based on the detection of the drop so that the higher power than before the drop is detected is supplied from the power source 4 to the load 3. Thereby, it is possible to suppress the amount of aerosol generation from being reduced.

The control unit 8 may be configured to reduce the amount in change of the variable with the progress of the feedback control. Thereby, the feedback control functions to output a large operating amount with the phase progress, so that it is possible to suppress the change in a variable, whose degree of importance is lowered, from affecting the control.

When the feedback control progresses by a predetermined degree of progress or greater and the drop is detected, the control unit 8 may set the amount in change of the variable to zero. Thereby, even if the drop occurs after the phase progresses to some extent, the variable may not be changed. In the meantime, after the phase progresses to some extent, the drop is immediately resolved by the feedback control capable of outputting the large operating amount. Therefore, the amount of aerosol generation is suppressed from being reduced.

The control unit 8 may be configured to reduce an increase amount of at least one of the gain and the upper limit value with the progress of the feedback control. Thereby, the feedback control functions to output a large operating amount with the phase progress, so that when a degree of change importance of at least one of the gain and the upper limit value is lowered, it is possible to suppress the change of at least one of the gain and the upper limit value from affecting the control.

When the feedback control progresses by a predetermined degree of progress or greater and the drop is detected, the control unit 8 may set the amount in change of at least one of the gain and the upper limit value to zero. Thereby, the feedback control normally functions to output a large operating amount with the phase progress, so that when the change of at least one of the gain and the upper limit value is not necessary, the change of at least one of the gain and the upper limit value can be suppressed.

The control unit 8 may be configured to execute the feedback control so that the temperature of the load 3 is constant, and may change the changed variable to a value before the change, based on the detection of the drop, when the drop is resolved. Thereby, it is possible to promptly resolve the drop and to return the control state to the state before the drop is detected.

The control unit 8 may be configured to detect, as the drop, that the temperature of the load 3 is decreased by a first threshold value or larger or that the power that is supplied from the power source 4 to the load 3 is increased by a second threshold value or larger, the first threshold value may be a value by which it is possible to distinguish a decrease in temperature of the load 3 upon inhalation of aerosols from the aerosol generation article 9 and a decrease in temperature of the load 3 upon non-inhalation of aerosols, and the second threshold value may be a value by which it is possible to distinguish an increase in power that is supplied from the power source 4 to the load 3 upon inhalation of aerosols from the aerosol generation article 9 and an increase in power that is supplied from the power source 4 to the load 3 upon non-inhalation of aerosols. Thereby, when the drop is caused due to the inhalation of aerosols, it is possible to promptly suppress the amount of aerosol generation from being reduced.

When the temperature drop of the load 3 is detected during the execution of the feedback control, the control unit 8 may invalidate the upper limit value of the power that is used in the feedback control and supplied from the power source 4 to the load 3. Thereby, it is possible to increase the power that is supplied to the load 3, based on the drop detection, so that it is possible to promptly suppress the amount of aerosol generation from being reduced due to the drop.

The diverse controls by the control unit 8 may also be implemented as the control unit 8 executes a program.

Example 5A

Figure 42:
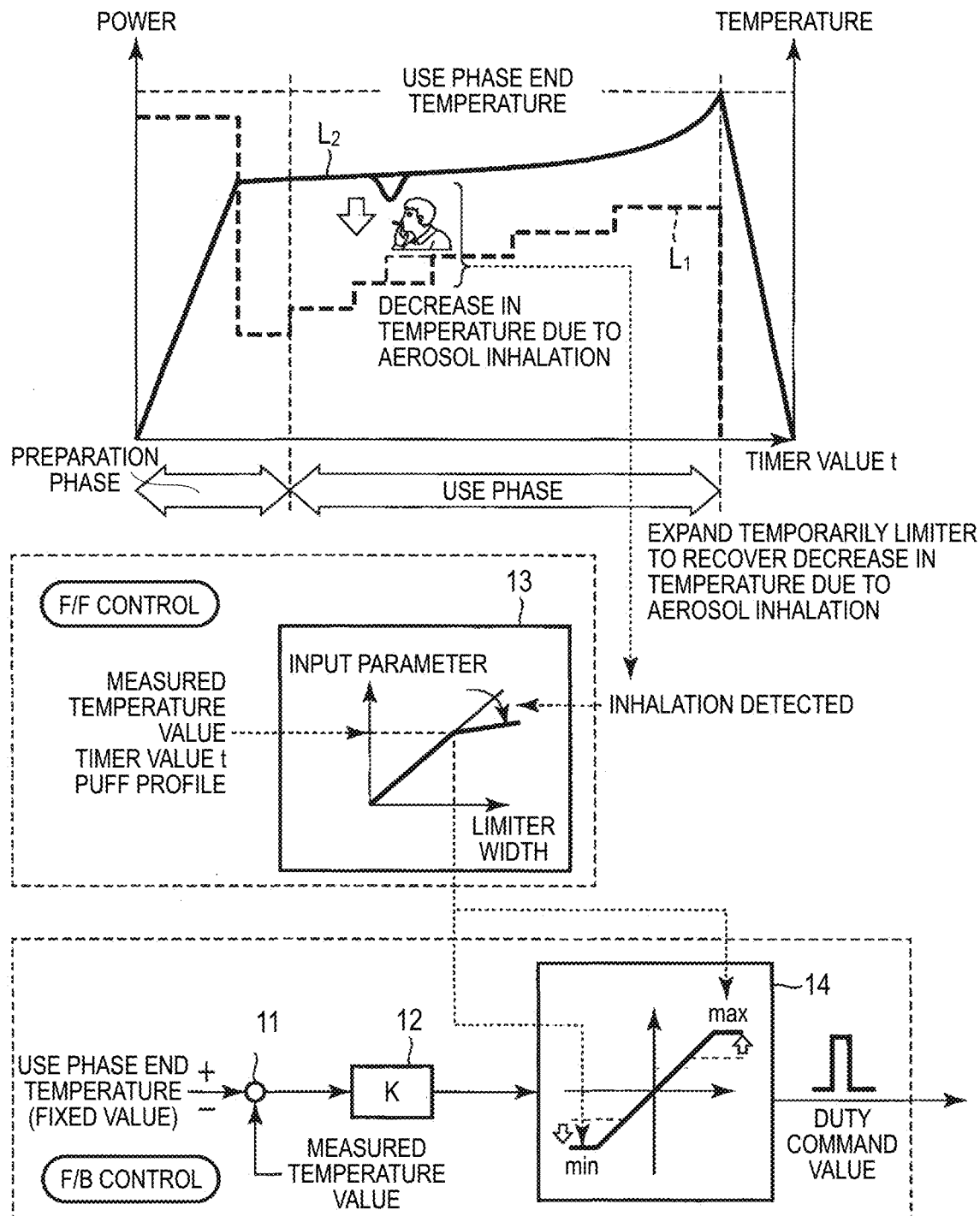
FIG. 42 is a control block diagram depicting an example of control that is executed by the control unit in accordance with Example 5A.

FIG. 42 is a control block diagram depicting an example of control that is executed by the control unit 8 in accordance with Example 5A.

The limiter change unit 13 of the control unit 8 controls the increase width of the limiter width by the feed-forward control, based on the input parameter.

When the user inhales aerosols, an air stream generated in the aerosol generation device 1 passes the vicinity of the load 3, so that the temperature of the load 3 is temporarily decreased. When the aerosol inhalation is detected, the limiter change unit 13 of Example 5A expands temporarily the increase width of the limiter width, thereby recovering promptly the decrease in temperature of the load 3 due to the inhalation.

Figure 43:
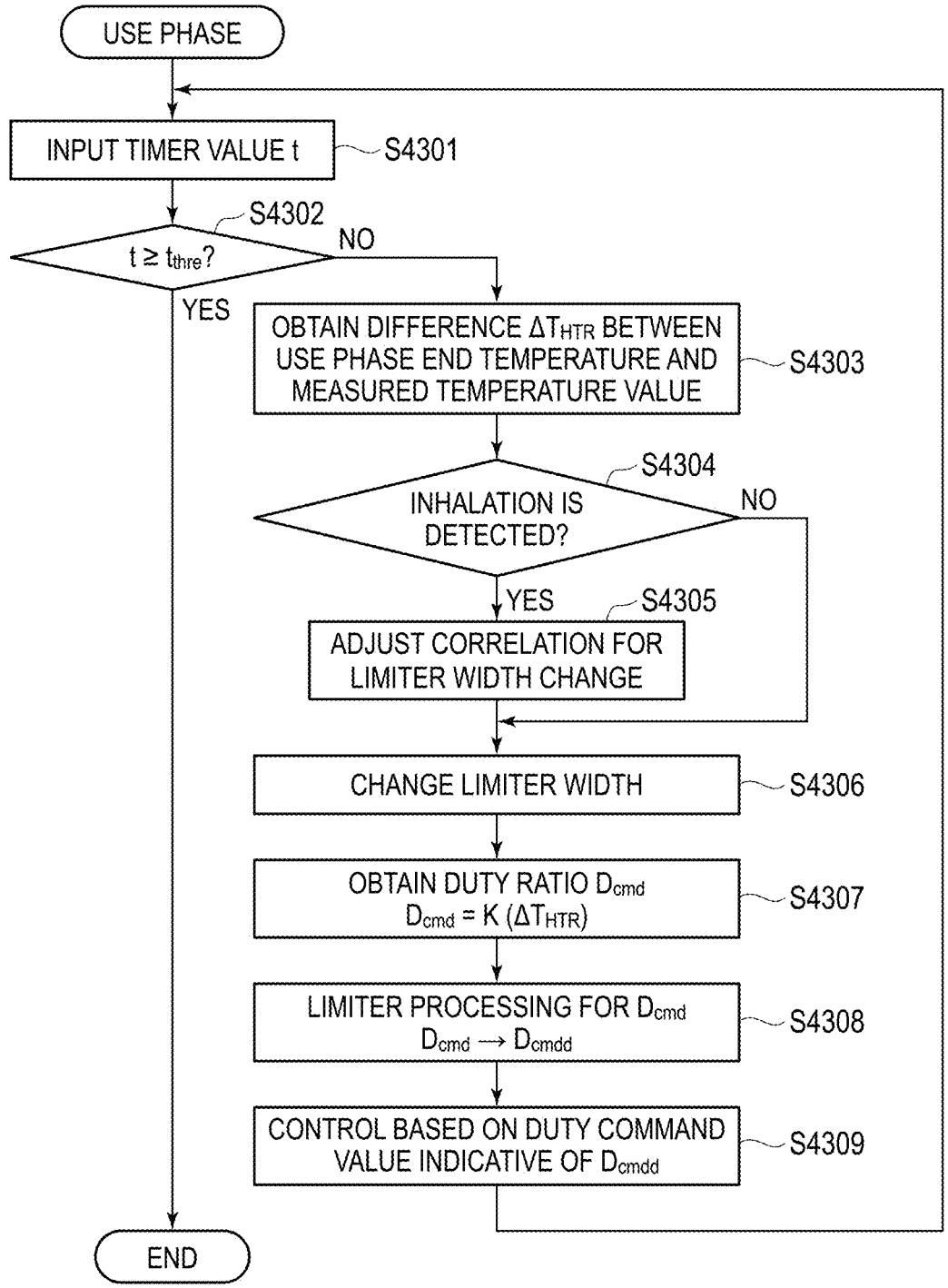
FIG. 43 is a flowchart depicting an example of processing in the use phase by the control unit in accordance with Example 5A.

FIG. 43 is a flowchart depicting an example of processing in the use phase by the control unit 8 in accordance with Example 5A.

The processing from step S4301 to step S4303 is the same as the processing from step S1901 to step S1903 in FIG. 19.

In step S4304, the control unit 8 determines whether the inhalation is detected. The inhalation is detected based on an output value of a sensor configured to detect a physical quantity that varies with the user's inhalation, such as a flow rate sensor, a flow velocity sensor and a pressure sensor provided in the aerosol generation device 1, for example.

When it is determined that the inhalation is not detected (a determination result in step S4304 is negative), the processing proceeds to step S4306.

When it is determined that the inhalation is detected (a determination result in step S4304 is affirmative), the limiter change unit 13 changes a correlation for limiter width change so that the increase width of the limiter width used in the limiter unit 14 is large with respect to an input profile, in step S4305, and proceeds to step S4306.

The processing from step S4306 to step S4309 is the same as the processing from step S1904 to step S1907 in FIG. 19.

In Example 5A as described above, when the inhalation is detected, the increase width of the limiter width that is used in the limiter unit 14 is expanded to increase the duty operation value that is obtained by the feedback control, so that it is possible to promptly recover the decrease in temperature of the load 3 due to the inhalation. Therefore, even when the user performs the inhalation, it is possible to suppress the impair in the amount and flavor and taste of aerosols generated from the aerosol generation article 9.

Example 5B

In Example 5B, control of further increasing the increase width of the limiter width when the inhalation is detected, as compared to the increase width of the limiter width when the inhalation is not detected, is described.

Figure 44:
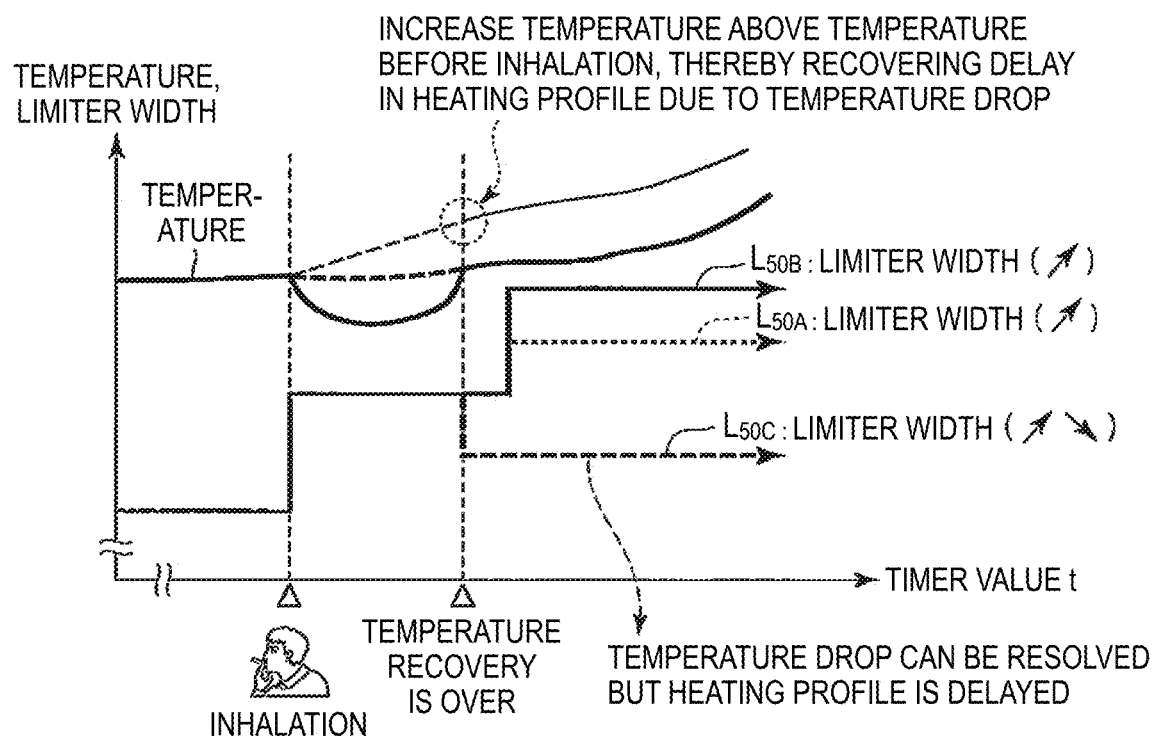
FIG. 44 is a graph depicting an example of changes in the temperature of the load 3 and the limiter width.

FIG. 44 is a graph depicting an example of changes in the temperature of the load 3 and the limiter width. In FIG. 44, the horizontal axis indicates the tinier value t, and the vertical axis indicates the temperature or the limiter width.

The limiter change unit 13 of the control unit 8 controls the increase width of the limiter width so as to increase the temperature of the load 3 after the inhalation is detected more than before the inhalation is detected.

When the inhalation is not detected, the limiter change unit 13 increases the limiter width as the timer value t increases, i.e., over time, as shown with a line $L_{50A}$.

When the inhalation is detected, the limiter change unit 13 changes the limiter width so as to be larger than a change in the line $L_{50A}$, as shown with a line $L_{50B}$, after the temperature of the load 3 is recovered.

In the meantime, as shown with a line $L_{50C}$, the limiter change unit 13 may change the limiter width after the end of the temperature recovery so as to be smaller than the limiter width while the decrease in temperature due to the inhalation is resolved. In this case, the limiter change unit 13 may set the limiter width after the end of the temperature recovery larger than the limiter width before the inhalation detection. Also, the limiter change unit 13 may return the limiter width after the end of the temperature recovery to a state before the inhalation detection.

As an example, when the control unit 8 evaluates the degree of progress of the use phase by the temperature of the load 3, if the decrease in temperature occurs due to the inhalation, the degree of progress of the use phase is stagnant. After the temperature of the load 3 is recovered, when the limiter width is changed as shown with the line $L_{50A}$, the degree of progress of the use phase is delayed, as compared to a case where the inhalation is not detected, because the line $L_{50A}$ indicates the increase width when the inhalation is not detected. Therefore, when the inhalation is detected, the limiter change unit 13 changes the limiter width so as to be larger than the change of the line $L_{50A}$, as shown with the line $L_{50B}$, after the temperature of the load 3 is recovered. Thereby, it is possible to recover the delay in the degree of progress of the use phase due to the inhalation.

In the meantime, the limiter change unit 13 may change the limiter width so as to be larger than the change when the inhalation is not detected, as shown with the line $L_{50B}$, whenever the inhalation is detected. Thereby, even when the user of the aerosol generation device 1 performs the inhalation in any puff profile, the degree of progress of the use phase can be made uniform. Therefore, the flavor and taste of aerosols that are generated from the aerosol generation article 9 can be made stable, irrespective of the puff profile, so that it is possible to improve the quality of the aerosol generation device.

Figure 45:
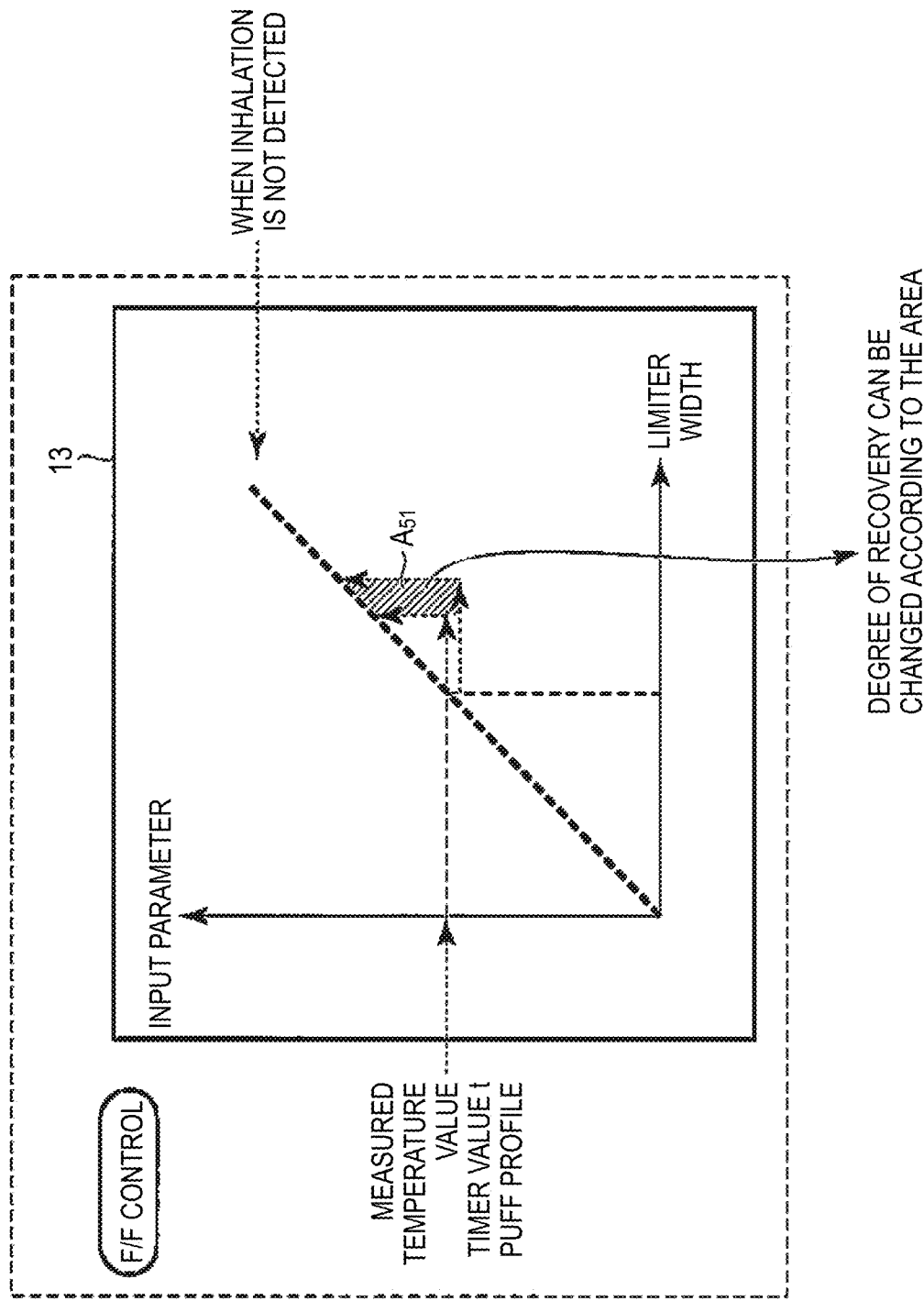
FIG. 45 depicts an example of a limiter change unit in accordance with Example 5B.

FIG. 45 depicts an example of the limiter change unit 13 in accordance with Example 5B.

The limiter change unit 13 in accordance with Example 5B determines the increase width of the limiter width, based on the input parameter including at least one of the timer value t, the measured temperature value and the puff profile.

The limiter change unit 13 expands the limiter width when the inhalation is detected from the decrease in temperature of the load 3 or the puff profile, for example. The larger the increase width of the limiter width (degree of expansion) is, it is possible to further promote the temperature recovery of the load 3. That is, a degree of the temperature recovery of the load 3 is different between a case where the increase width of the limiter width shown in FIG. 45 is expanded to be small and a case where it is expanded to be large, in correspondence to an area $A_{51}$ that is the difference. Therefore, the greater the degree of decrease in temperature of the load 3 is or the greater the necessity to recover the temperature of the load 3 is, an area defined by the increase width of the limiter width shown with the upward sloping broken line when the inhalation is not detected and the expanded increase width shown with the dotted line is preferably larger.

Figure 46:
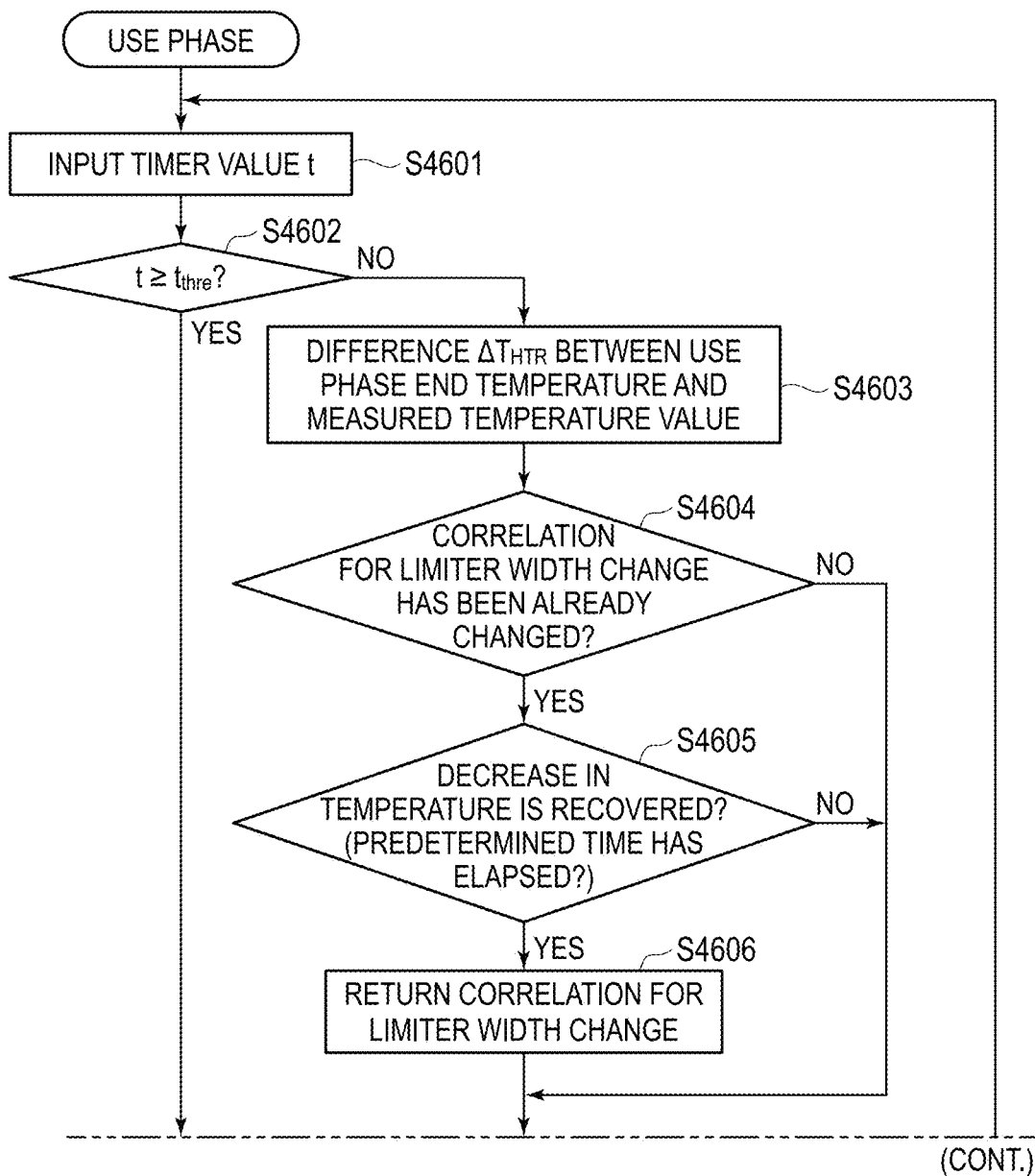
FIG. 46 is a flowchart depicting an example of processing in the use phase by the control unit in accordance with Example 5B.

FIG. 46 is a flowchart depicting an example of processing in the use phase by the control unit 8 in accordance with Example 5B.

The processing from step S4601 to step S4603 is the same as the processing from step S4301 to step S4303 in FIG. 43.

In step S4604, the limiter change unit 13 of the control unit 8 determines whether a third relation of the input parameter and the limiter width (hereinbelow, referred to as correlation for limiter width change) has been already changed, for example. Herein, the correlation for limiter width change may also be expressed by correlation data or correlation function.

When it is determined that the correlation for limiter width change has not been already changed (a determination result in step S4604 is negative), the processing proceeds to step S4607.

When it is determined that the correlation for limiter width change has been already changed (a determination result in step S4604 is affirmative), the limiter change unit 13 determines whether the decrease in temperature of the load 3 has been recovered, for example, whether a predetermined time has elapsed since the decrease in temperature of the load 3, in step S4605.

When it is determined that the decrease in temperature of the load 3 has not been recovered (a determination result in step S4605 is negative), the processing proceeds to step S4607.

When it is determined that the decrease in temperature of the load 3 has been recovered (a determination result in step S4605 is affirmative), the limiter change unit 13 returns the correlation for limiter width change to an original state before the inhalation detection, in step S4606, and the processing proceeds to step S4607.

The processing from step S4607 to step S4612 is the same as the processing from step S4304 to step S4309 in FIG. 43.

In Example 5B as described above, when the inhalation is detected, the limiter width can be expanded, and the temperature of the load 3 can be further increased after the inhalation than before the temperature of the load 3 is decreased due to the inhalation. Thereby, it is possible to recover the delay in heating after the temperature of the load 3 is recovered and to optimize the heating of the load 3.

Also, in Example 5B, after the decrease in temperature is recovered, the correlation for limiter width change is returned to the state before the decrease in temperature, so that it is possible to implement the stable aerosol generation.

Example 5C

In Example 5C, in the use phase, the control unit 8 stably controls the temperature of the load 3 by the feedback control by reducing the influence of the feed-forward control of changing the limiter width when the limiter width is expanded to some extent.

Figure 47:
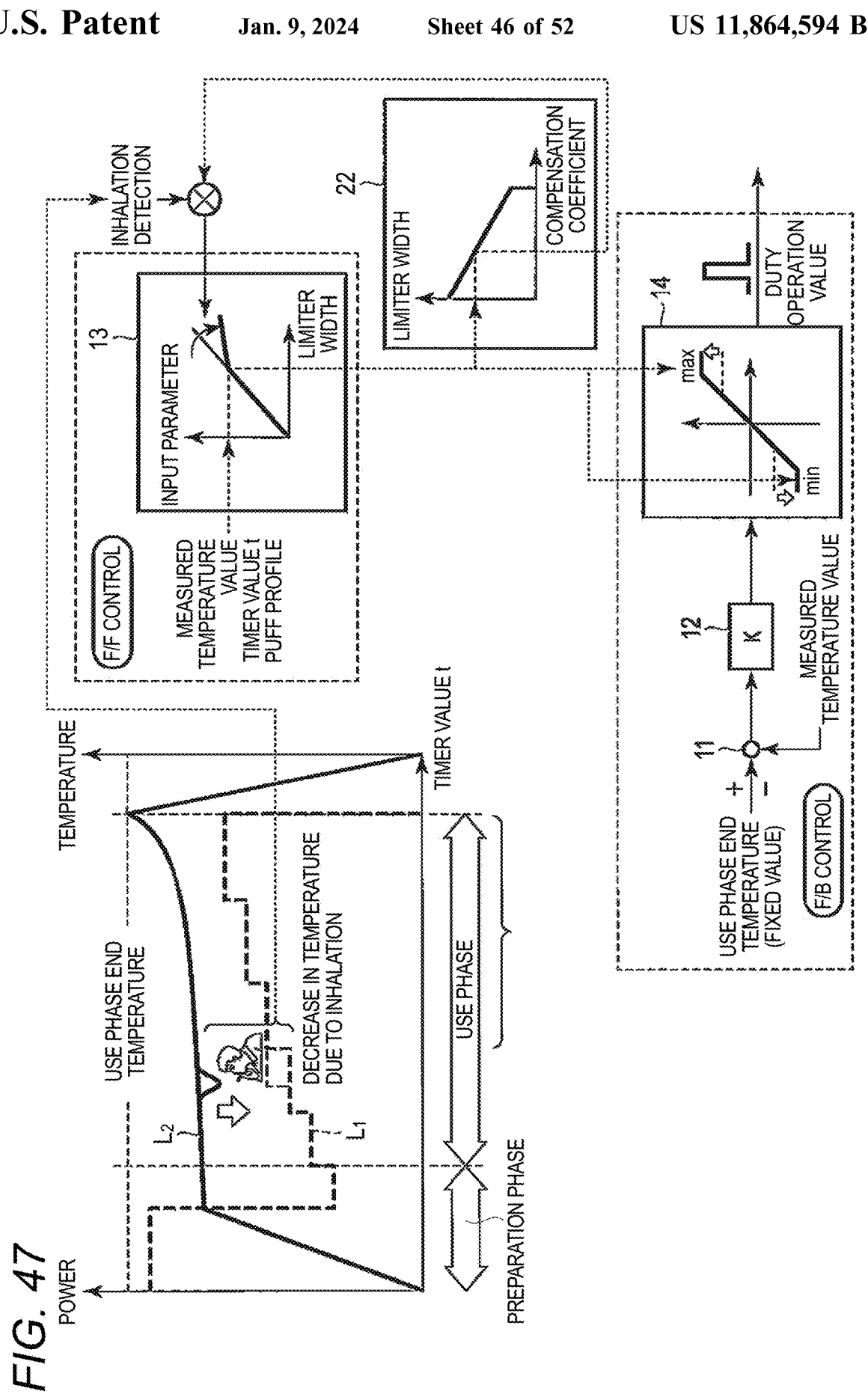
FIG. 47 is a control block diagram depicting an example of control that is executed by the control unit in accordance with Example 5C.

FIG. 47 is a control block diagram depicting an example of control that is executed by the control unit 8 in accordance with Example 5C.

The control unit 8 detects the inhalation from an output value of a sensor configured to detect a physical quantity that varies with the user's inhalation, such as a flow rate sensor, a flow velocity sensor and a pressure sensor provided in the aerosol generation device 1.

In the use phase, the limiter change unit 13 expands gradually the limiter width by the feed-forward control, based on the input parameter. When the inhalation is detected, the limiter change unit 13 expands the increase width of the limiter width for the recovery of the temperature of the load 3.

A limiter width control unit 22 provided in the control unit 8 suppresses the expansion in the limiter width upon the inhalation detection when the limiter width increases to some extent.

More specifically, the limiter width control unit 2 has a fourth relation (hereinbelow, referred to as a compensation relation) where a limiter width and a compensation coefficient corresponding to the limiter width are associated with each other, for example. The compensation coefficient indicates a degree of expanding the limiter width to recover the temperature upon the inhalation detection. In the compensation relation, for example, the limiter width and the compensation coefficient have an inverse correlation. That is, in the compensation relation, for example, the smaller the limiter width is, the greater the compensation coefficient is, and the greater the limiter width is, the smaller the compensation coefficient is. The smaller the compensation coefficient is, the increase width of the limiter width that is changed upon the inhalation detection is further suppressed. As a result, the greater the compensation coefficient is, the limiter width is further sensitively expanded with respect to the inhalation detection, and the smaller the compensation coefficient is, the limiter width expansion is further limited with respect to the inhalation detection.

As an example, as shown in FIG. 47, in the fourth relation, when the limiter width increases to a threshold value or greater, the corresponding compensation coefficient may be zero. As an example, as shown in FIG. 47, in the fourth relation, the compensation coefficient may have an upper limit.

In Example 5C, as the limiter width is expanded, the effect of the recovery from the decrease in temperature by the expansion in the limiter width upon the inhalation detection is reduced, and the effect of the recovery from the decrease in temperature by the feedback control upon the inhalation detection increases. More specifically, when the limiter width is expanded, a possibility that the duty ratio output from the gain unit 12 will be the duty operation value increases. As an example, the duty ratio that is output from the gain unit 12 depends on the difference between the use phase end temperature and the measured temperature value. Therefore, when there is no influence of the limiter unit 14, the decrease in temperature is effectively resolved by the feedback control. Thereby, it is possible to stably perform the control.

Figure 48:
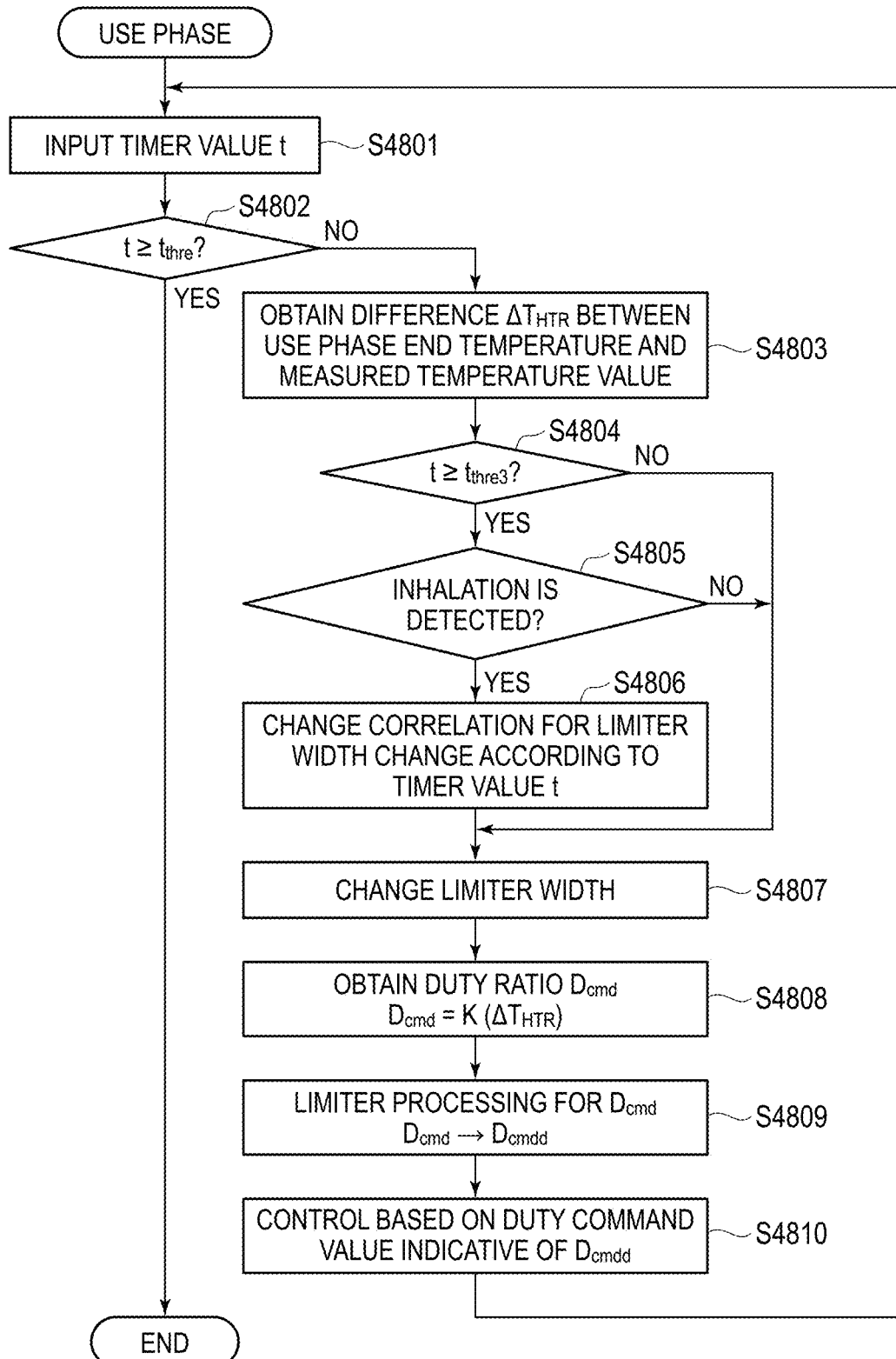
FIG. 48 is a flowchart depicting an example of processing in the use phase by the control unit in accordance with Example 5C.

FIG. 48 is a flowchart depicting an example of processing in the use phase by the control unit 8 in accordance with Example 5C In FIG. 48, it is determined whether to change the limiter width upon the inhalation detection, based on whether the timer value t is smaller than a threshold value $t_{thre3}$. However, it may also be determined whether to change the limiter width upon the inhalation detection, based on at least one of the measured temperature value and the puff profile, instead of the timer value t or together with the timer value t.

The processing from step S4801 to step S4803 is the same as the processing from step S4301 to step S4303 in FIG. 43.

In step S4804, the limiter width control unit 22 determines whether the timer value t is smaller than a threshold value $t_{thre3}$ indicative of a progressed state of the use phase.

When it is determined that the timer value t is not smaller than the threshold value $t_{thre3}$ (a determination result in step S4804 is negative), the limiter width control unit 22 does not change the correlation for limiter width change, and the processing proceeds to step S4807.

When it determined that the timer value t is smaller than the threshold value $t_{thre3}$, the limiter change unit 13 determines whether inhalation is detected. In step S4805.

When it determined that inhalation is not detected (a determination result in step S4805 is negative), the processing proceeds to step S4807.

When it determined that inhalation is detected, the limiter change unit 13 changes the correlation for limiter width change that is used in the limiter change unit 13, based on the timer value t, in step S4806, and the processing proceeds to step S4807.

The processing from step S4807 to step S4810 is the same as the processing from step S4306 to step S4309 in FIG. 43.

The operational effects of Example 5C described above are described.

When the use phase progresses, the limiter width is expanded and the limitation on the magnitude of the duty operation value obtained by the limiter unit 14 is relaxed. In this way, when the limiter width that is used in the limiter unit 14 is sufficiently expanded, the feedback control is likely to effectively function, so that it is possible to recover the decrease in temperature of the load 3 upon the inhalation by the feedback control even though the limiter width is not expanded with the inhalation. In this case, when the limiter width is expanded, the control that is executed in the use phase may be rather complicated.

In Example 5C, in order to recover the decrease in temperature of the load 3 that occurs upon the inhalation, the degree of expanding the limiter width with the inhalation is gradually reduced, so that it is possible to secure the stability of the temperature of the load 3 by using the feedback control with a large operating amount that can be output.

Example 5D

In Example 5D, control of recovering the decrease in temperature of the load 3 upon the inhalation detection by changing the gain of the gain unit 12 is described. Herein, the change of a gain includes changing a gain function, changing a value included in the gain function, and the like, for example.

Figure 49:
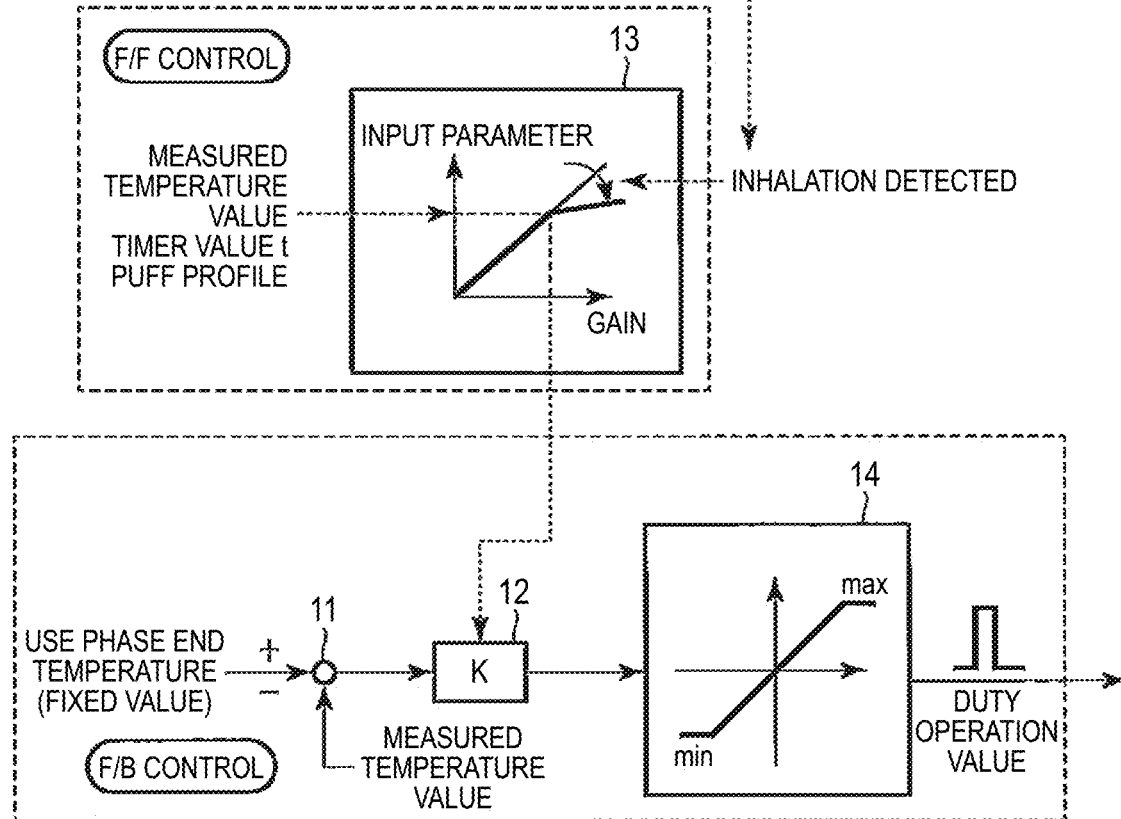
FIG. 49 is a control block diagram depicting an example of control that is executed by the control unit in accordance with Example 5D.

FIG. 49 is a control block diagram depicting an example of control that is executed by the control unit 8 in accordance with Example 5D.

The gain change unit 17 provided in the control unit 8 in accordance with Example 5D changes a gain that is used in the gain unit 12, when the inhalation is detected, for example. More specifically, when the inhalation is detected, the gain change unit 17 changes the gain of the gain unit 12, more specifically, increases the gain of the gain unit 12 so as to obtain a larger duty ratio than when the inhalation is not detected, based on a difference input from the differential unit 11.

Thereby, it is possible to recover the decrease in temperature of the load 3 upon the inhalation.

Figure 50:
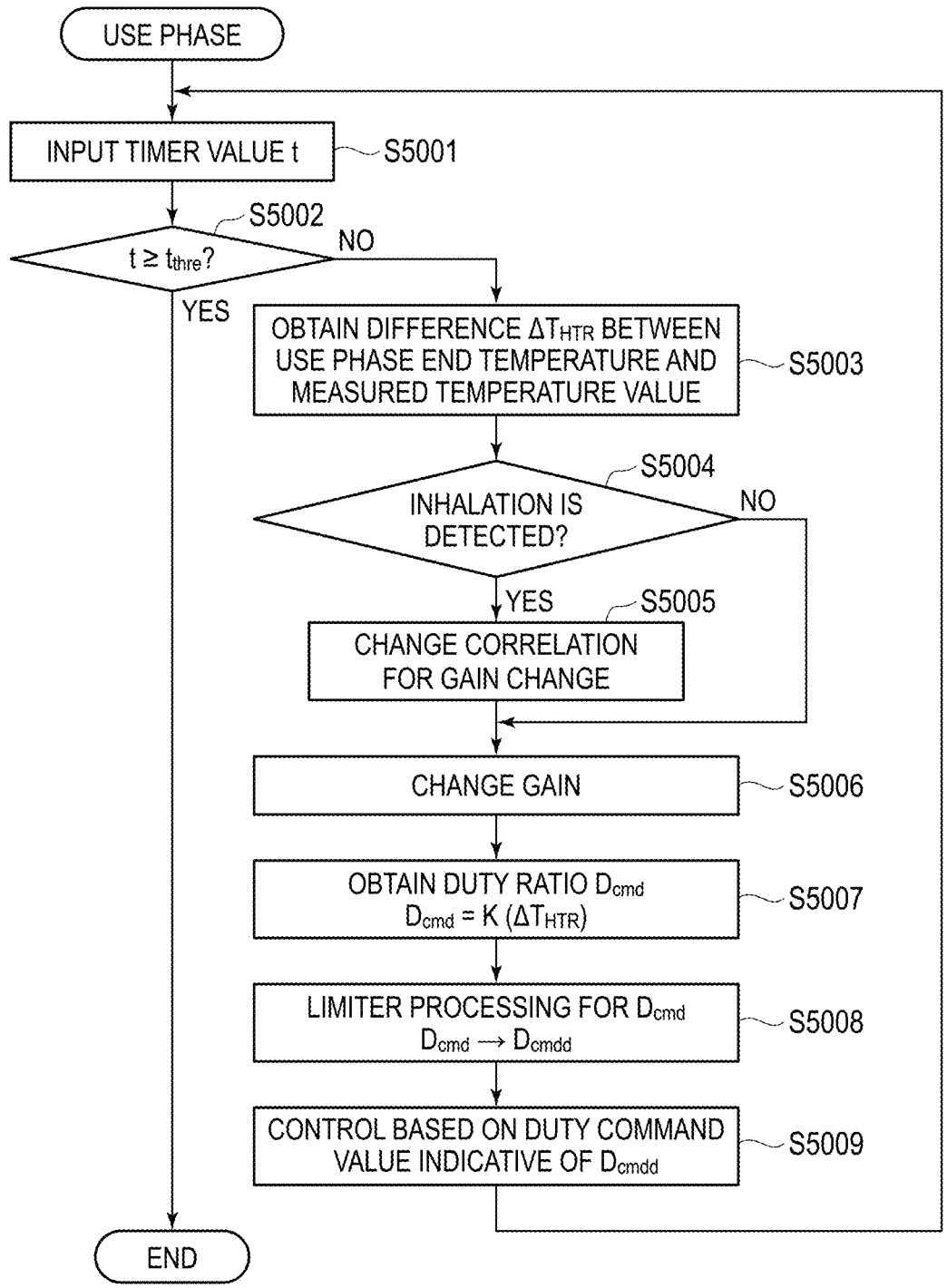
FIG. 50 is a flowchart depicting an example of processing in the use phase by the control unit in accordance with Example 5D.

FIG. 50 is a flowchart depicting an example of processing in the use phase by the control unit 8 in accordance with Example 5D.

The processing from step S5001 to step S5004 is the same as the processing from step S4301 to step S4304 in FIG. 43.

When it is determined in step S5004 that the inhalation is not detected (a determination result is negative), the processing proceeds to step S5006.

When it is determined in step S5004 that the inhalation is detected (a determination result is affirmative), the gain change unit 17 changes a correlation for gain change, which indicates a correlation between a gain and an input parameter, in step S5005, and the processing proceeds to step S5006.

In step S5006, the gain change unit 17 changes the gain of the gain unit 12, based on the input parameter.

The processing from step S5007 to step S5009 is the same as the processing from step S4307 to step S4309 in FIG. 43.

In Example 5D as described above, when the inhalation occurs, the gain of the gain unit 12 is changed to early recover the decrease in temperature of the load 3.

In the meantime, when the inhalation is detected, the control unit 8 may change the use phase end temperature so as to increase the duty operation value that is obtained by the feedback control, instead of the increase width of the limiter width that is used in the limiter unit 14 or the gain of the gain unit 12 or together with the increase width of the limiter width or the gain. When the use phase end temperature is increased, the difference that is output from the differential unit 11 increases, so that the duty ratio output by the gain unit 12 increases. As a result, the duty operation value that is output by the feedback control can be increased.

Example 5E

In Example 5E, control of expanding the limiter width upon the inhalation detection and returning the limiter width to a value before the inhalation detection after the decrease in temperature of the load 3 due to the inhalation is recovered is described.

Figure 51:
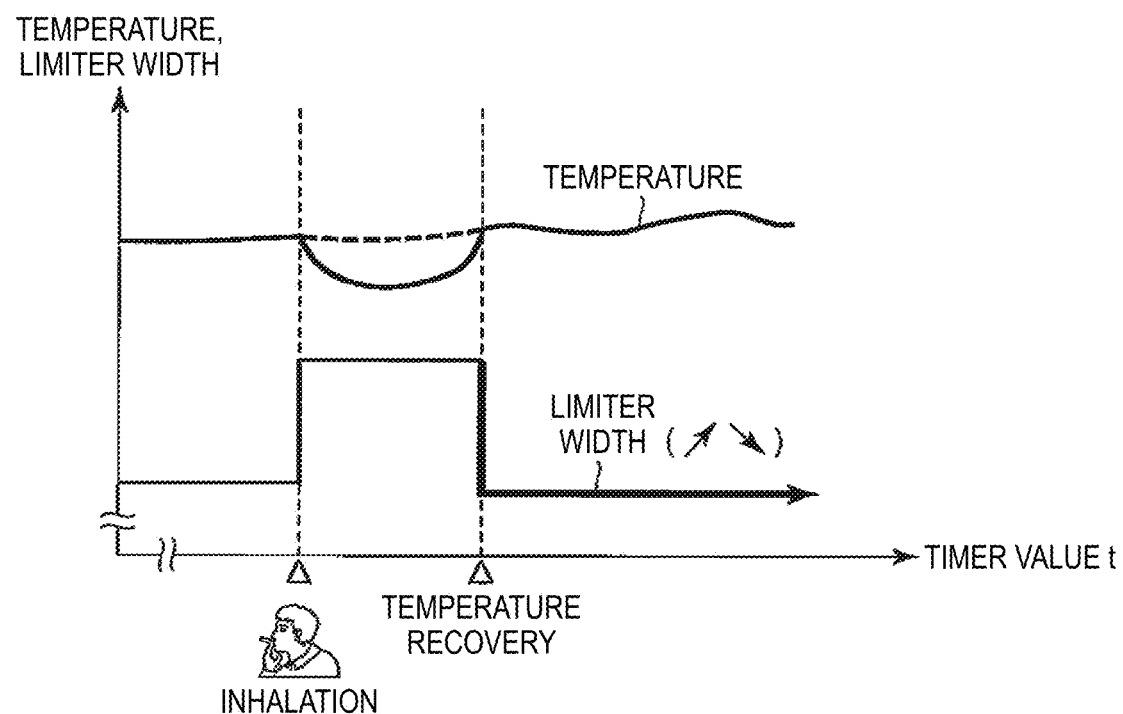
FIG. 51 is a graph depicting an example of changes in the temperature of the load and the limiter width in accordance with Example 5E.

FIG. 51 is a graph depicting an example of changes in the temperature of the load 3 and the limiter width in accordance with Example 5E. In the graph, the horizontal axis indicates the timer value t, and the vertical axis indicates the temperature of the load 3 and the limiter width.

As described above, the temperature of the load 3 is decreased upon the inhalation. When the inhalation is detected, the limiter change unit 13 of the control unit 8 expands the limiter width, so that the control unit 8 recovers the decreased temperature of the load 3.

The limiter change unit 13 detects the recovery of the temperature of the load 3 when the temperature of the load 3 returns to the state before the inhalation detection or when a predetermined time elapses since the inhalation detection, for example. Then, the limiter change unit 13 returns the limiter width to a value before the inhalation is detected.

The control of Example 5E can also be applied to a case where the temperature of the load 3 is kept constant.

Figure 52:
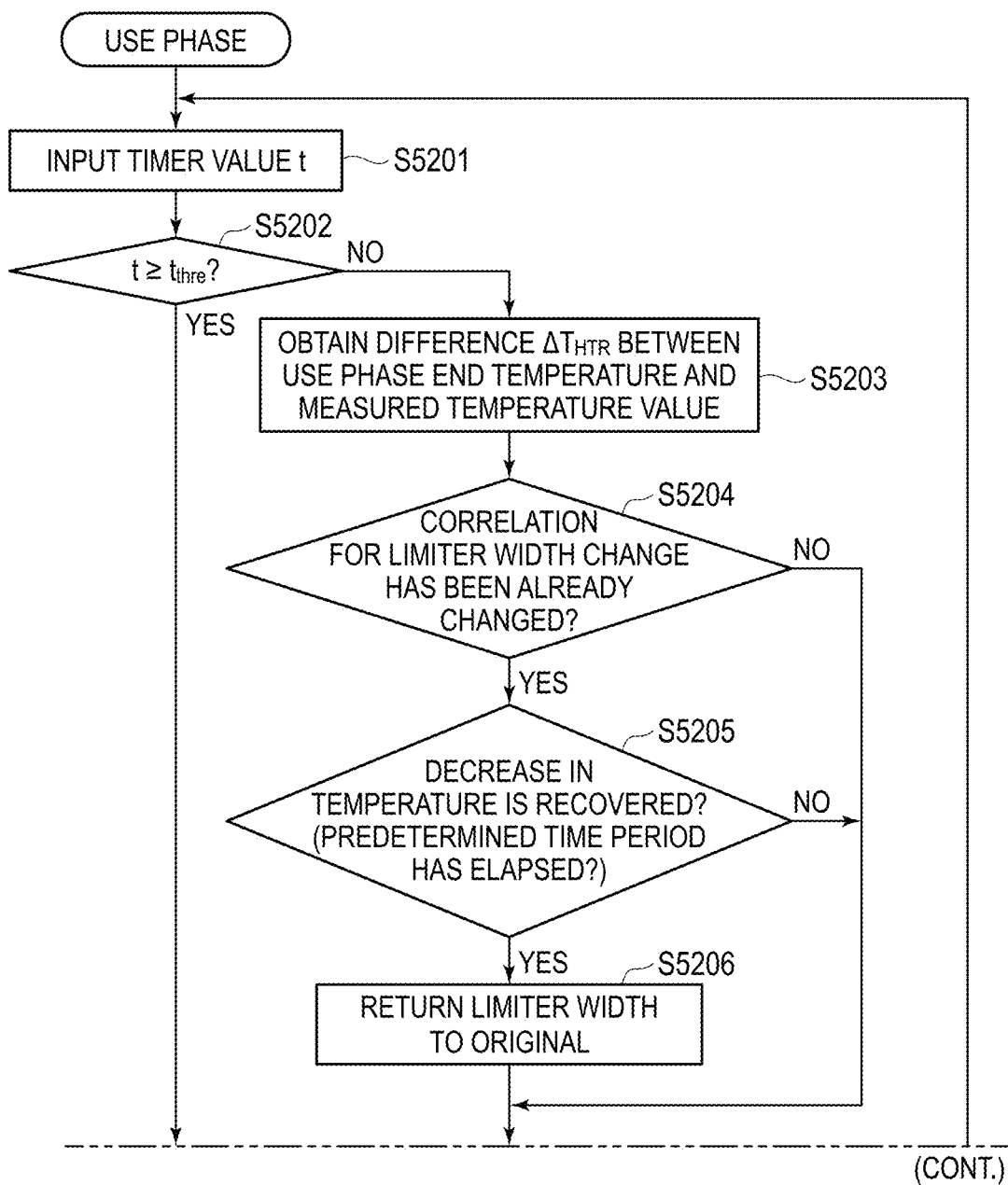
FIG. 52 is a flowchart depicting an example of processing in the use phase by the control unit in accordance with Example 5E.

FIG. 52 is a flowchart depicting an example of processing in the use phase by the control unit 8 in accordance with Example 5E.

The processing from step S5201 to step S5205 is the same as the processing from step S4601 to step S4605 in FIG. 46.

In step S5204, when it is determined that the correlation for limiter width change has not been already changed (a determination result is negative), the processing proceeds to step S5207.

When it is also determined in step S5205 that the decrease in temperature of the load 3 has not been recovered (a determination result is negative), the processing proceeds to step S5207.

When it is determined in step S5205 that the decrease in temperature of the load 3 has been recovered (a determination result is affirmative), the limiter change unit 13 returns the limiter width to an original state in step S5206, and the processing proceeds to step S5207.

In step S5207, the control unit 8 determines whether the inhalation is detected.

When it is determined that the inhalation is not detected (a determination result in step S5207 is negative), the processing proceeds to step S5209.

When it is determined that the inhalation is detected (a determination result in step S5207 is affirmative), the limiter change unit 13 expands the limiter width that is used in the limiter unit 14, in step S5208, and proceeds to step S5209.

The processing from step S5209 to step S5212 is the same as the processing from step S4609 to step S4612 in FIG. 46.

In Example 5E as described above, when the inhalation is detected, the temperature of the load 3 can be recovered promptly and appropriately, and after the temperature of the load 3 is recovered, the limiter width that is used in the limiter unit 14 can be again returned to the value before the inhalation is detected. Thereby, the temperature of the load 3 can be stabilized.

The above embodiments can be freely combined. The embodiments are exemplary and are not intended to limit the scope of the invention. The embodiments can be implemented in other diverse forms, and can be diversely omitted, replaced and changed without departing from the gist of the invention. The embodiments and modifications thereof are included in the claims and the equivalent scope thereof as well as the scope and gist of the invention.

What is claimed is:

1. An aerosol generation device comprising:
   a load configured to heat an aerosol generation article by using power that is supplied from a power source, the aerosol generation article comprising an aerosol-forming substrate configured to hold or carry at least one of an aerosol source and a flavor source; and
   circuitry configured to control the power that is supplied from the power source to the load,
   wherein in a case of a use phase where a temperature of the load is equal to or higher than a value at which a predetermined amount or more of aerosols is capable of being generated from the aerosol generation article, the circuitry is configured to acquire the temperature of the load and a degree of progress of the use phase, execute feedback control so that the temperature of the load converges to a predetermined temperature, and increase a gain in the feedback control or an upper limit value of the power that is supplied from the power source to the load, as the degree of progress progresses, in the feedback control.

2. The aerosol generation device according to claim 1, wherein the circuitry is configured to increase the gain or the upper limit value as the degree of progress progresses so that the temperature of the load does not decrease from start of the use phase.

3. The aerosol generation device according to claim 1, wherein an increase width of the gain or the upper limit value with respect to a progressing width of the degree of progress is constant.

4. The aerosol generation device according to claim 1, wherein the circuitry is configured to change an increase rate of the gain or the upper limit value with respect to a progressing width of the degree of progress.

5. The aerosol generation device according to claim 4, wherein the circuitry is configured to increase the increase rate as the degree of progress progresses.

6. The aerosol generation device according to claim 4, wherein the circuitry is configured to reduce the increase rate as the degree of progress progresses.

7. The aerosol generation device according to claim 1, wherein the circuitry is configured to:
   determine the gain or the upper limit value corresponding to the degree of progress based on a relation where the gain or the upper limit value increases as the degree of progress progresses; and
   change the relation based on a time-series change in the degree of progress.

8. The aerosol generation device according to claim 7, wherein the circuitry is configured to change the relation so that the gain or the upper limit value increases as the degree of progress progresses.

9. The aerosol generation device according to claim 7, wherein
   in a case that the degree of progress is delayed in comparison with a predetermined degree of progress, the circuitry is configured to change the relation so that an increase width of the gain or the upper limit value corresponding to a progressing width of the degree of progress increases, and the degree of progress is the temperature of the load.

10. The aerosol generation device according to claim 7, wherein in a case that the degree of progress is further progressed in comparison with a predetermined degree of progress, the circuitry is configured to change the relation so that an increase width of the gain or the upper limit value corresponding to a progressing width of the degree of progress decreases, and the degree of progress is the temperature of the load.

11. The aerosol generation device according to claim 7, wherein in a case that the degree of progress is delayed in comparison with a predetermined degree of progress, the circuitry is configured to change the relation so that an increase width of the gain or the upper limit value corresponding to a progressing width of the degree of progress decreases, and the degree of progress is one of a number of times of aerosol inhalation, an amount of aerosol inhalation, and an amount of aerosol generation.

12. The aerosol generation device according to claim 7, wherein in a case that the degree of progress is further progressed in comparison with a predetermined degree of progress, the circuitry is configured to change the relation so that an increase width of the gain or the upper limit value corresponding with respect to a progressing width of the degree of progress increases, and the degree of progress is one of a number of times of aerosol inhalation, an amount of aerosol inhalation, and an amount of aerosol generation.

13. The aerosol generation device according to claim 7, wherein the circuitry is configured to temporarily change the relation or to change a part of the relation.

14. The aerosol generation device according to claim 7, wherein the circuitry is configured to change an entire part of the relation that is after the latest degree of progress acquired.

15. The aerosol generation device according to claim 7, wherein the circuitry is configured to:

change a part of the relation that is after the latest degree of progress acquired by the control unit; and set a relation between the degree of progress and the gain or the upper limit value at the end of the use phase to be the same before and after the change of the relation.

16. The aerosol generation device according to claim 1, wherein the predetermined temperature is a temperature of the load that is necessary to generate aerosols from the aerosol source or the aerosol-forming substrate included in mounted aerosol generation article and located in a position most distant from the load.

17. The aerosol generation device according to claim 1, wherein the degree of progress is lapse time of the use phase, a number of times of aerosol inhalation, an amount of aerosol inhalation, an amount of aerosol generation or a temperature of the load.

18. A control method of power that is supplied from a power source to a load, the load being used to heat an aerosol generation article comprising an aerosol-forming substrate configured to hold or carry at least one of an aerosol source and a flavor source, the control method comprising:

starting supply of the power from the power source to the load;

in a case of a use phase where a temperature of the load is equal to or higher than a value at which a predetermined amount or more of aerosols is capable of being generated from the aerosol generation article, acquiring the temperature of the load and a degree of progress of the use phase;

executing feedback control so that the temperature of the load converges to a predetermined temperature; and increasing a gain in the feedback control or an upper limit value of the power that is supplied from the power source to the load, as the degree of progress progresses, in the feedback control.

19. An aerosol generation device comprising:

a load configured to heat an aerosol generation article by using power that is supplied from a power source, the aerosol generation article comprising an aerosol-forming substrate configured to hold or carry at least one of an aerosol source and a flavor source; and circuitry configured to acquire a temperature of the load;

execute feedback control based on the temperature of the load; and control the power that is supplied from the power source to the load, wherein the circuitry is configured to increase a gain in the feedback control or an upper limit value of the power that is supplied from the power source to the load so that the temperature of the load gradually approaches from a first temperature, at which a predetermined amount or more of aerosols is capable of being generated from the aerosol source or the aerosol-forming substrate included in the aerosol generation article and located in a position closest to the load, to a second temperature at which the predetermined amount or more of aerosols is capable of being generated from the aerosol source or the aerosol-forming substrate included in the aerosol generation article and located in a position most distant from the load.

20. A computer-readable non-transitory storage medium storing a program for causing a computer to implement the control method according to claim 18.

* * * * *